(12) United States Patent
Omid-Zohoor et al.

(10) Patent No.: US 11,673,024 B2
(45) Date of Patent: Jun. 13, 2023

(54) METHOD AND SYSTEM FOR HUMAN MOTION ANALYSIS AND INSTRUCTION

(71) Applicant: PG Tech, LLC, Scottsdale, AZ (US)

(72) Inventors: Alex B. Omid-Zohoor, Scottsdale, AZ (US); Brian Vermilyea, Scottsdale, AZ (US); Erik Herter, Scottsdale, AZ (US); Tony Morgan, Scottsdale, AZ (US); Steve Diamond, Scottsdale, AZ (US); Michael Chu, Scottsdale, AZ (US); Eran Leshem, Scottsdale, AZ (US)

(73) Assignee: PG TECH, LLC, Scottsdale, AZ (US)

( * ) Notice: Subject to any disclaimer, the term of this patent is extended or adjusted under 35 U.S.C. 154(b) by 999 days.

(21) Appl. No.: 16/253,155

(22) Filed: Jan. 21, 2019

(65) Prior Publication Data

US 2019/0224528 A1   Jul. 25, 2019

Related U.S. Application Data

(60) Provisional application No. 62/620,325, filed on Jan. 22, 2018, provisional application No. 62/620,296, filed on Jan. 22, 2018.

(51) Int. Cl.
*A63B 24/00* (2006.01)
*A61B 5/11* (2006.01)
(Continued)

(52) U.S. Cl.
CPC ........ *A63B 24/0075* (2013.01); *A61B 5/0022* (2013.01); *A61B 5/0024* (2013.01);
(Continued)

(58) Field of Classification Search
CPC ............ A63B 24/0075; A63B 24/0003; A63B 2102/32; G16H 50/20; G16H 20/30;
(Continued)

(56) References Cited

U.S. PATENT DOCUMENTS

| 4,137,566 A | 1/1979 | Haas et al. |
| 4,163,941 A | 8/1979 | Linn, Jr. |

(Continued)

*Primary Examiner* — Jay Trent Liddle
*Assistant Examiner* — Alyssa N Brandley
(74) *Attorney, Agent, or Firm* — Dentons US LLP

(57) ABSTRACT

A system and method for analyzing and improving the performance of a body motion, which requires receiving, by a CPU, sensor data from sensors worn by a user; storing the transmitted sensor data in a data buffer; recognizing that a motion gesture occurred based on a signature of acceleration data in the buffered sensor data, extracting from the data buffer sensor data from a predetermined time window around the moment when the motion gesture occurred; automatically generating a regime file customized for the user based on the extracted sensor data, and generating in real-time a user interface displaying a representation corresponding to the motion indicated by the sensor data, wherein the CPU determines the signature of acceleration data by matching the buffered sensor data with stored motion signatures, wherein the regime file is automatically generated based on diagnostic parameters obtained from the sensor data associated with a motion activity category.

9 Claims, 63 Drawing Sheets

(51) Int. Cl.
*A61B 5/00* (2006.01)
*G16H 50/20* (2018.01)
*G16H 20/30* (2018.01)
*G16H 40/67* (2018.01)
*A63B 102/32* (2015.01)

(52) U.S. Cl.
CPC .......... *A61B 5/1114* (2013.01); *A61B 5/1123* (2013.01); *A61B 5/6805* (2013.01); *A61B 5/6806* (2013.01); *A61B 5/6895* (2013.01); *A61B 5/742* (2013.01); *A63B 24/0003* (2013.01); *G16H 20/30* (2018.01); *G16H 40/67* (2018.01); *G16H 50/20* (2018.01); *A61B 2562/0219* (2013.01); *A63B 2102/32* (2015.10)

(58) Field of Classification Search
CPC ... A61B 5/0022; A61B 5/0024; A61B 5/1114; A61B 5/1123; A61B 5/742; A61B 2562/0219; A61B 5/6805; A61B 5/6806; A61B 5/6895
USPC ........................................................ 434/247
See application file for complete search history.

(56) References Cited

U.S. PATENT DOCUMENTS

| | | |
|---|---|---|
| 4,337,049 A | 6/1982 | Connelly |
| 4,375,674 A | 3/1983 | Thornton |
| 4,631,676 A | 12/1986 | Pugh |
| 4,656,507 A | 4/1987 | Greaves et al. |
| 4,713,686 A | 12/1987 | Ozaki et al. |
| 4,828,500 A | 5/1989 | Seidel et al. |
| 4,860,096 A | 8/1989 | Long et al. |
| 5,072,294 A | 12/1991 | Engle |
| 5,111,410 A | 5/1992 | Nakayama et al. |
| 5,114,410 A | 5/1992 | Caralt Batlle |
| 5,184,295 A | 2/1993 | Mann |
| 5,221,088 A | 6/1993 | McTeigue et al. |
| 5,233,544 A | 8/1993 | Kobayashi |
| 5,342,054 A | 8/1994 | Chang et al. |
| 5,372,365 A | 12/1994 | McTeigue et al. |
| 5,419,562 A | 5/1995 | Cromarty |
| 5,459,793 A | 10/1995 | Naoi et al. |
| 5,486,001 A | 1/1996 | Baker |
| 5,501,463 A | 3/1996 | Gobush et al. |
| 5,553,846 A | 9/1996 | Frye et al. |
| 5,575,719 A | 11/1996 | Gobush et al. |
| 5,592,401 A | 1/1997 | Kramer |
| 5,697,791 A | 12/1997 | Nashner et al. |
| 5,772,522 A | 6/1998 | Nesbit et al. |
| 5,823,878 A | 10/1998 | Welch |
| 5,826,578 A | 10/1998 | Curchod |
| 5,864,960 A | 2/1999 | DeNicolo et al. |
| 5,904,484 A | 5/1999 | Burns |
| 5,907,819 A | 5/1999 | Johnson |
| 5,930,741 A | 7/1999 | Kramer |
| 5,935,014 A | 8/1999 | Lindsay |
| 5,984,810 A | 11/1999 | Frye et al. |
| 6,041,651 A | 3/2000 | Naruo et al. |
| 6,068,559 A | 5/2000 | Lubell et al. |
| 6,154,771 A | 11/2000 | Rangan et al. |
| 6,261,189 B1 | 7/2001 | Saville et al. |
| 6,293,802 B1 | 9/2001 | Ahlgren |
| 6,322,455 B1 | 11/2001 | Howey |
| 6,353,447 B1 | 3/2002 | Truluck et al. |
| 6,436,058 B1 | 8/2002 | Krahner et al. |
| 6,503,086 B1 | 1/2003 | Golubov |
| 6,514,081 B1 | 2/2003 | Mengoli |
| 6,537,076 B2 | 3/2003 | McNitt et al. |
| 6,567,536 B2 | 5/2003 | McNitt et al. |
| 6,587,809 B2 | 7/2003 | Majoe |
| 6,782,118 B2 | 8/2004 | Verga |
| 6,793,585 B1 | 9/2004 | Miyamoto et al. |
| 6,966,843 B2 | 11/2005 | Rankin et al. |
| 7,041,014 B2 | 5/2006 | Wright et al. |
| 7,074,168 B1 | 7/2006 | Farnes et al. |
| 7,101,287 B1 | 9/2006 | Wagner |
| 7,131,910 B2 | 11/2006 | Townsend, II |
| 7,465,257 B1 | 12/2008 | Morgan, Jr. |
| 7,503,878 B1 | 3/2009 | Amsbury et al. |
| 7,587,065 B2 | 9/2009 | Matsumoto et al. |
| 7,625,316 B1 | 12/2009 | Amsbury et al. |
| 7,658,695 B1 | 2/2010 | Amsbury et al. |
| 7,857,708 B2 | 12/2010 | Ueda et al. |
| 7,887,440 B2 | 2/2011 | Wright et al. |
| 9,311,789 B1 | 4/2016 | Gwin |
| 9,675,875 B2 | 6/2017 | Dugan |
| 2002/0064764 A1 | 5/2002 | Fishman et al. |
| 2003/0095186 A1 | 5/2003 | Aman et al. |
| 2005/0085311 A1 | 4/2005 | Voges et al. |
| 2005/0223799 A1 | 10/2005 | Murphy |
| 2005/0261073 A1 | 11/2005 | Farrington, Jr. et al. |
| 2005/0272561 A1 | 12/2005 | Cammerata |
| 2006/0094570 A1 | 5/2006 | Schneider |
| 2006/0166737 A1* | 7/2006 | Bentley ................. A63F 13/812 463/43 |
| 2006/0247070 A1 | 11/2006 | Funk et al. |
| 2007/0172797 A1 | 7/2007 | Hada et al. |
| 2007/0249470 A1 | 10/2007 | Niva et al. |
| 2007/0270214 A1 | 11/2007 | Bentley |
| 2007/0298896 A1 | 12/2007 | Nusbaum et al. |
| 2009/0312152 A1* | 12/2009 | Kord .................. A63B 24/0006 482/8 |
| 2010/0033303 A1 | 2/2010 | Dugan et al. |
| 2010/0317489 A1 | 12/2010 | Flaction |
| 2010/0323805 A1 | 12/2010 | Kamino et al. |
| 2011/0046519 A1 | 2/2011 | Raheman |
| 2011/0251021 A1 | 10/2011 | Zavadsky et al. |
| 2012/0119911 A1 | 5/2012 | Jeon et al. |
| 2012/0183940 A1* | 7/2012 | Aragones ............... A61B 5/744 434/247 |
| 2013/0032634 A1 | 2/2013 | McKirdy |
| 2013/0196822 A1 | 8/2013 | Watterson et al. |
| 2013/0211858 A1 | 8/2013 | Ohnemus et al. |
| 2013/0236867 A1 | 9/2013 | Avni et al. |
| 2014/0073486 A1 | 3/2014 | Ahmed et al. |
| 2014/0081661 A1 | 3/2014 | Fu et al. |
| 2014/0135592 A1 | 5/2014 | Ohnemus et al. |
| 2014/0135593 A1 | 5/2014 | Jayalth et al. |
| 2014/0156308 A1 | 6/2014 | Ohnemus et al. |
| 2014/0180451 A1 | 6/2014 | Marty |
| 2014/0228985 A1* | 8/2014 | Elliott ...................... A61B 5/11 700/91 |
| 2014/0336947 A1 | 11/2014 | Walke et al. |
| 2015/0025419 A1 | 1/2015 | Aaberg |
| 2015/0133748 A1 | 5/2015 | Edmonds et al. |
| 2015/0148619 A1 | 5/2015 | Berg et al. |
| 2015/0230719 A1 | 8/2015 | Berg et al. |
| 2015/0251074 A1 | 9/2015 | Ahmed et al. |
| 2015/0302162 A1 | 10/2015 | Hughes et al. |
| 2016/0038083 A1 | 2/2016 | Ding et al. |
| 2016/0058335 A1 | 3/2016 | Ashby |
| 2016/0114213 A1 | 4/2016 | Lee |
| 2017/0004358 A1* | 1/2017 | Bose ...................... G06V 40/23 |
| 2018/0140902 A1 | 5/2018 | Wiebe et al. |

* cited by examiner

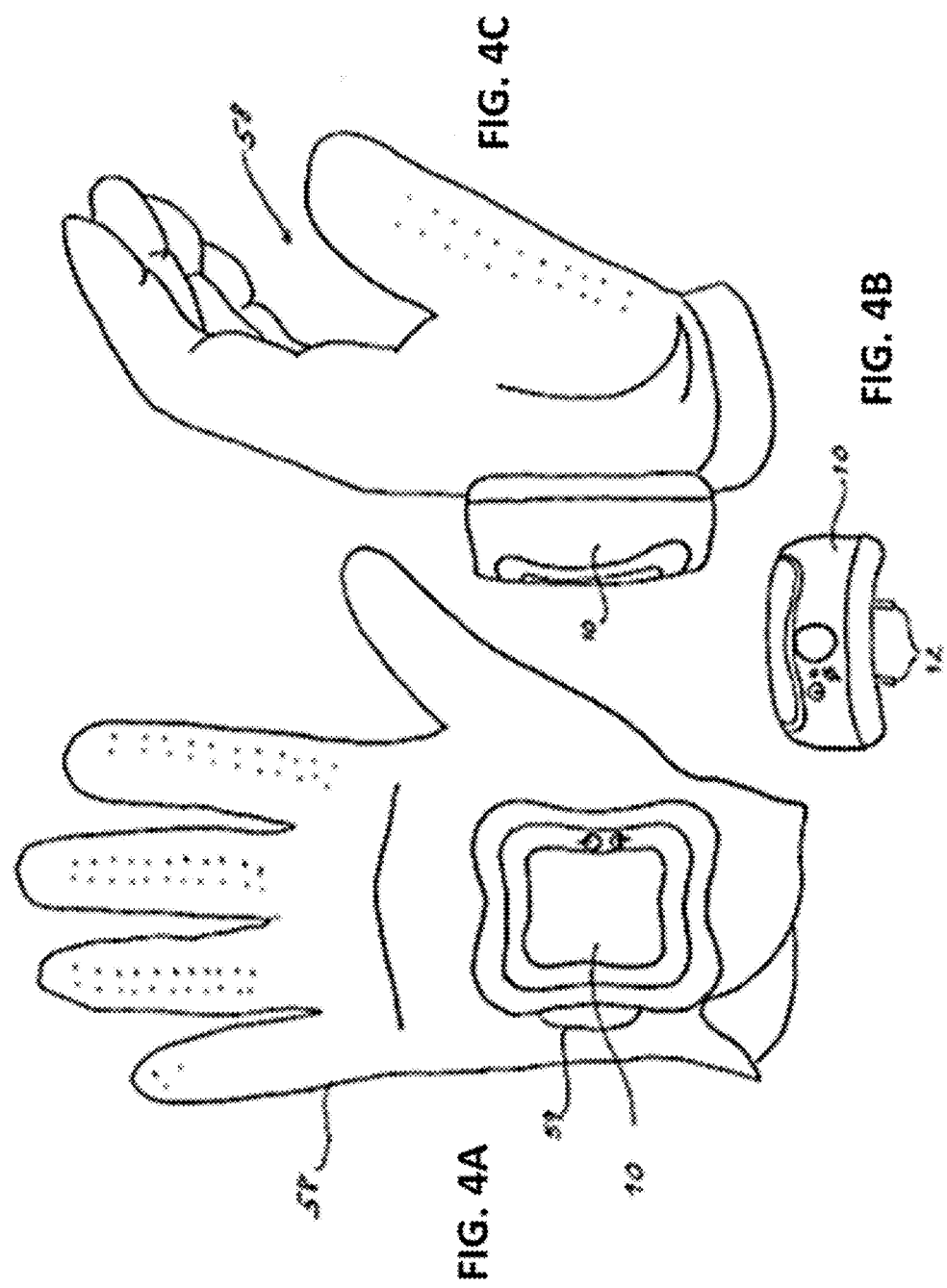

FIG. 46

METHOD AND SYSTEM FOR HUMAN MOTION ANALYSIS AND INSTRUCTION

CROSS-REFERENCE TO RELATED APPLICATIONS

This application claims priority to U.S. Provisional Application No. 62/620,325, filed on Jan. 22, 2018, and U.S. Provisional Application No. 62/620,296. This application incorporates by reference in their entirety the following: U.S. Provisional Application No. 62/620,325, filed on Jan. 22, 2018, U.S. Provisional Application No. 62/620,296. U.S. Pat. No. 9,770,658, entitled "Method and System for Athletic Motion Analysis and Instruction;" U.S. Pat. No. 8,619,989, entitled "Method and System for Athletic Motion Analysis and Instruction;" U.S. Pat. No. 7,264,554, entitled "Method and System for Athletic Motion Analysis and Instruction;" and U.S. patent application Ser. No. 15/008,107, entitled "Method and System for Athletic Motion Analysis and Instruction," filed on Jan. 27, 2016. Each application referenced above is incorporated by reference herein in its entirety.

TECHNICAL FIELD

This application relates generally to a human motion monitoring and instruction computer system, such system including motion capture sensors used by the system to analyze human motion, prescribe techniques related to the motion, and provide real time biofeedback.

BACKGROUND

Many different techniques have been implemented in order to teach the proper mechanics of various athletic motions, including swinging a golf club. Many instructors use a video analysis system to teach a student how to properly swing a golf club. Using a typical video analysis system, the student's golf swing is captured by a video-recording device. The instructor replays the recorded video information to illustrate the student's golf swing while providing feedback regarding the swing. Instructional feedback may be comments relative to problems associated with the student's swing, compliments regarding improvement in the student's swing, suggestions on correcting the user's swing, or any other verbal instructional comments in context with the student's swing. Visualizing one's personal golf swing in this manner has been recognized as a valuable tool in identifying problems as well as correcting those problems in order to improve the overall golf swing.

Video analysis systems have drawbacks. One drawback relates to having the video information subjectively analyzed. Not only is such analysis open to interpretation and subject to inaccuracies, but it is also exacerbated by the fact that many problems associated with a body movement are typically not captured by the video recording system given different camera angles, too few cameras, or loose clothing.

In order to overcome the drawbacks associated with typical video analysis systems, instructors have adopted motion or position analysis systems as an aid to analysis and instruction. Many conventional motion analysis systems require that the user (e.g., student/athlete) wear sensor elements on their body and the sensor elements transmit positional data of isolated body parts, such as hands, hips, shoulders and head. The isolated points on the body are measured during a swing in accordance with an absolute reference system, e.g., a Cartesian coordinate system wherein the center point is a fixed point in the room. By using motion analysis, exact measurements are provided from which an instructor can more accurately determine problems in a student's swing. Even though motion analysis provides accurate positional data of the student's swing, it is not, in and of itself, particularly useful since it gives no visual aid as to where the problems may really be. When used by itself, the motion analysis system is not an effective teaching tool since the instructor is only provided with numbers and not a visualization of what the student is doing wrong. Some motion analysis systems provide animation that depicts elements of a golf swing based upon captured data. However, the animation is crude and doesn't show the golfer what he/she looks like during a swing.

Another conventional system discloses a video device and method which detects the club head velocity via a colored club head and color detection unit. The club head velocity is then displayed in analog or digital form. A series of swings can then be analyzed by comparing the relative club head velocities for different club swings.

Yet another conventional system provides a video system which displays a live video signal of a golfer's swinging motion for the golfer to see while swinging. A series of video overlays can be imposed upon the video signal for reference and analysis purposes.

What is lacking in the field is a motion analysis apparatus and method which is capable of capturing and plotting the total motion of a user with sufficient data to reduce, analyze, report on, and present the component parts of the motion and the degree of coordination of the component parts as feedback to the user in such a way as to optimize his assimilation and understanding of the information; further to provide a comparative study of the component parts of the user's performance as to its own prior test results or the performance of other persons or other benchmark values; and further, to provide a related prescription of specific exercises tailored to the user's level of performance, areas of deficiency, and available time for improving his or her skill level through practice of training exercises.

For example, as a golf swing is executed, the golfer rotates, among other things, the hips, shoulders, and arms in a sequential, and yet coordinated fashion. To maximize energy in the swing, the golfer must smoothly transfer energy from the feet to the hips, to the shoulders, to the arms, and hence to the club, culminating at the time and point of impact with the ball. What is needed is a system and method of motion capture and data processing with specialized software to process this data and generate a coordinated, multiple format presentation to the user which will effectively demonstrate the most efficient kinetic link between the golfer's motion segments, and prescribe exercises likely to improve the user's performance.

It is with respect to these and other considerations that the present invention has been made.

SUMMARY

A kinetic link in the context of the invention is a chain of interdependent components of motion acting towards a common goal, the effective and efficient execution of the motion. This kinetic link principle is applicable to all dynamic, athletic-type body motions intended to perform work or convert or transfer energy in any manner by means of bodily exertion, with or without the use of a hand or foot actuated or operated tool or article of sporting equipment. For example, in a golf swing motion, the process of striking a golf ball with a golf club, the kinetic link is composed of four principle components of the motion with three links. These four components and three links in combination represent the full motion of the body. The components consist of the hip segment, shoulder segment, arm segment and the club. The links include the musculature found between each body segment. Since the frame of reference and the point from which this type of motion must be leveraged is the ground itself, a complete analysis of the motion must consider the feet first, then overall posture, then hips, then shoulders, then arms, then club, and finally the ball. A weakness at any point in the kinetic link results in a less than optimal total performance. Means of identifying and improving the component parts of the motion will improve the overall performance. This assumption is at the foundation of the present invention.

The invention is an improved global, knowledge-based, enterprise system and method for providing performance testing and training regimes to persons for whom athletic activities such as golfing, baseball, yoga, and others for whom repetitive athletic motions are an inherent part of their normal work or recreational activities, for improving the effectiveness of their golf swing or other specific athletic motion.

A typical example of the system and method uses state of the art technology and equipment for instrumenting a user or subject and monitoring a motion, draws upon and contributes to a vast library of performance data for analysis of the test results, provides an information rich, graphic display of the results in multiple, synchronized formats for user viewing and/or monitoring by a coach or system operator, and based on the results prescribes a user-specific training regime with exercises selected from a library of exercises.

Users and their coaches or observers may access the library of performance data to see and compare a user's (e.g., participant's) most recent test performance to its own or other users' prior test results. After an appropriate amount of off-line exercising, and/or at the desire of the user or coach, the testing is repeated. The specifics of the prescribed training are re-calculated and may include a weighted consideration of the current performance testing result in addition to prior test results. The performance reports provide an objective record of the type and degree of changes in performance that the user has experienced.

The system may be employed during live practice sessions to provide essentially instant or "real time" visual and/or auditory biofeedback and/or haptic feedback (vibration, etc.), or provide "replay" presentations, of each successive attempt at a particular drill or a full motion. Deviations in specific parameters from the objectives of the prescribed drills are reported and the user has the immediate opportunity to respond to the feedback and reduce the deviation of the specific parameter during an immediate next attempt at the same drill.

In one embodiment, a system and method for analyzing and improving the performance of an athletic motion such as a golf or baseball swing may require: instrumenting a user with sensors (e.g., inertial or movement sensors), and optionally including club or bat mounted/integrated sensors, video cameras, time of flight cameras, or radar-based systems capable of capturing 2D or 3D scene information at regular time intervals; monitoring a golf or baseball swing or other motion (athletic or otherwise) of interest; drawing upon and contributing to a vast library of performance data for analysis of the test results; scoring the motion; providing an information rich, graphic display of the results in multiple formats including video, color coded and stepped frame animations from motion data, and synchronized data/time graphs; and based on the results prescribing a user-specific training regime with exercises selected from a library of exercises with biofeedback. As discussed above, scoring the motion may involve scoring pre-defined parameters relating to component parts of the motion and combining the parameter scores to yield a single, kinetic index score for the motion.

The athletic motion is not limited to any particular type of human motion and by way of example includes golf, baseball, yoga, physical therapy exercises, hammering, sawing, throwing or using other handheld tools or sports equipment, a small sampling of which may include balls, bats, rackets, clubs, paddles, oars, spears, hammers, screwdrivers, staple guns, darts, horseshoes, and axes and others. It extends to running, kicking, jumping, pedaling and other foot/leg athletic motions using foot actuated tools and sports equipment including bicycles, balls, and foot-operated levers and other tools and objects.

The analysis reduces the full motion to predetermined major component motions. The coordinated data output portion of the results may represent the relative timing and amplitude of components of the user's own motion. The comparative data output may represent a comparison of the relative timing and amplitude of components of the user's motion to the same components of an expert or other standard performance data from the system database, or the user's own prior test performance data. The data processing and biofeedback may further include prescriptions from a database of standard exercises, tailored according to the user's level of performance and time available, for training on a component-of-motion basis, such as stance, balance, hip motion, and shoulder and arm motion, adjusted according to the user's actual performance data, or on a full movement that involves a plurality of motion components. The exercises may prescribe or presume the use of specialized tools and training aids from among a library of predetermined tools and training aids, during the exercises.

As described above, the data input, analysis, and the biofeedback report is preferably augmented by use of video, audio, and other recording devices emplaced and focused to capture additional motion data at a desired direction from the user under test, and processed to provide additional graphical, video, audio or other form of output that can be integrated with the data output for optimal user understanding and assimilation of the analysis and report. The biofeedback report may also be transmitted to a coach in real time.

The system and method in local or global embodiments may be applied to other athletic or occupational motions by which energy is transformed through user motion into work of any type, for improving performance, preventing injury and/or providing a rehabilitation program.

For example, a set of motion sensors, such as inertial or movement sensors, are attachable to the user's body, and/or motion tool or device such as a golf club or baseball bat, at strategic points by the use of specially designed appliances. Each motion sensor may contain a multi-element sensing system and circuitry for sensing and reporting three dimensional position and attitude of the sensor, transmitting a real time output of vector data for further application-specific processing.

The vector data from the full set of motion sensors is sufficient data from which to derive and characterize the principle components of a golf swing or other athletic motion, as is further described below. The information is transmitted in real time directly from each sensor individually, or via a common transmitter to which some or all the sensors may be hard wired, to a nearby receiver and hence to a processing computer for application-specific data processing and analysis, and generation of data and graphical output reports representing the user's performance, as is further described below. Additionally, the sensors may be configured to send sensor data to a local computer (e.g., participant device or observer device), which may then send the sensor data to a local remote server for processing, analysis, etc. The remote server may then send the results of such processing and analysis back to the local computer for display. Alternatively, the processing, analysis, etc. may be performed by the local computer.

The processing computer can perform relational calculations on the data received from the various sensors, thereby allowing computation of various application-related parameters of interest. As an example, the processing computer with its golf-specific software can calculate club-face angle or the angle through which the golfer turns his or her shoulders while swinging the golf club.

In a golf swing motion analysis system in particular, inertial sensor data is typically processed into the following parameters relating to the golfer's body performance: hip velocity (degrees per second); hip rotation (degrees negative and positive); shoulder velocity (degrees per second); shoulder rotation (degrees negative and positive); club release (degrees per second); club speed (miles per hour); club face rotation (degrees open/closed); club path (degrees inside or outside of club's address position); hip linear movement (centimeters left or right of neutral address); hip shoulder separation (time difference between maximum hip, shoulder, and club velocity); flexion/extension of hip segment (centimeters traveled along z-axis); and kinetic link. These parameters are further extrapolated to yield a predicted "ball in flight" resulting performance of parameters: spin (degrees per second); launch angle (degrees); carry distance; roll distance (yards); total distance (yards); distance traveled off line (yards right or left); ball flight character (fade, draw, hook, slice, push, pull, straight); and PTI or power transfer index.

The processing computer can also display information about the swing that will allow the golfer or his or her instructor to visualize and adjust the swing. For example, in one aspect, the system displays live video feed of the golfer (obtained through a video feed from a video camera critically positioned adjacent to the golfer and coupled wirelessly or otherwise to the processing computer), an animated simplification of the same motion generated from motion data, and statistics reporting the state of the various parameters in any given freeze-frame. The system can also display the results of the various calculations of performance parameters, which characterize the swing over time; for example, the system can display data regarding the club-face angle or the angle through which the shoulders rotate during a particular swing.

A system interface (e.g., participant device) between the processing computer and the golfer in the form of a control or feedback module mounted on or near the instrumented golfer can provide instructions to the golfer in preparation for or in response to a particular attempted golf swing. The system interface may instruct the golfer, for example, to address the ball, give a five-second window for the golfer to initiate a swing, etc. Such instructions may in one embodiment be in the form of audible beeps, or synthetic speech or pre-recorded voice commands. Colored lamps or a backlit LCD or other type visual signal display can also issue coded or alphanumeric instructions. Such functions are useful in securing specific and timely inputs needed to calibrate the sensors for absolute position, as well as to coordinate the orderly sequencing or progress of a testing session.

In one response mode, the system can be characterized as operating in a "biofeedback mode," where the processing computer through the system interface assists the golfer in following prescribed exercises (described in more detail below). In that mode, the processing computer can also display on its display unit or screen, to the golfer and/or his instructor, one or more calculated performance parameters and video images of the golfer. Calculated diagnostic parameters of interest can be reported on the screen, stored for later analysis, or converted into success or failure codes, which can be transmitted back to the golfer and/or his instructor, or any combination of those actions.

Codes transmitted as biofeedback to the golfer may be in the form of a tone or a color that differs between a successful swing and an unsuccessful swing, or haptic feedback (vibration, etc.). For example, if the system is programmed and set up for training the golfer in a set of exercises where the golfer tries to rotate the shoulders through exactly 40 degrees from vertical, the system, as through a control module, can alert the golfer through tones or lights or changing colors within the graphic display screen, or vibration (e.g., an inconsistent or bad stroke may be alerted with a tactile vibration stimulus). when the swing differs from the ideal rotation angle by more than a predetermined error. For example, only if the rotation angle falls between 35-45 degrees, will the swing be considered a success. The tones or changing lights or haptic feedback may have several bands or ranges, allowing intermediate or scaled results. For example, a red light might follow a swing in which a diagnostic parameter badly diverged from ideal, a yellow light might follow a swing in which the same diagnostic parameter only somewhat diverged from ideal, and a green light might follow a swing in which the same diagnostic parameter diverged from ideal by less than the pre-assigned margin of error. The signal light may be the background color of an animation. The information conveyed by the changing color of the selected illuminated portion of a screen may be likewise presented with same or more or less detail in other audio, textual, numerical and/or graphical formats, including numbers, bar graphs, line graphs and text messages. Oral callouts may be used in combination or in the alternative.

The feedback report may also be continuous or highly differentiated; for example, the length of an audible tone or haptic vibration might correspond to the extent to which the diagnostic parameter diverged from ideal, and the golfer is instructed to practice until the tone shortens or disappears. The number of blinks of a light, light color, sound frequency, sound volume, vibration length, vibration strength, vibration frequency, tone length, and tone type are among the characteristics that can be used in the feedback mode. The audio format feedback information can be produced with synthesized voice output from a speaker or earphones.

The processing computer and system interface also can include monitoring by a golf professional or other motion expert or instructor, directly or remotely as through an internet connection, and allow him or her to transmit to the golfer instructions to initiate, cease, or control exercises through instructor command inputs to the system, or received by the system from a remote location, such as through an internet connection.

After computation of the various golf-related parameters of interest, those diagnostic parameters can be utilized by indexing a cross reference table of test results and exercises to automatically prescribe to the golfer an assignment of appropriate individualized exercises to improve his or her swing. In one embodiment, each calculated diagnostic parameter is divided into two, three, or more ranges, with each range corresponding to a prescribed action with respect to a particular exercise. For example, a first range for a particular diagnostic parameter can result in a prescription of a certain exercise, a second range of the same parameter can result in a different prescription, and a third range of the same parameter can result in no prescribed exercise because the golfer does not have a problem with the particular aspect of the swing that the parameter measures. The different prescription in each example can be, for example, a specific different number of repetitions of a given exercise, a different priority level given to a given exercise (see next paragraph for priority levels), a different exercise tool or accessory being used for a given exercise, or an entirely different exercise. Further, the frequency and duration of the exercises may be apportioned by the prescription compiler in accordance with the golfer's available time and schedule, as it was previously inputted to the system by the golfer.

Alternatively, the prescriptions may result from combinations of results from two or more diagnostic parameters. In variations, the knowledge base may include rules developed through automated analysis techniques based on measured results produced by the swing, or principles of fuzzy logic. In one embodiment, the diagnostic parameters produce exercise prescriptions with assigned priority levels. For example, if a particular golfer's swing produces one diagnostic parameter that is very far from ideal while other diagnostic parameters diverge from ideal only partly, the first diagnostic parameter will be assigned a higher priority level than the others. For another example, if two diagnostic parameters diverge from ideal but one is considered more important to a good golf swing or alternatively one is considered important to control to provide a good foundation for the other, then that one will be assigned a higher priority level than the other.

In one embodiment, each prescribed training exercise is assigned a priority level from one to nine, and several exercises may be assigned a common priority level. In that embodiment, the golfer or the instructor can indicate by input to the computer how much time the golfer has available to perform the exercises, and based on that information, the system can recommend which ones to perform. For example, if an athletic motion analysis system projects a need for three exercises with a priority level of one, five exercises given priority level two, and four other exercises with higher priorities, and if each exercise has been determined to require at least fifteen minutes to perform for reasonable effectiveness, and the golfer has a limited time for exercise, then the system might assign or prescribe accordingly. As specific examples, if the golfer indicates that he or she has one hour available, the assignment may be performing only the three priority one exercises for twenty minutes each. If the golfer has two hours available, the system might prescribe performing all priority one and all priority two exercises for fifteen minutes each. If the golfer has three hours available, the system might assign all exercises for fifteen minutes each. The minimum times to perform each different exercise might vary, the time recommended to perform any particular exercise might vary or be fixed, and the gradations of priority can be changed as desired.

The diagnostic parameters can also or alternatively be used to prescribe, select or fit golf equipment to the golfer, such as golf clubs or golf shoes from among one of several types or customized versions having particular measured parameters. For example, the length, lie angle, loft, or weight of a particular type of golf club can be selected based on analysis of the diagnostic parameters calculated for the golfer, preferably in combination with parameters about the golfer, such as his or her height, hand length, and foot size.

In another aspect, parameters calculated at time of impact, such as position and orientation of the club face relative to the ball and velocity vector and face angle of the club, can be used by the system to predict the forces on the ball and thus predict its trajectory. Knowledge of the terrain can allow determination of the distance and path of the struck golf ball, or alternatively the calculation can predict distance assuming the terrain is flat. Such predictions based purely on force calculations can be supplemented with information about the behavior of the ball in atmosphere, such as through testing of particular types of golf balls, to adjust for air resistance. In a further variation, wind direction and velocity can be taken into account, with such data input into the system manually or through an electronic anemometer or local air data station coupled to the system electrically, or via an internet or wireless connection.

The system may be remotely or locally controlled so that an off-site or on-site instructor may direct the operation of the system or monitor the results. In a purely user-contained mode, control inputs for set up and testing operations may be entered, test exercises performed, and swing data viewed and reviewed by a user with the aid of a personal control module and data monitoring system such as a belt-worn control/display unit or module.

The methodology and the system are applicable to other repetitive athletic and occupational motions for testing of animals or humans, analysis, reporting, diagnostic review by coaches, trainers and/or medical personnel or physical therapists, with prescriptions being similarly generated for training to improve performance, prevent injury, or for rehabilitation of various motion capabilities where the motion is susceptible of data collection and reduction into component parts in the manner described above, and the report can be presented in a synchronized, composite display of animation, multiple data tracks and video format.

It is an additional goal that the report and the prescribed regime of practice drills can be accessed remotely through a browser-based, on-line access point connecting to the local system or to a host, knowledge-based enterprise system to which it is connected, for later review and practice.

Therefore, the invention in one aspect consists of a method and apparatus for analysis and improvement of a selected athletic motion of an individual, consisting the steps of using a computer-based motion analysis system that has a processing computer, inertial sensors, a video camera which may be of any analog or digital technology, and a computer-driven display screen; testing an individual doing the athletic motion, with a tool if a tool is implied, by monitoring the execution of the motion with multiple inertial sensors mounted on the individual and optionally on the tool, with the video camera or cameras directed at the individual in action.

The video camera, when used, should be positioned to insure alignment with the individual under test and useful points of reference for measurement and analysis of the motion. The sensors should be positioned (possibly with the use of body wearable appliances) to insure that sensor data will reflect body motion accurately. Sensor data may be collected from the sensors and video signal from the camera (and possibly other motion data collected by additional sensors) during the execution of the athletic motion; and the sensor data is analyzed by processing the sensor data into motion data representing pre-defined selected performance parameters of pre-defined selected components of the athletic motion as may be accomplished by or attributable to specific or distinctive body segments such as the leg, hip, shoulder, neck, head, arm and hand aspects of a motion. The results of the analyzing is reported or presented in a form that includes a real time, computer generated display of multiple, selectable configurations, one of which includes in a composite, synchronized combination of the video signal as a video display, a multi-color, three dimensional animation representing the motion of at least one color-coded body segment created from the motion data, and a time-based graph of multiple selected performance parameters.

There may be provision for setting a range of motion limit for selected components of motion such as a specific bending or flexing component of the motion in advance of the testing. The animation of the motion may incorporate a three dimensional wire mesh cage or open frame representing the motion limits within which the body segment is visible. The software may provide for altering a selected color within the display upon the occurrence of a motion exceeding the motion limits, as a highly visible, instant signal to the individual that the limit has been reached or exceeded. Stepped levels of indication of approaching or exceeding pre-set limits may be used by using multiple color changes such as from green to orange to red.

The analysis may include for selected parameters comparing the motion data test value to a pre-defined benchmark value for the same parameter and determining a degree of deviation, and presenting on a time-based graph the test value and the benchmark value concurrently. The analysis may include calculating from the test values and the benchmark values a score for each selected parameter. It may further include combining the scores of the selected parameters by a pre-defined formula so as to yield a single score representing the total performance value of the athletic motion as a kinetic index.

The system and software may include with or follow the report or presentation with a prescription of a regime of training exercises selected from a pre-defined list of exercises based on the amount of the deviation from the benchmark values of individual parameters, and the exercises may be associated with a pre-defined list of training tools. The frequency and length of periods of exercise may be limited by the available training time of the individual, as may have been entered into the processing computer ahead of the testing.

The wireless inertial sensors may be attached to body appliances that are worn by the individual. The sensors and the appliances may have correspondingly keyed mating structural by which the sensors are uniformly and repeatably attachable to the same place with the same orientation on the appliances.

The results of the analyzing, including the motion data and the video data, may be stored in a local or remote computer database and made available for later replay locally or via a remote computer or computer network connected or connectable to the processing computer.

The camera, if employed, may be set up in advance of testing using a reference target or frame placed on the test site so as to define at least one point or line of reference relative to the motion to be tested. The software may be configured for overlaying the video display during a calibration phase with reference points, lines or other symbols relating to aspects of the motion, such as alignment lines, center lines, balance points of the starting, ending or in-motion positions of the user, by which motion can be more critically observed. The effectiveness of the lines and symbols overlaid on the video display may be dependent on correct camera placement prior to testing.

Embodiments of the invention may include a human motion monitoring system having one or more participant devices (e.g., computer, PDA, smartphone, etc.), one or more sensors (e.g., body mountable sensors), one or more observer devices (e.g., computer, PDA, smartphone, etc.), one or more databases, one or more servers, and one or more networks. For example, the one or more databases may include an exercise database, a participant database, an observer database, and a motion database.

Embodiments of the invention may include an autonomous training system for a motion instruction system that may be employed wherein a regime file of recommended exercises is customizable for individual participants based on data in a participant database. The customizable regime files may be used with groups of participants wherein each participant is at a different level of proficiency. Thus, the customizable regime files allow all participants to be together in a class setting wherein all of the participants receive unique versions of the same program based on individual participant profiles.

Embodiments of the invention may include a human motion monitoring system that utilizes data from an exercise database, participant database, observer database, and a motion database to generate a regime file that is customized to a single participant. The regime file may be generated autonomously using a content-based filtering approach, which leverages a machine learning model. Alternatively, the regime file may be generated autonomously using a collaborative filtering approach, which leverages a machine learning model on data associated with all participants. Alternatively, the regime file may be generated with a hybrid approach of both content-based filtering and collaborative filtering. In this manner, for example, the server may be configured to automatically generate a set of exercises for all participants based on diagnostic and/or performance parameters of the sensor data received from the participant device.

Embodiments of the invention may include a human motion monitoring system that applies machine learning techniques to learn relationships, functions, and categories associated with various analysis procedures, which may include modeling or scoring a particular motion gesture (e.g., golf swing) or exercise based on the sensor data. A supervised machine learning algorithm offers flexibility as it trains motion scoring models based on data, such as data contained in an exercise database, a participant database, an observer database, a motion database, and/or subsets thereof.

Embodiments of the invention may include a human motion monitoring system that operates in a dynamic biofeedback mode so that the processing computer performs a dynamic motion scoring process and trains a dynamic motion as opposed to one or more static postures. For example, the system may compare biomechanical parameters computed for a captured motion to a previously generated motion template stored in a database. The system may then compute a similarity score to represent a degree of mismatch based on the comparison.

Embodiments of the invention may include a human motion monitoring system that generates comprehensive user health, fitness, and skill scores based on a plurality of diagnostic scores.

Embodiments of the invention may include a human motion monitoring system configured to continually monitor participant compliance with a training regime.

Embodiments of the invention may include a human motion monitoring system configured so that during exercise routines, real-time feedback or analysis may be provided to the user based on sensed data, including image data, about the user. In this manner, the system may function as a "virtual coach" to the user to help make exercising more interactive and help achieve results and goals of the user faster.

Embodiments of the invention may include a human motion monitoring system that, in a golf application, measures a particular signature of at least one of acceleration data, body segment orientation data, and rotational velocity data that occurs when a golfer strikes a golf ball. This impact can be measured by a handset sensor, wrist sensor, and/or a club mounted sensor. The signature may be used by the system to automatically identify a particular motion gesture (e.g., golf swing). Then a predetermined time window of the sensor data may be analyzed by the system.

Embodiments of the invention may include a human motion monitoring system that, in a baseball application, measures a particular signature of acceleration that occurs when a batter strikes a baseball may result in a particular signature of at least one of acceleration data, body segment orientation data, and rotational velocity data. This impact can be measured by a handset sensor, wrist sensor, and/or a bat mounted sensor. The signature may be used by the system to automatically identify a particular motion gesture (e.g., baseball bat swing). Then a predetermined time window of the sensor data may be analyzed by the system.

Embodiments of the invention may include a human motion monitoring system that is configured to connect to launch monitors and is capable of showing the status of the connection on a user interface so that a user will know the launch monitor is communicably connected thereto.

Embodiments of the invention may include a human motion monitoring system that generates a user interface which displays the status of sensor connections to the system, such as by an indicator light or image.

Embodiments of the invention may include a human motion monitoring system capable of operating in different modes from a single interface to monitor different sports or activities, such as golf, baseball, physical therapy, yoga, etc., in order to support different motion types.

Embodiments of the invention may include a human motion monitoring system capable of generating, displaying on a user interface, and storing (in the cloud) display graphs and data of previously captured motions, time series of kinematic sequence (rotational velocities), pelvic bend, pelvis angles, upper body angles, spine rotation, etc. Using specific algorithms, the system may generate markers of motion-specific key frames, such as impact, for each of the generated graphs.

Embodiments of the invention may include a human motion monitoring system capable of generating, displaying on a user interface, and storing (in the cloud) display reports based on previously captured motion data. For example, the system may compute and display the order in which body segments begin their negative rotation in a swing motion. Similarly, the system may compute and display the order in which body segments "transition" from negative to positive rotation in a swing motion. The system may compute and display peak speeds of body segments in a swing motion. The system may compute and display the order in which body segments reach their peak speeds in a swing motion (referred to as "peak speed sequence"). The system may compute and display peak speed ratios (referred to as "speed gain"). The system may compute and display a swing summary and/or efficiency summary of the user as compared with motion data from another individual, such as a professional athlete.

Embodiments of the invention may include a human motion monitoring system capable of automatically generating exercise recommendations (e.g., regimes) with biofeedback. For example, the system may employ a heuristics-based approach that computes flaws from a single swing motion and generates a list of one or more biofeedback exercises for the user to perform to improve the flaws.

Embodiments of the invention may include a human motion monitoring system capable of generating animations on a graphical user interface to be displayed on a display device in real time or playback mode, the animation generation driven in part by the motion sensor inputs. For example, the system may be configured to display 3D animation playback of previously captured motions for a user. The system may be configured to render a 3D animation in real time from streaming sensor data. The system may be configured to change "camera" perspective in animation playback (e.g., user can manipulate the view of the animation to see the front view, side view, back view, top view, etc.). The system may be configured to display one or more body segments in 3D animation, such as torso, pelvis, upper arm, lower arm, hand segment, wrist, etc.

Embodiments of the invention may include a human motion monitoring system capable of computing and displaying anatomical metrics in real time from streaming sensor data during a training exercise.

Embodiments of the invention may include a human motion monitoring system capable of generating a biofeedback training exercise from one or more captured motions.

Embodiments of the invention may include a human motion monitoring system capable of storing historical motion data for biofeedback training repetitions to be accessed via the internet.

Embodiments of the invention may include a human motion monitoring system employing a drawing tool wherein a user may draw on top of generated 3D animations, graphs, etc. For example, the drawing tool may be used by coaches or trainers to highlight certain information such as by drawing lines, circles, images, or words that overlay the generated 3D animations and graphs. The generated 3D animations and graphs overlaid with such drawing may be saved and stored in database within a server, participant device, and or observer device to be accessed in the future.

Embodiments of the invention may include a human motion monitoring system that is configured to capture motion data in a manual mode (e.g., user presses a button to initiate capture of predefined duration) or in an automatic mode (e.g., ability for the system to automatically detect when a swing motion has occurred and then to store the motion data based on a recording of the event).

Other and various aspects, goals and objectives of the invention will be apparent from the examples and illustrations that follow. Pronouns should be interpreted in all cases to include both genders.

BRIEF DESCRIPTION OF THE DRAWINGS

The accompanying drawings constitute a part of this specification and illustrate an embodiment of the invention and together with the specification, explain the invention.

FIG. 4A is a top view of one sensor embodiment, mounted on a glove appliance.

FIG. 4B is a bottom edge view of the sensor of FIG. 4A, illustrating the attachment loops protruding from the curved underside of the sensor case, by which the sensor is attached to the glove appliance.

FIG. 4C is a side edge view of the sensor and glove appliance of FIG. 4A.

FIG. 46 is another screenshot of an Evaluation Report generated by the CPU for a golf activity according to an embodiment of the invention.

DETAILED DESCRIPTION

An athletic motion analysis system and method for improving performance according to various aspects of the present invention consists of equipment and methods, including cameras, inertial sensors, computers, computer networks, and software, means for providing real time visual feedback in unique formats and prescriptions for practice exercises, all as described in the following paragraphs. The invention comprises many embodiments and variations of which the following examples are illustrative and not limiting.

Figure 1:
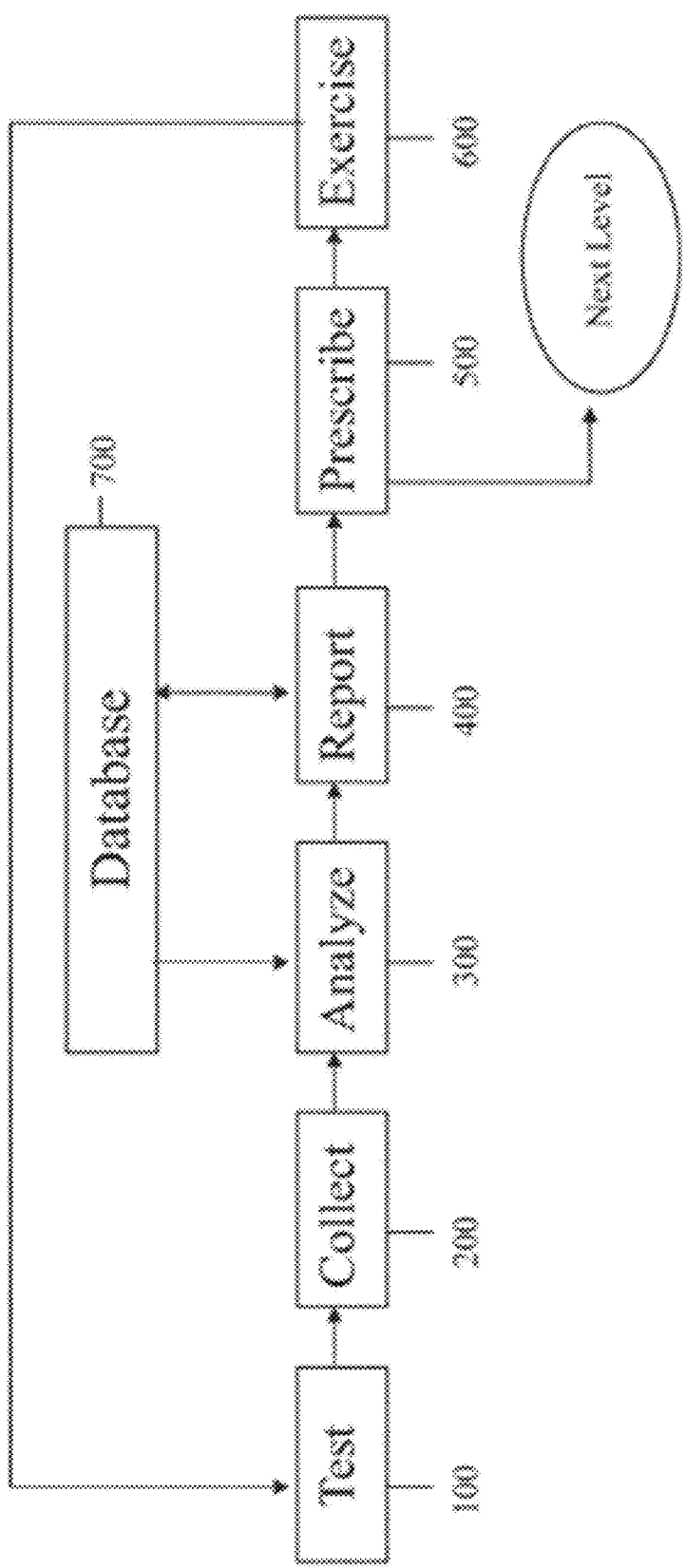
FIG. 1 is a simplified flow chart depicting the basic, repetitive, step-level methodology of the invention in which improvements in sequential performance testing are considered in the prescribing of the next sequential set of exercises.

Referring to FIG. 1, the steps of one embodiment of the invention are presented in sequence. Test 100 requires that the user subject him or herself to testing by use of the system of the invention while he/she conducts an athletic motion of interest. Collect 200 includes the measurement and collection of motion data with inertial sensors, a camera, and/or possibly other sensors, of the motion executed during the test. Analyze 300 includes analyzing the collected data, and includes accessing a database 700 of related data for comparison and for relating types and degrees of deviations in performance from benchmark values to a library of standard exercises for generating prescriptions of appropriate practice exercises or corrective measures. Report 400 includes the generation of a unique display of synchronized video, motion animation and data/time graphs. Prescribe 500 includes the documentation and delivery of a program or regime of type and time or quantity of performance parameter-specific exercises. Finally, exercise 600, instructs the user to practice the exercises or corrective measures in accordance with the prescription. The cycle of test, collection, analysis, report, prescription and exercise is repeated as often as desired until the desired level of performance is achieved. The type, time and level of the prescribed exercises are adjusted automatically (up or down) according to the most recent performance and/or the change in performance between the most recent performance test and prior reported test results.

Figure 2:
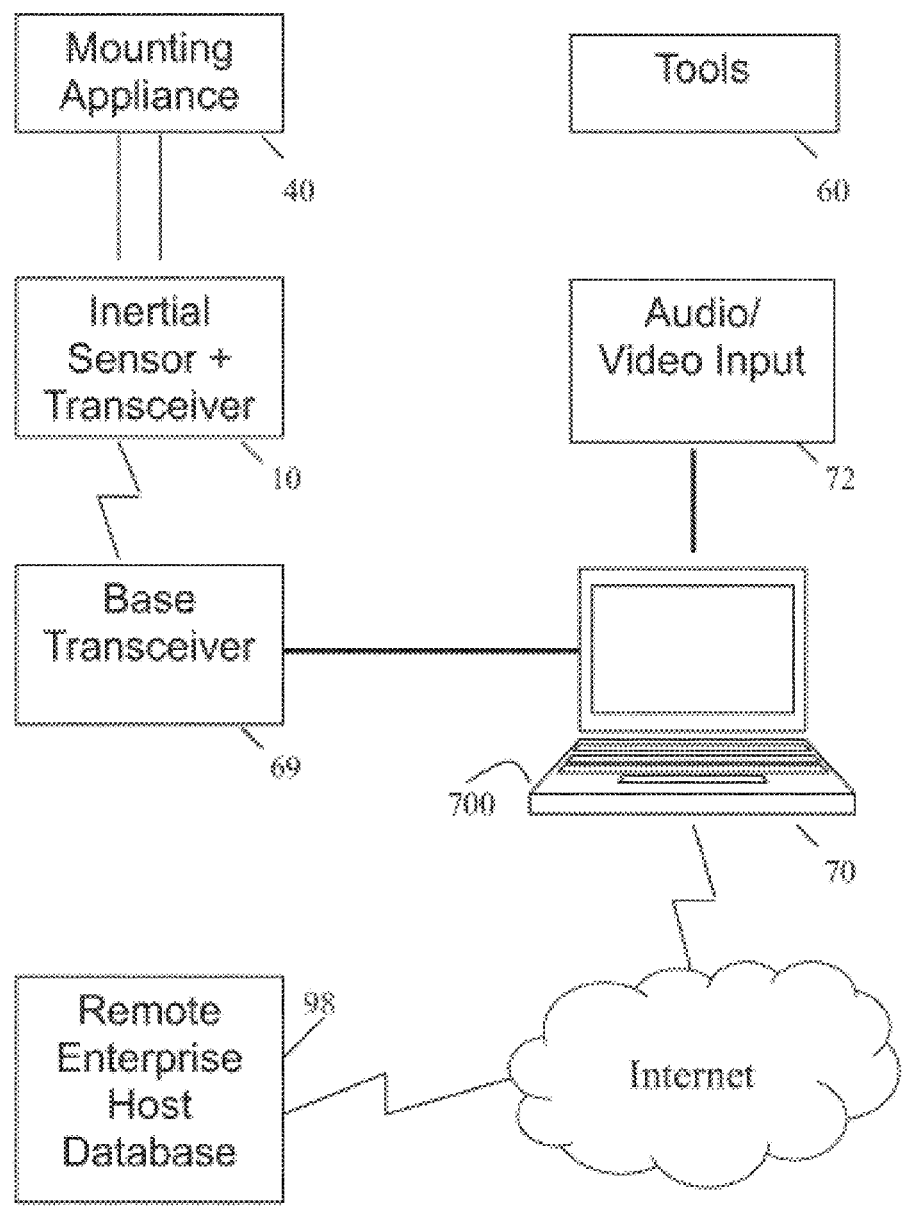
FIG. 2 is a diagrammatic illustration of the principle components of an embodiment of the invention, including the inertial sensor/transceiver, audio/video sensors, base transceiver, and computer with its control/display unit, and internet connection to an enterprise host and database.

Referring to FIG. 2, the principle components of one embodiment of the system and their relationship is represented in a system diagram where inertial sensors 10, attached to body appliances 40 that are worn by the user, communicate by wireless means with a base transceiver 69 which is part of a computer-based motion analysis system 70 that includes a control and display capability, such as a laptop computer, with suitable application software and an onboard or connected database 700. Other sensory devices 72, at least one video camera and optionally a microphone and other sensors, are connected to system 70 by wire or wireless means. System 70 processes motion data and generates, displays and/or transmits reports and prescriptions as described in more detail below. Training tools 60 are not directly linked to motion analysis system 70 or the other associated components, but may be used by the user during practice exercises as prescribed by the system after testing and analysis, all as is further explained below.

System 70 and its related components may be operated at times on a stand-alone basis, but may always or at times be connected or connectable to a remote, knowledge-based enterprise system and database 98 via a browser-based internet access point or other high speed data connection for conducting data transfer and enterprise related activities between the host and local systems.

For example, a website for the enterprise system and host database 98 may provide access for registered user systems 70 to the host company's information, motion analysis products and services information, management information, company news, user access via a log-in screen for product and service FAQs, newsletters, and database 700 libraries of past performance and benchmark data and exercises, and updates thereof.

The website may be configured to provide such global functionalities to registered users as general prescriptions and exercise instructions, explanations, and illustrations— text and/or audio/video, clubhouse events and news, discussion forums, special links for members, global FAQs, an on-line store link, special newsletters, and access to relevant documents and training tips. The website may be divided by categories of registered users pages as between student users and instructor users and provide such particular functionalities as either group might need, such as for instructors the history of instruction sessions by student portfolio, the history of student analysis by portfolio, with sessions organized or stored in respective student "locker rooms" by portfolio, and scheduling for student sessions. Student pages may provide such functionalities as the individual's own personal data, history of his sessions and analysis, his training calendar, instructor contact info, and his golf scores and stats logbook.

There may be a third class of user, an organization user such as a golf school or academy, where a subset of the enterprise system is treated as an OEM client or model, with its own branding, hosting multiple students and instructors as described above.

Individual systems of the invention work in stand-alone configurations as individual test and evaluation systems for collecting student performance data, analyzing and comparing student data to a library of performance data including expert performance data, reporting the results, and prescribing corrective exercises. New test results are added to the database, and may be delivered to or accessed by coaches and/or students via on-line access to internet services. Individual systems may share access to a host database of test results of other users and related practice drills for study or comparative purposes.

Alternate embodiments of the invention may be directed to other athletic, occupational, or rehabilitation motion analysis and training of animals or humans, at either an enterprise level or a local system level as described below.

Referring to FIGS. 3A, 3B, 3C, 4A, and 4C, various embodiments of body appliances for attaching motion sensors to the user's body and/or golf club are illustrated. The appliances are designed to be repeatably donned by the user such that the sensor assemblies are positioned and repeatedly repositioned in the same place on the body or club for optimal motion sensing at selected critical points of anatomy, particularly skeletal anatomy and/or tool structure, where they will provide motion data sufficient to define the initial position and full range of motion such that it can be reduced by data processing to the major component motions. The appliances are further refined structurally to minimize or avoid interference with body motion during execution of the movement under study. The appliances are yet further refined to retain body or tool position and to retain the relationship of the sensor assembly to the target area of the body or tool during normal body motion, including any strenuous flexing and/or acceleration associated with the motion under study, so that the change of position data reported by each sensor most accurately reflects the real time experience of the target area of the body and/or tool.

In one example, for a golf swing analysis system, there are a series of three appliances for mounting inertial sensors to the user's body. There is a vest appliance 40 (FIG. 3A) suitable for mounting an inertial sensor, referred to as a shoulder sensor, high on the user's back above and between the shoulder blades over the spinal column; a waist belt appliance 50 (FIG. 3B) for mounting an inertial sensor, referred to as a hip sensor, low on the user's back just above the hips and over the spinal column; and a glove appliance 58 (FIGS. 4A and 4C) for mounting an inertial sensor to the back side of the user's forehand. It is understood however that the sensors may be secured to the user's body or clothing via other mounting appliances or bands. Alternatively, the sensors may be secured directly to the user's body or clothing via conventional cellophane tape, double-sided tape, or a spray adhesive.

Figure 3A:
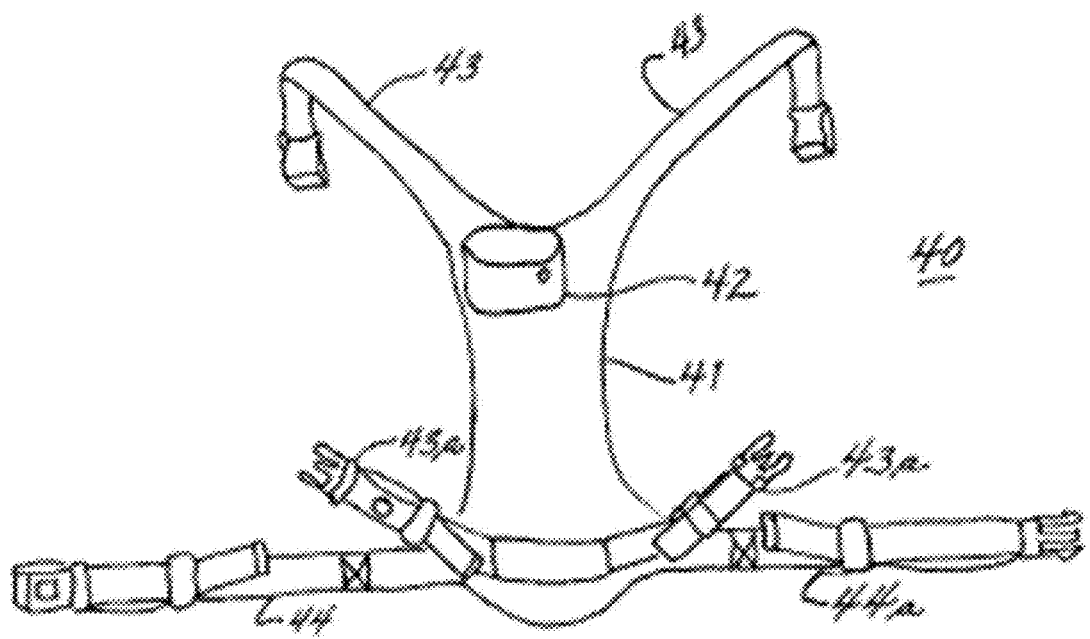
FIG. 3A is a diagrammatic backside elevation view of a vest appliance of the invention, illustrating the location of a sensor pocket high on the back panel.
Figure 3B:
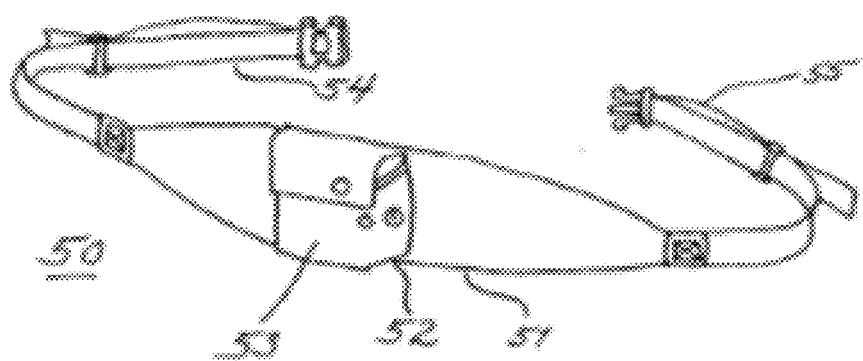
FIG. 3B is a diagrammatic perspective view of a waist belt appliance of the invention, illustrating the location of a sensor pocket on the back panel.
Figure 3C:
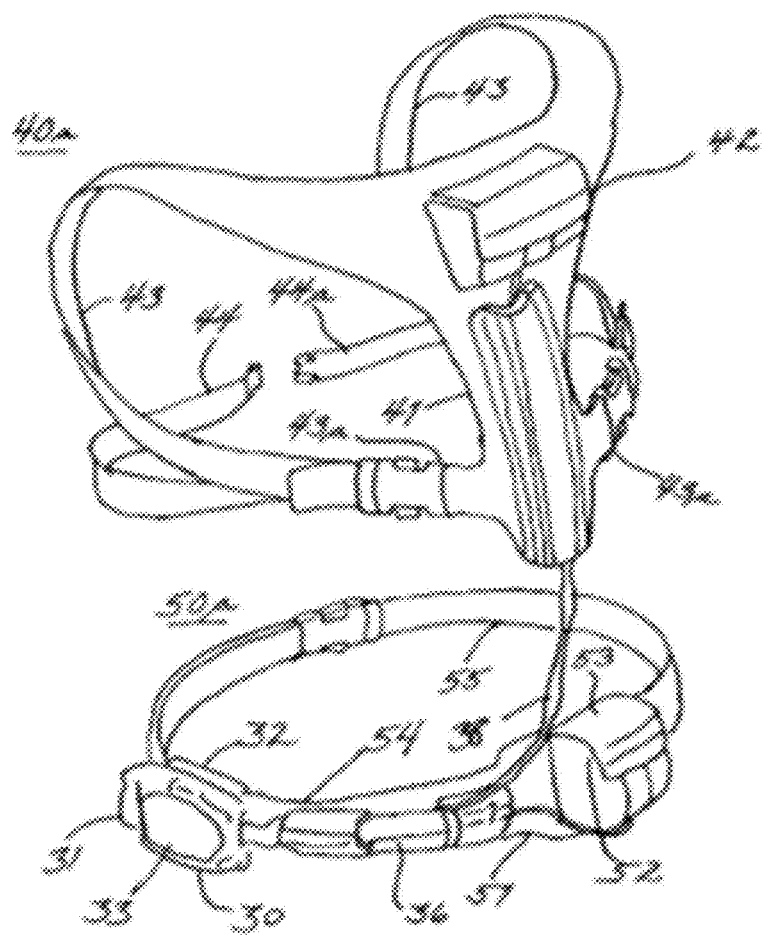
FIG. 3C is a diagrammatic perspective view of a vest appliance and a waist belt appliance configured with sensors in sensor pockets hard wired to a control module on the waist belt appliance, from which wireless transmissions of sensor data emanate.
Figure 4D:
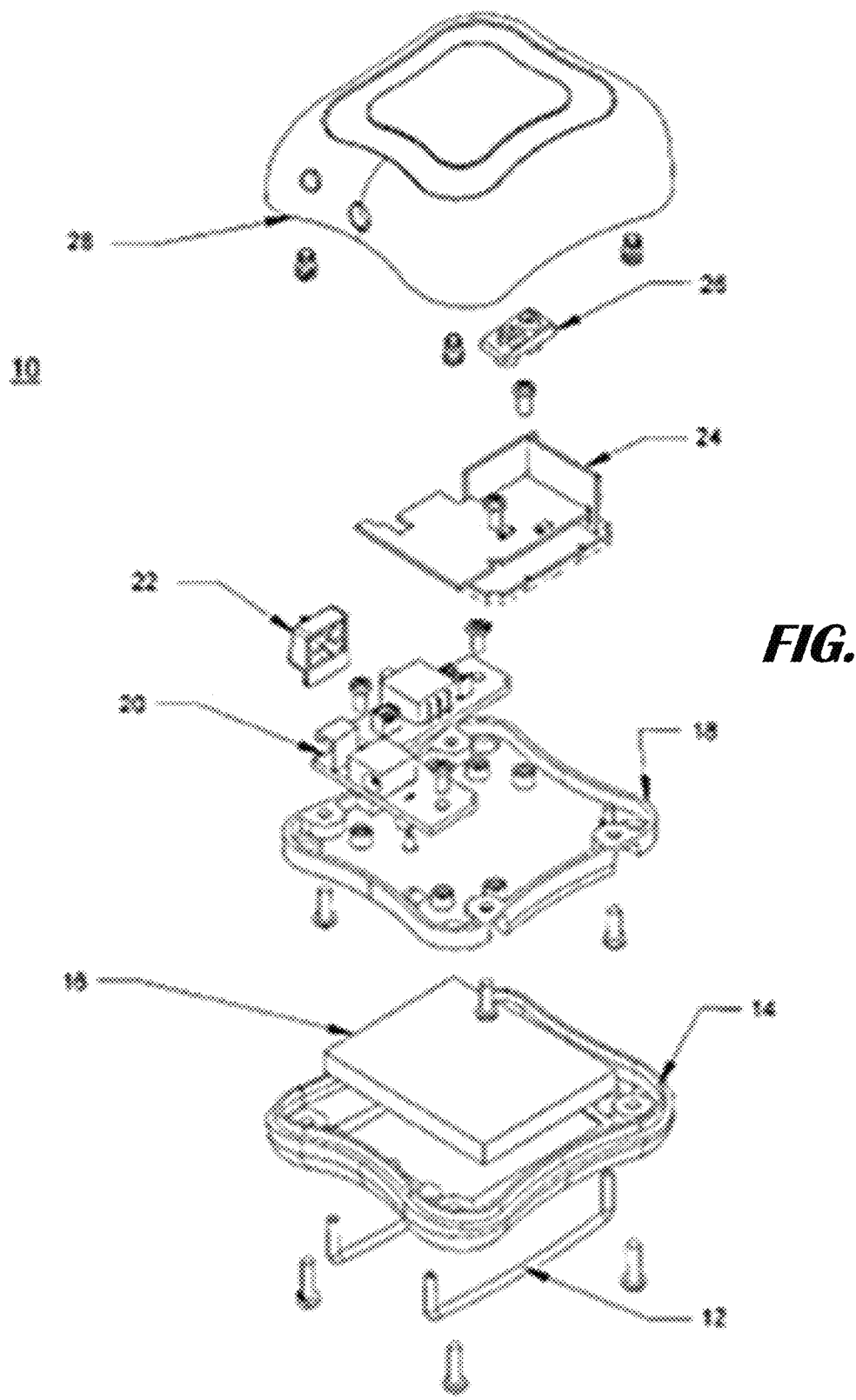
FIG. 4D is an exploded perspective view of the sensor of FIG. 4A, illustrating the stacked arrangement of electronic components over the curved battery, and the attachment loops protruding from the underside.
Figure 5:
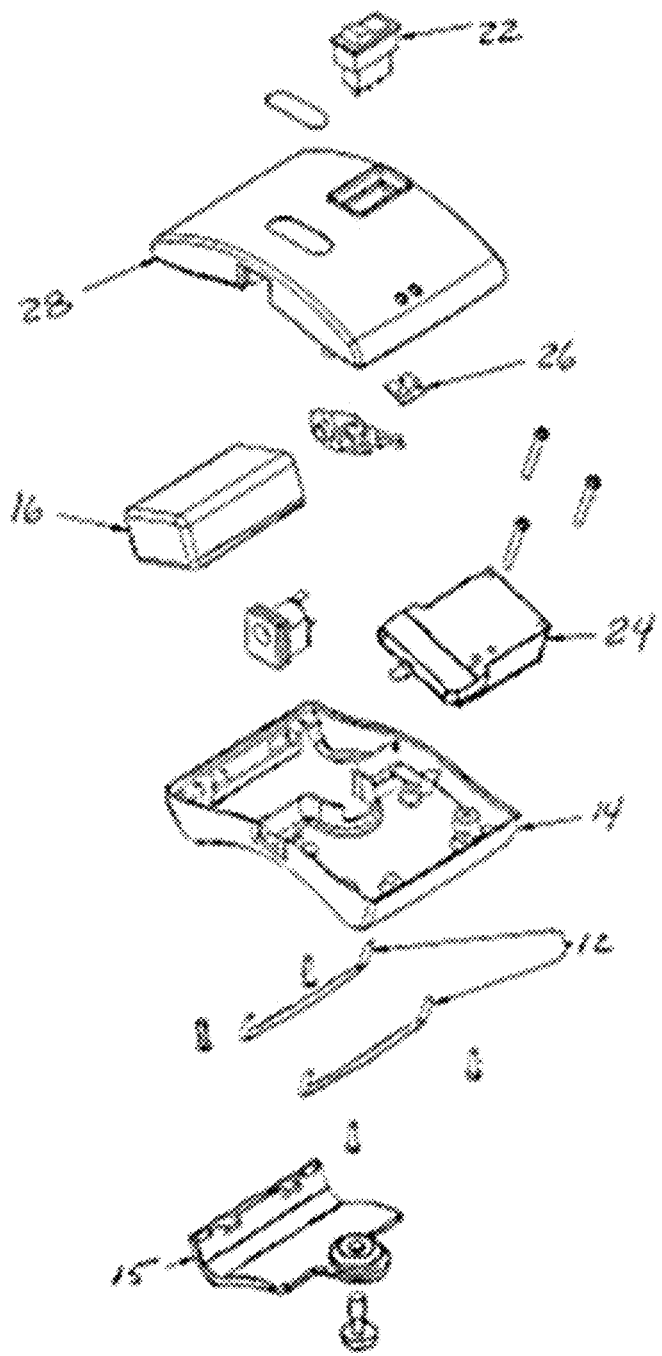
FIG. 5 is an exploded perspective view of another sensor embodiment, that may be wired to a control module-transmitter for transmission of sensor data.

Referring to FIGS. 3A and 3C, vest appliances 40 and 40A respectively have a back panel 41 at the top of which is attached a sensor pocket 42 suitable for snuggly securing a respective sensor 10 or 10A. Not visible in the figures but easily understood, the back side of the pocket that will receive the underside of the sensors of FIGS. 4B, 4D, and 5, is slotted to accept mounting loops 12 in a keying manner that enhances the grip and position integrity of the sensor within the pocket of the appliance.

The slots or sockets for receiving the sensor loops may be characterized as mounting structure, and may be further configured with latch mechanisms that secure the sensor loops 12 within the receiving slots or sockets of the sensor pocket with a mechanical interlock. Variations of the sensor loop structure as a mounting clip or stud and of the pocket slot as a keyed receiver structure, with a latching mechanism such as twist or click fit mechanism incorporated on either or both the appliance and the sensor are within the scope of the invention. The sensor pocket may be reduced in this instance to a mere location on the appliance rather than a full or partial enclosure for the sensor.

Shoulder straps 43 extending from the top corners of back panel 41 attach to strap ends 43A extending from the lower corners of the back panel via buckles. Chest belt sections 44 and 44a extend from the lower corners of the back panel for buckling on the front side of the wearer at about the level of the bottom of the rib cage or kidneys. All straps are adjustable in length for proper fitment to the wearer. The elongated back panel provides stability to the sensor from rotational displacement. The relatively high waist level of the chest strap provides security from vertical displacement of the sensor, and avoids interference with the waist belt appliance 50.

Referring to FIGS. 3B and 3C, waist belt appliances 50 and 50a, respectively, have a belt panel 51, the center section 52 of which is fabricated of non-stretch material, and is configured with a sensor pocket 53, with mounting loop slots as described above, sized and suitable for snuggly securing either a sensor 10 or 10A. Belt straps 54 and 55 extend from left and right ends of belt panel 51 and are buckled together at the front of the wearer.

Referring to FIGS. 4A, 4B, and 4C, glove appliance 58 is configured with a backside strap 59, the end of which is threaded through loops 12 (FIGS. 4D and 5) of sensor 10 and secured by hook and loop material or other commonly known fastener means to glove appliance 58. As with the other appliances, the loop and strap means of attachment may in the alternative be a hard mechanical interface between a suitable structure incorporated into the back of the glove appliance and a mating structure on the sensor.

Referring to FIGS. 4A, 4B, 4C, and 4D, and sensor 10 in particular, the packaging of the battery, sensor, transmitter, and the internal circuitry for data processing, transmission, and for recharging the battery, is uniquely designed to: (1) minimize the package size and weight; (2) place the center of mass as close as possible to the contact surface side of the sensor to minimize inertial forces tending to rotate or displace the sensor within its appliance relative to the intended target area of the user's body; and (3) to optimize the location of the sensing elements within the package to be as close to the center of the sensor's footprint as practical for best intuitive alignment of the sensor over the target area. To this end, the sensor uses a stacked configuration which places the relatively thin battery (the heaviest component and majority mass of the sensor) at the bottom closest to and conforming to the curved shape of the underside or user contact surface, with the circuit boards and sensing elements above it, only slightly further outboard from the user.

Each sensor has a unique identifier that is encoded within the output data stream, for unambiguous identity during multi-sensor operation. While not strictly necessary, in typical systems sensors are mounted in their appliances on the body with a consistent, pre-determined orientation or "up" end direction, simplifying the calibration and data processing.

Referring to FIG. 4D, one embodiment of a wireless inertial sensor 10 of the invention consists of an enclosure having a bottom cover 14 and a top cover 28, within which is housed a lithium battery 16, electronics shelf 18, printed circuit board 20 with switch, battery charger circuitry, on/off button 22, sensor assembly 24 which includes the transmitter, and light pipe 26. The lithium battery 16 conforms to the curved shape of bottom cover 14. It is readily apparent that the mass of battery 16, a substantial portion of the sensor mass, is distributed across and close to bottom cover 14. This stacking arrangement with the battery at the bottom provides a very low center of gravity for the sensor, improving its resistance to rotational or sliding displacement within the pocket of the appliance or on the back of the hand during body motion. The flat, relatively thin battery shape permits the inertial sensor to be outboard of the battery and the sensor package to remain relatively thin.

As described above, referring to FIGS. 4B, 4D and 5, mounting loops 12 extend from bottom cover 14 and provide for mounting stability in two respects. Sensor pockets 43 and 53 (FIGS. 3A, 3B, and 3C) in vest and waist belt appliances are configured with slots (not shown but readily understood from this description) that receive mounting loops 12, providing a keying effect for proper insertion and positioning of the sensors within the pockets.

Referring to FIG. 5, this embodiment sensor is a wired inertial sensor 10A and consists of an enclosure having components analogous to those of sensor 10 (FIG. 4D), but the enclosure shape and configuration of components is adapted to use a conventional 9 volt battery positioned at one edge of the enclosure, accessible through battery door 15, rather than the stacked order of assembly of sensor 10.

Figure 6:
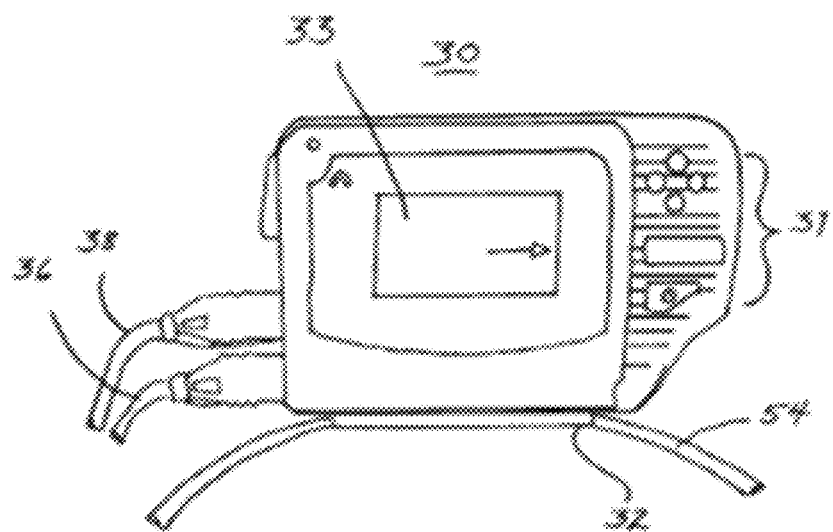
FIG. 6 is a front face view of a control module to which body sensors may be wired for wireless transmission to a receiver/computer system and/or local display of selected parameters of motion.

Referring to FIGS. 3C and 6, there is in one embodiment of the motion analysis system a control module 30 wired to sensors in sensor pocket 42 and 52 via cables 38 and 36 for receiving motion data. It has a hinged attachment 32 to belt 54 so that controls 31 and display 33 are easily viewable by the user. There is internal data processing capability and display driver for providing information directly to the user, and an integral wireless transmitter or transceiver for transmitting data to a motion analysis system 70 (FIG. 2), and/or receiving setup or other data or instructions from the motion analysis system.

Control module 30 is configured with a battery pack, hip sensor input, shoulder sensor input, microcomputer, keypad, LCD display, USB connection, remote sensor and system transceiver capability, and optionally with a video game interface.

Figure 7:
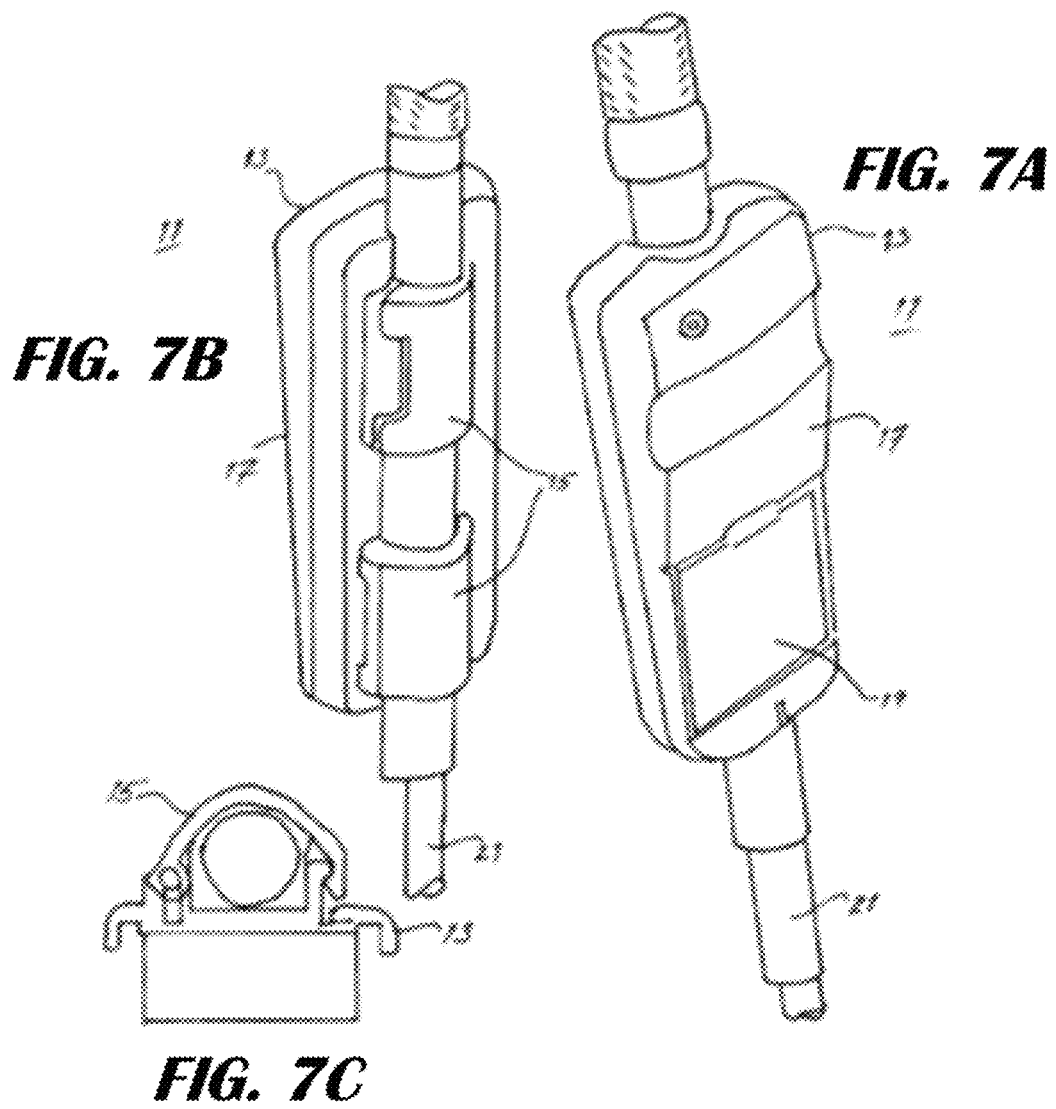
FIG. 7A is a front perspective view of a golf club sensor assembly, attached to the shaft of a gulf club.
FIG. 7B is a backside perspective view of the golf club sensor assembly of FIG. 7A.
FIG. 7C is a cross section view of the golf club sensor of FIG. 7A.

Referring to FIGS. 7A, 7B and 7C, there may in addition or in the alternative to the body worn appliances, a mounting appliance attachable to the tool or in this case golf club, for mounting a sensor. Alternatively, the mounting means may be incorporated into the sensor enclosure as in wireless club sensor 11, where the back cover 13 incorporates a latch mechanism 15 for securing sensor 11 to the shaft 21 of a golf club. Top cover 17 encloses the battery at its lower end, accessible via battery door 19, while the electronic circuitry and sensor elements are contained in the upper section closer to the grip of the club.

Figure 8:
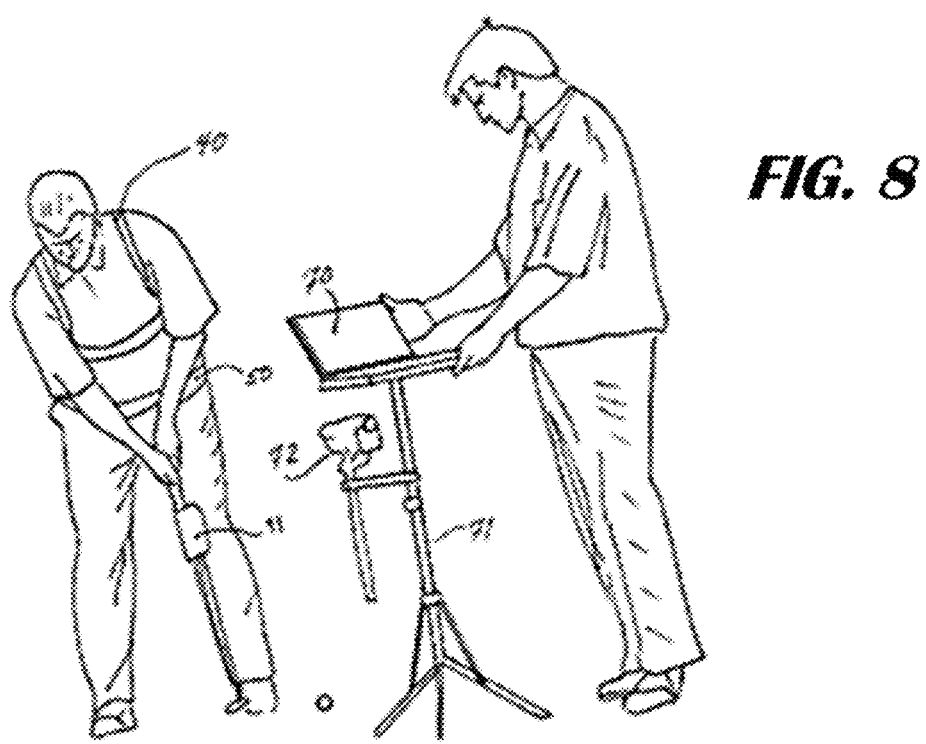
FIG. 8 is an illustration of one embodiment of the system and method of the invention in use, consisting of a golfer wearing vest and waist belt appliances mounted with inertial sensors and holding a golf club with an inertial sensor mounted just below the grip of the club, standing adjacent to a stand supporting a video camera directed at the golfer and an associated receiver and processing computer with keyboard and display, the display being viewed by an instructor.

Referring now to FIG. 8, there is illustrated of one embodiment of the system and method of the invention in use, consisting of a golfer wearing vest appliance 40 and waist belt appliance 50 which are each equipped with a wireless inertial sensor as described above. The golfer is holding a golf club with an inertial sensor 11 mounted just below the grip of the club, standing adjacent to a stand 71 supporting a video camera 72 directed at the golfer and an associated receiver and processing computer system 70 with keyboard and display, the display being viewed by an instructor.

The camera positions and direction with respect to the golfer's position, size and posture are carefully aligned with respect to the test site from one or the other or both of at least two positions: a first camera position at a specific down line angle, height, and lateral position or offset, and another camera position for face on angle, including height and offset. Correct camera positioning enables placement of an overlay in the video display that includes vertical and horizontal alignment lines representing center of alignment and center of balance. There may be multiple cameras on additional stands oriented to capture the motion from different directions and different heights and offsets, and some or all may be positioned carefully to support the further use of overlays of alignment lines relating to the golfer's position, size, posture, and expected motions, so as to make motions and deviations in alignment very apparent in subsequent video presentations of the swing motion.

Stated more generally, prior to testing, it may be required to select and define a test site to have at least one motion reference point; to then position the video camera to be directed at the test site at a pre-defined angle of rotation around the point or test site, a specific height relative to the reference point, with a specific angle of elevation and lateral offset with respect to the reference point. Thereafter a video test signal of the test site and reference point is sent to the computer-driven display screen and an overlay is inserted onto the computer-driven display screen corresponding to the reference point, from which specific motions are more easily observed.

The processing computer or PC of system 70 performs relational calculations on the parameters received from the various sensors, thereby allowing computation of various golf-related parameters of interest. As an example, the PC can calculate club-face angle or the angle through which the golfer turns his or her shoulders while swinging the golf club. Such parameters are referred to here as performance or alternatively diagnostic parameters, to distinguish them from the rate or position parameters transmitted by the sensors to the PC.

In a golf swing motion analysis system in particular, rate and position motion data are typically processed by the application software into performance or diagnostic parameters relating to the golfer's body segment performance, including: hip velocity (degrees per second); hip rotation (degrees negative and positive); shoulder velocity (degrees per second); shoulder rotation (degrees negative and positive); club release (degrees per second); club speed (miles per hour); club face rotation (degrees open/closed); club path (degrees inside or outside of club's address position); hip linear movement (centimeters left or right of neutral address); hip and shoulder separation (time difference between maximum hip, shoulder, and club velocity); flexion/extension of hip segment (centimeters traveled along z-axis); and kinetic link. These parameters are further extrapolated to yield a predicted resulting "ball in flight" performance of parameters: spin (degrees per second); launch angle (degrees); carry distance; roll distance (yards); total distance (yards); distance traveled off line (yards right or left); ball flight character (fade, draw, hook, slice, push, pull, straight); and PTI or power transfer index.

This processed information is reported to the golfer in a unique, synchronized, multi-format presentation of the swing motion that is available in real time and/or playback mode for optimal user and instructor assimilation.

Figure 9:
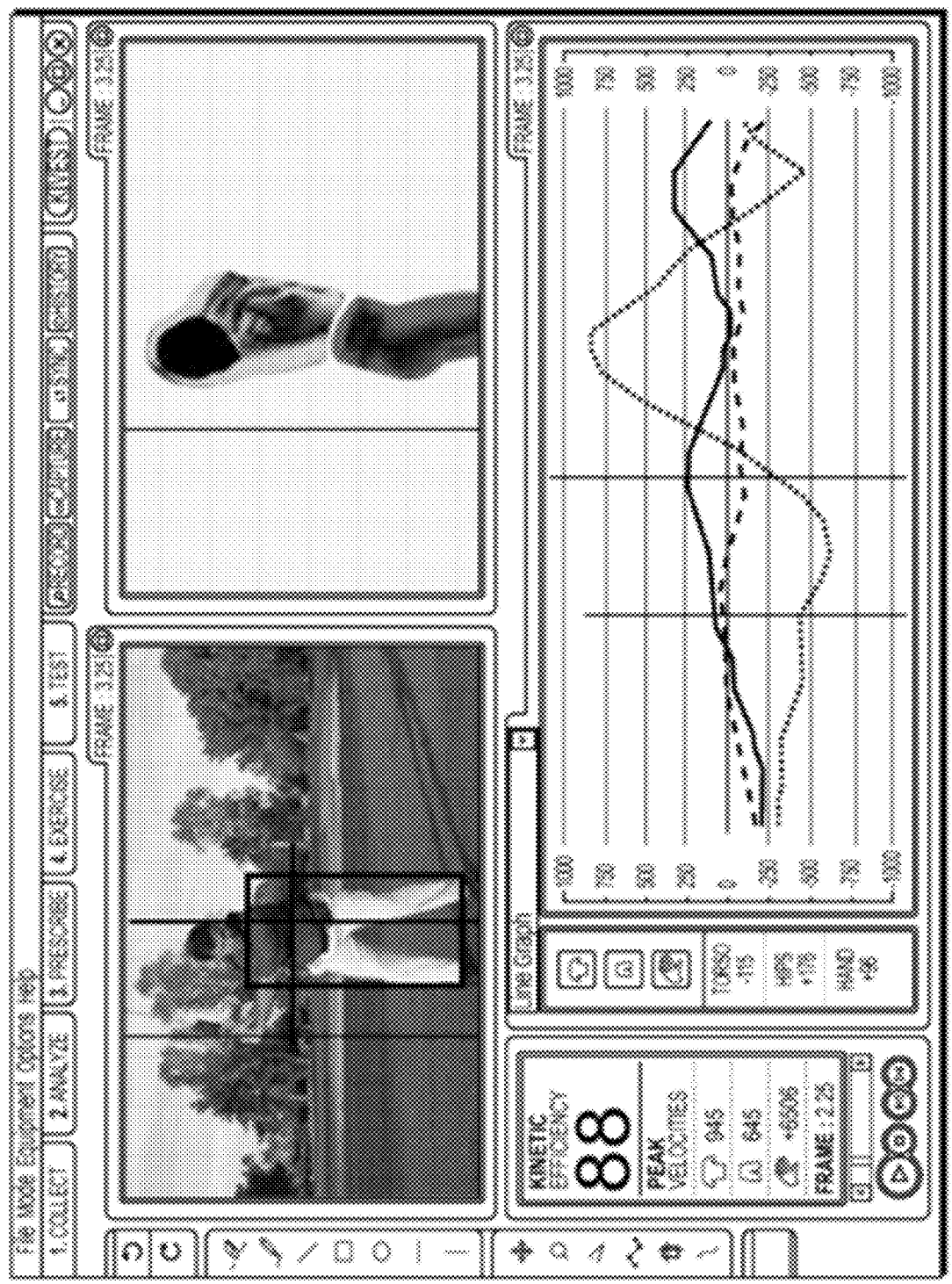
FIG. 9 is a screen shot of the composite display of the invention, incorporating three formats of feedback: a live video feed of the golfer in the upper left portion of the display, an animation of the golfer in the upper right portion of the display that is color coded to distinguish major body segments; and in the lower portion of the display a motion data time line graph tracing hip, shoulder and hand motions in a multi-colored trace.

FIG. 9 is a screen shot of the synchronized, composite display of the invention, incorporating three formats or forms of feedback. In a real time feedback or "biofeedback" mode, there is a live video feed of the golfer, typically a face on or side view, presented in the upper left portion of the display although it may be placed elsewhere in the display, in which the alignment lines are applied during a set up phase, are stationary and the motion with respect to the alignment lines is readily apparent.

A multi-color animation of the golfer, generated from the inertial sensor motion data, is presented in the upper right portion of the display, although it may be positioned elsewhere in the display. The animation may be color coded to distinguish major body segments, e.g. the shoulders segment versus the hips segment. The animation may be oriented to view the swing motion from any useful angle, depending on what aspect or component of the swing motion is being scrutinized at the time.

In the lower portion of the display a motion data time line graph traces hip, shoulder and hand motions in a multi-colored trace, although it may be positioned elsewhere in the display. The graph may present simply the component motion data from the instant swing motion, and demonstrate graphically the coordination between hips, shoulders and hand motion; or it may present a comparative trace of the present motion or component of motion compared to a prior motion or an expert motion in order to illustrate the degree of deviation and required improvement to achieve a desired performance level.

Figure 10A:
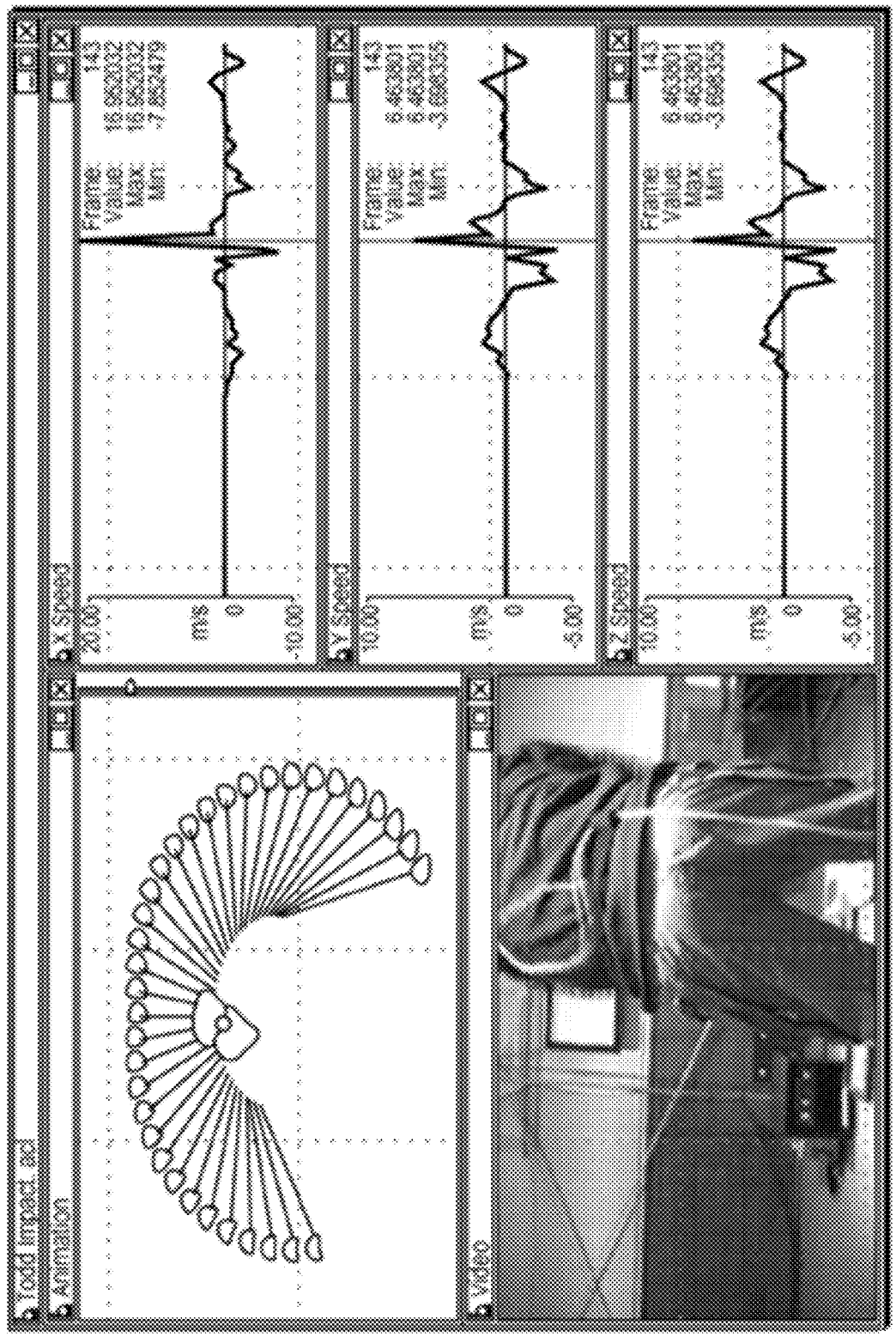
FIG. 10A is a screen shot of a composite display of the invention, incorporating three formats of feedback: a live video feed of the golfer in the lower left side portion of the display; a time-stepped animation of the club swing indicating the plane of the club swing and the hand orientation during a swing motion; and three motion data time line graphs showing the club speed in three axis.

Referring to FIG. 10A, another example of the composite, multi-format, synchronized display is a screen shot of a composite display of the invention, incorporating the three formats of feedback of FIG. 9: a video record of the golfer this time in the lower left side portion of the display; a stepped frame animation of the club swing indicating the plane of the club swing and the hand orientation during a swing motion; and three motion data time line graphs showing the club speed in three axis.

The stepped frame animation is a useful device for illustrating the plane, path or arc of a motion or component of motion, and is a further enhancement of the presentation. Selected positions of a point or object or portion of the video screen are retained as the video progresses so as to show the path leading up to the present position. The stepped aspect of the presentation can be done as function of time, or of linear or angular displacement of the object or point of interest, whichever better serves to illustrate the path of motion best for the viewer.

Stated more generally, the multi-color, three dimensional animation representing the motion of at least one color-coded body segment created from motion data may include or be in some embodiments a stepped frame animation where selected positions of an object in motion are retained in subsequent frames of the animation such that a motion track of the object is apparent to a viewer. The retained positions may be programmed to be selected on the basis of time, position, speed, or acceleration of the object in motion.

The orientation on the screen of these multiple forms of simultaneous presentation may be varied. There may be additional information as well, space permitting. A composite presentation of video, animation, and motion data graphs enhances the user's ability to quickly assimilate and appreciate the subtle differences at the component level of the swing motion, between his current performance and the desired performance. A multi-dimensional presentation of the swing performance can be watched in real time, in an instant replay mode, or in a later review.

Figure 10B:
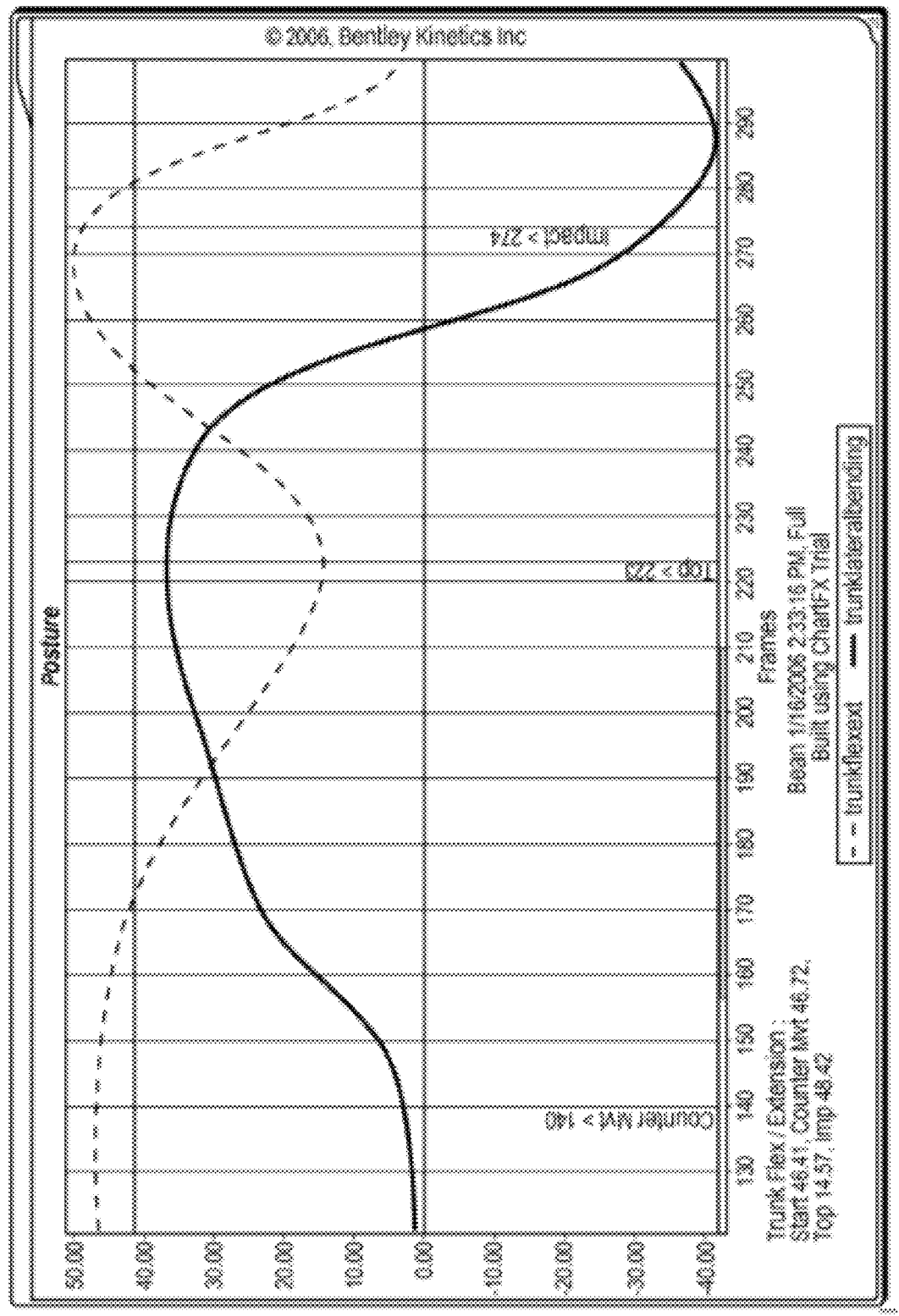
FIG. 10B is a line graph indicating posture with respect to trunk flex extension and trunk lateral bending versus time during a swing motion.
Figure 10C:
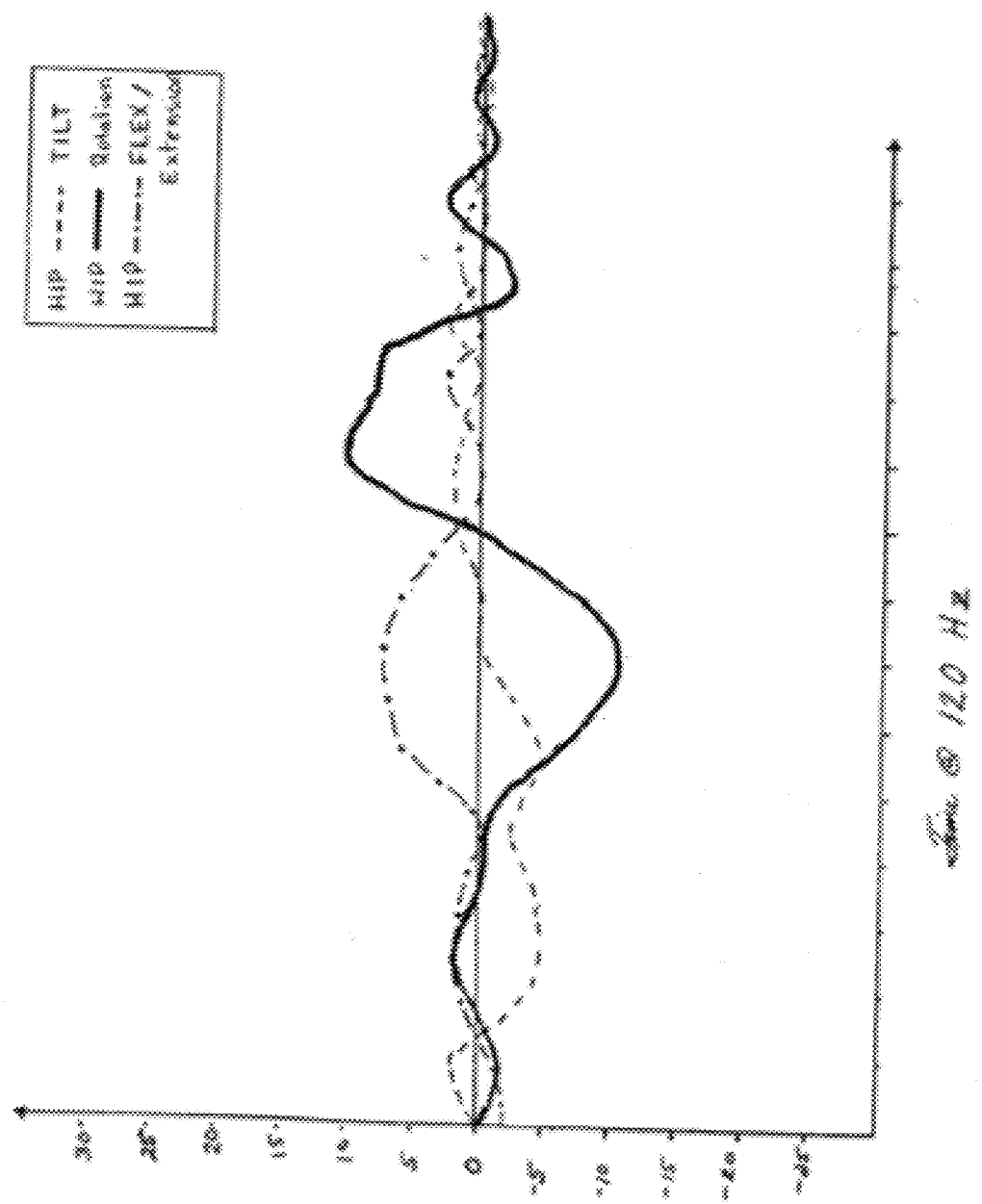
FIG. 10C is a line graph indicating degree of pivot during a swing motion.
Figure 10D:
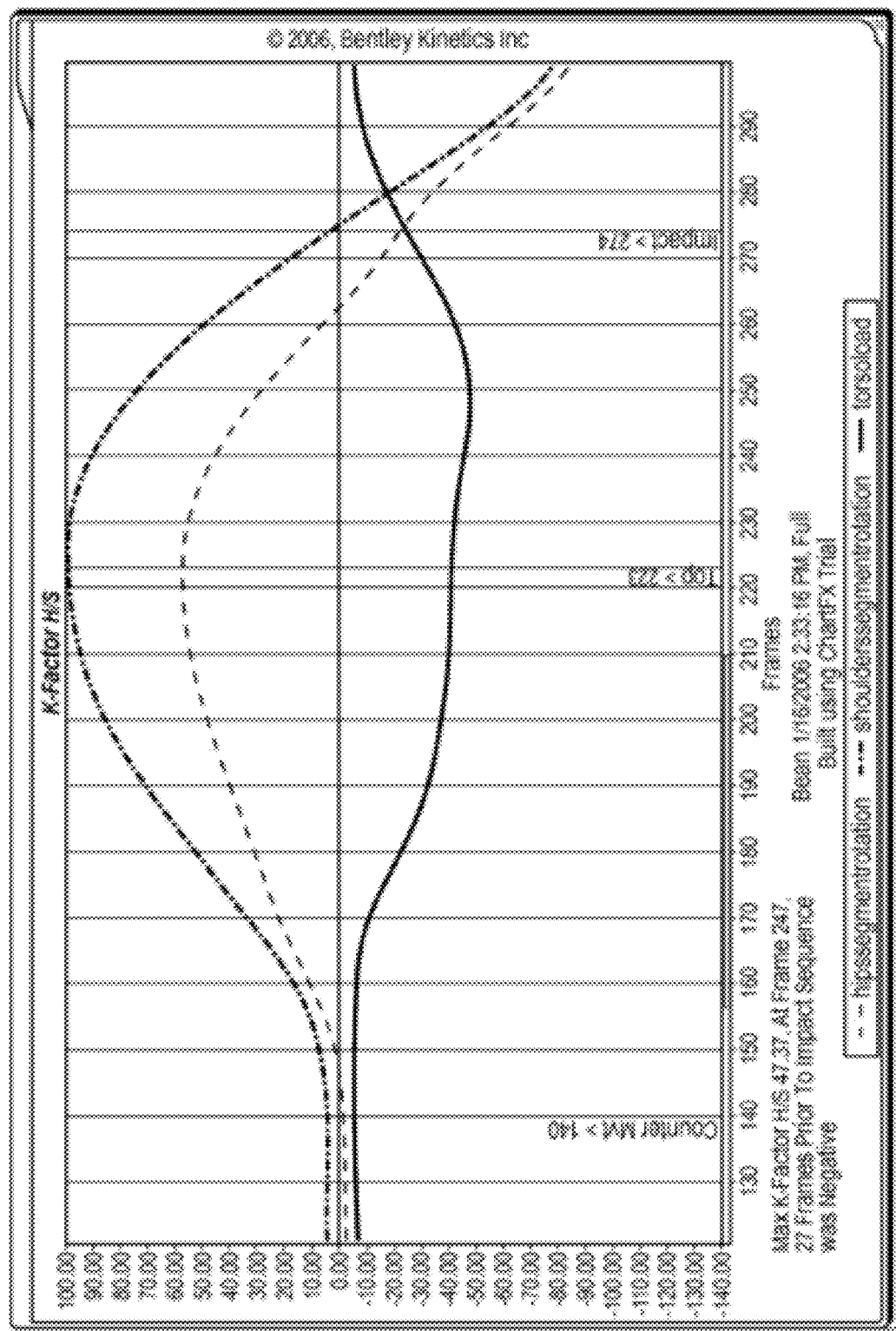
FIG. 10D is a line graph indicating degrees of hip segment rotation, shoulder segment rotation, and torso load during a swing motion.
Figure 10E:
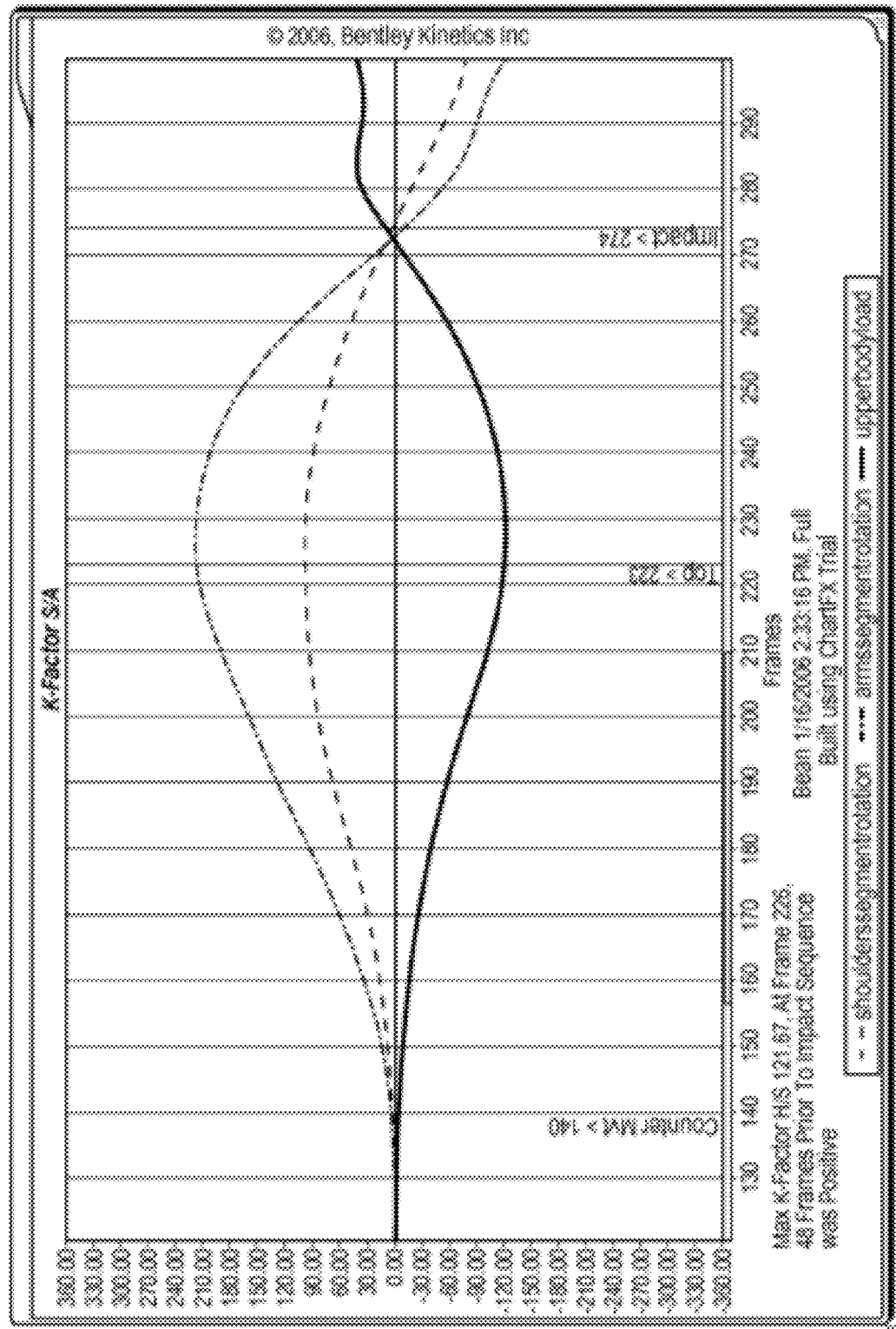
FIG. 10E is a line graph indicating degrees of shoulder segment rotation, arm segment rotation, and upper body load during a swing motion.
Figure 10F:
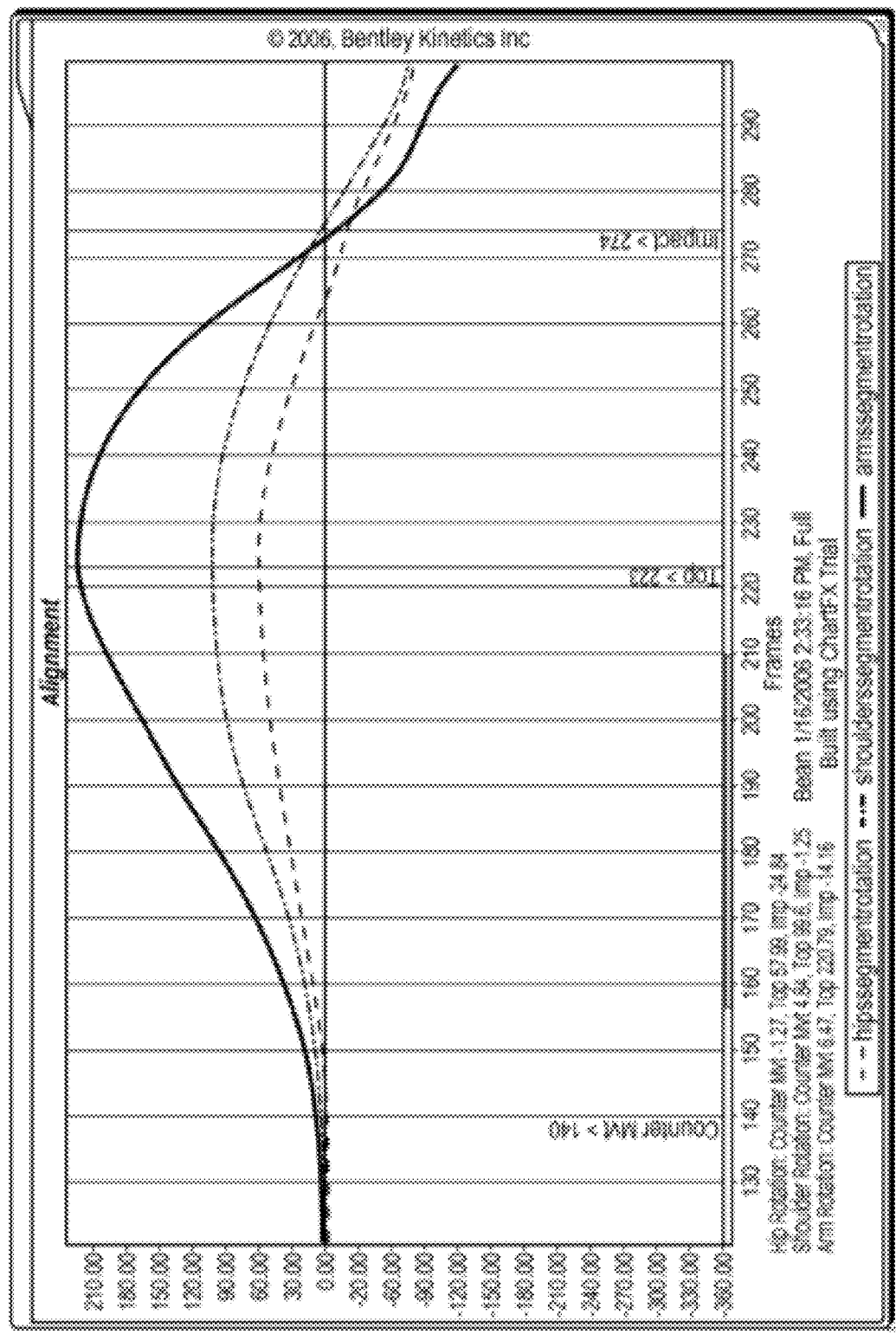
FIG. 10F is a line graph indicating alignment of hip segment rotation, shoulder segment rotation, arm segment rotation versus time during a swing motion.
Figure 10G:
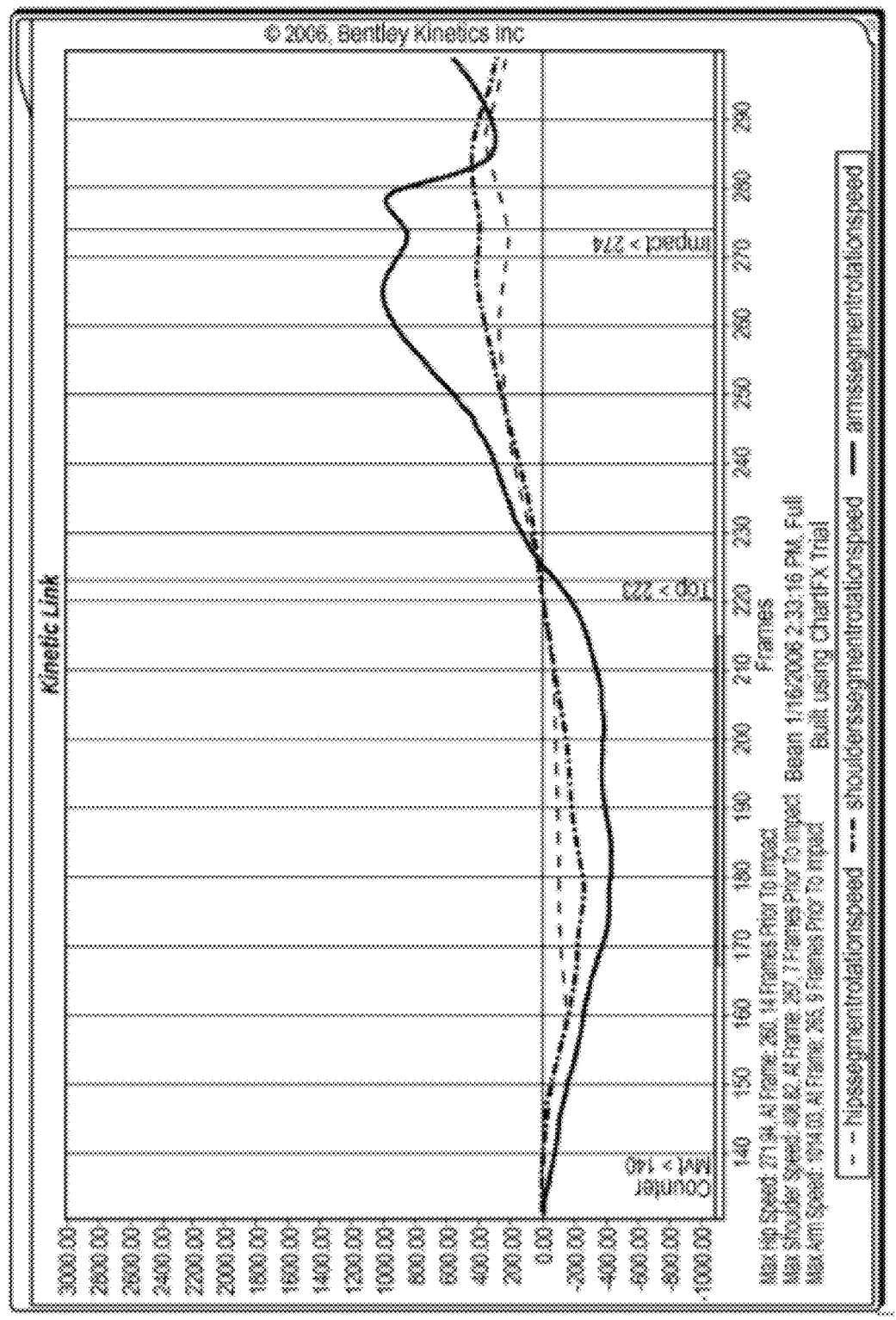
FIG. 10G is a line graph indicating hip segment rotation speed, shoulder segment rotation speed, and arm segment rotation speed during a swing motion.

The system 70 also offers alternative and supplemental forms of presentation or "report" of the swing performance. Expanded graphs, for example, help clarify the timing of components of motion, as well as the amplitude. For example FIG. 10B is a line graph indicating posture with respect to trunk flex extension and trunk lateral bending versus time during a swing motion. FIG. 10C is a line graph indicating degree of pivot during a swing motion. FIG. 10D is a line graph indicating degrees of hip segment rotation, shoulder segment rotation, and torso load during a swing motion. FIG. 10E is a line graph indicating degrees of shoulder segment rotation, arm segment rotation, and upper body load during a swing motion. FIG. 10F is a line graph indicating alignment or coordination of hip segment rotation, shoulder segment rotation, arm segment rotation motions versus time during a swing motion. FIG. 10G is a line graph indicating hip segment rotation speed, shoulder segment rotation speed, and arm segment rotation speed during a swing motion.

Figure 11:
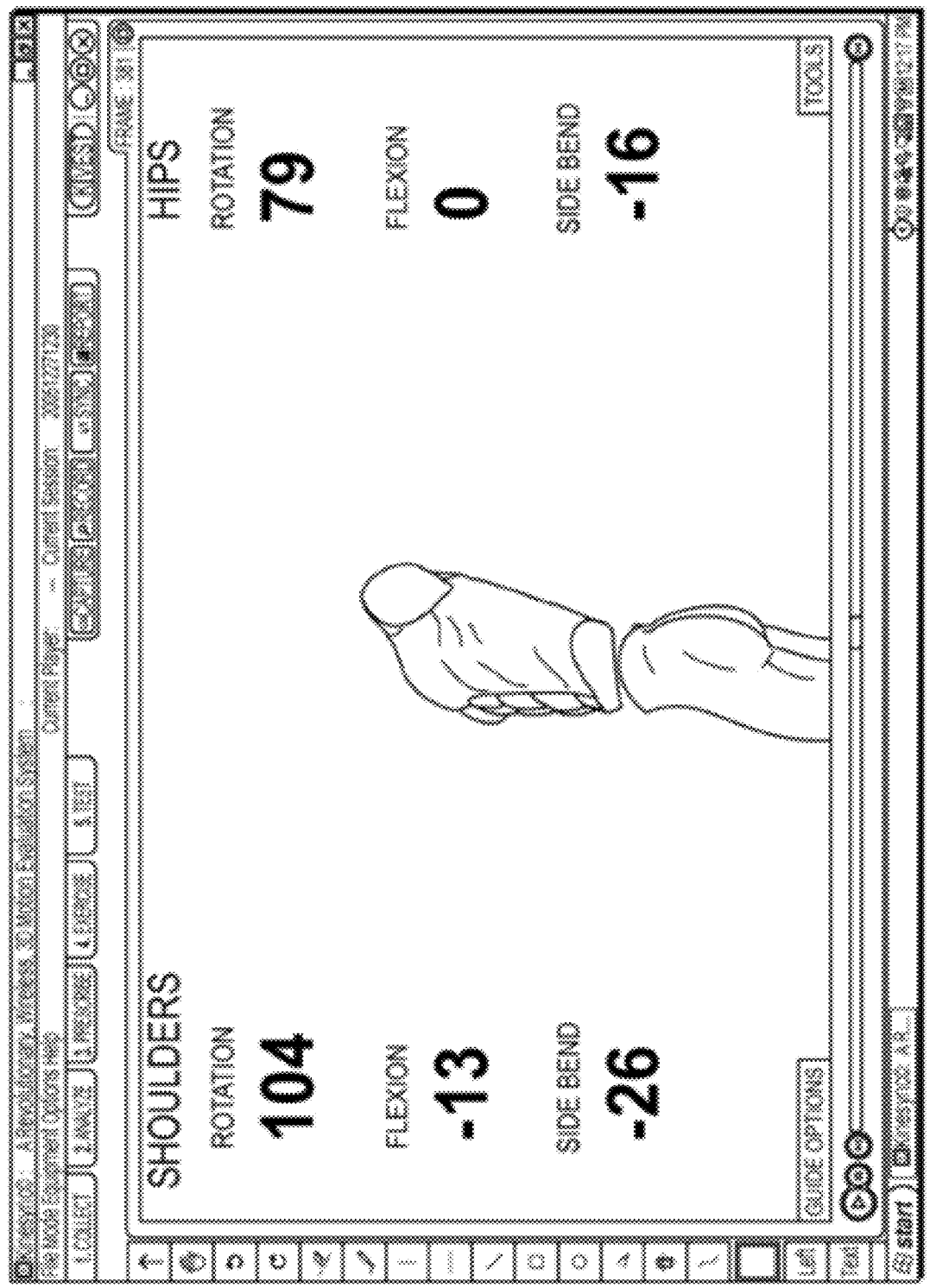
FIG. 11 is a screen shot of the multi-color animation illustrating the color distinction between the shoulder segment and the hips segment of the animation.

The animation capability of the system, driven by the inertial sensor inputs, offers additional opportunities for presenting more detailed illustrations of the swing motion in real time or playback mode. For example, FIG. 11 is a screen shot of a multi-color animation illustrating the color distinction between the shoulder segment and the hips segment of the animation. This makes for easy and quick distinction between these components of the full swing motion. The numerical value of peak or range of rotation, flexion, and side bend are posted left and right of the animation for calibrating the user's perspective of the animation motion.

Figure 12:
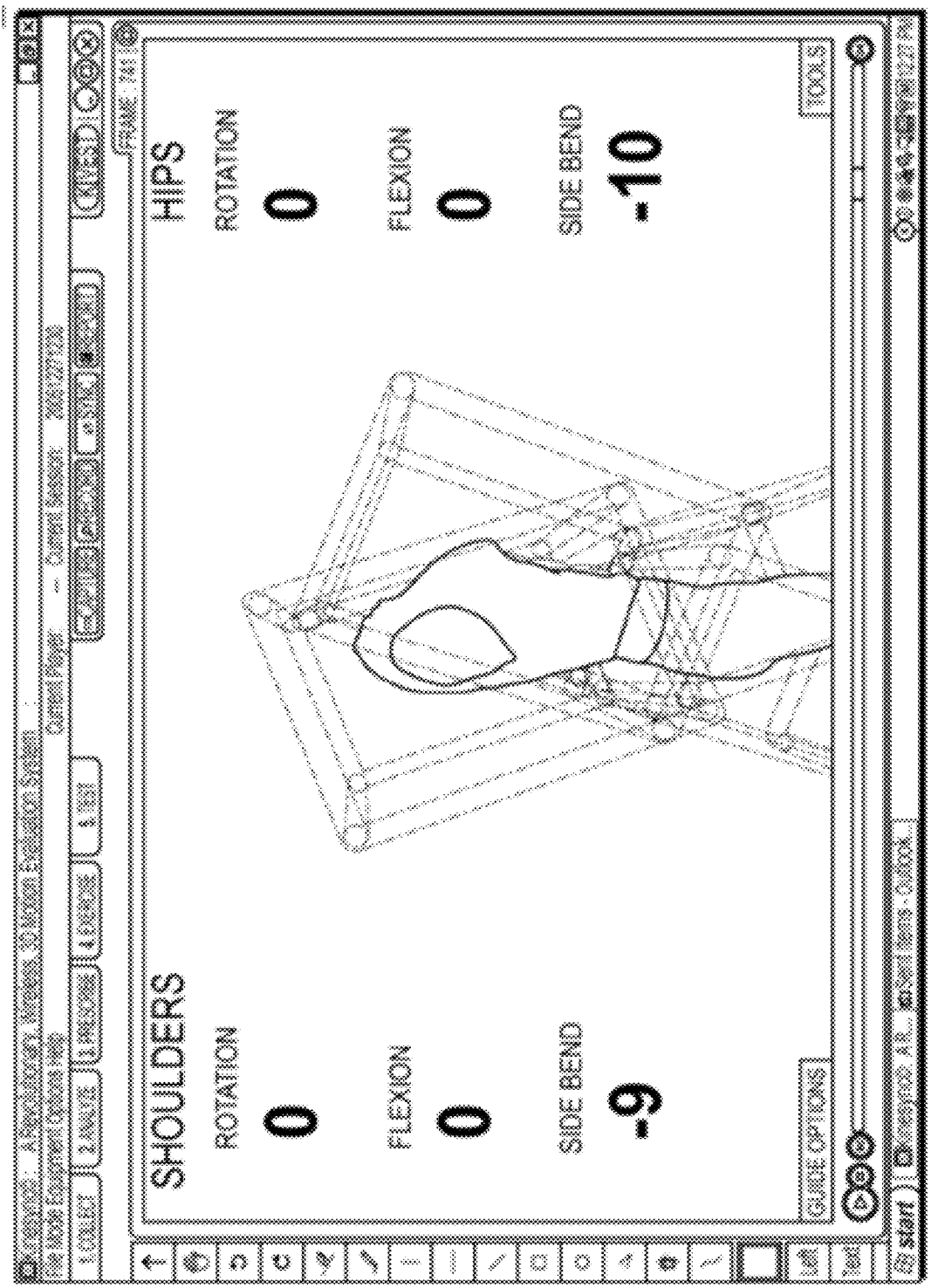
FIG. 12 is a screen shot of a multi-color animation illustrating the cage by which user settable parameters for lateral bending during swing motion are made apparent to the golfer as real-time feedback.

The animation capability provides yet a further training tool in the form of animated "cages" or scalable limits of selected parameters that cage the animated figure and illustrate the golfer's movement within the three dimensional frame. FIG. 12 is a screen shot of a multi-color animation illustrating the box or cage by which user settable parameters for lateral bending during swing motion are made apparent to the golfer for real time feedback. The processing computer 70 can create an instantly apparent change to the display, for example by turning the background orange for close calls and red for actual violation of the cage parameters during a swing motion.

Figure 13:
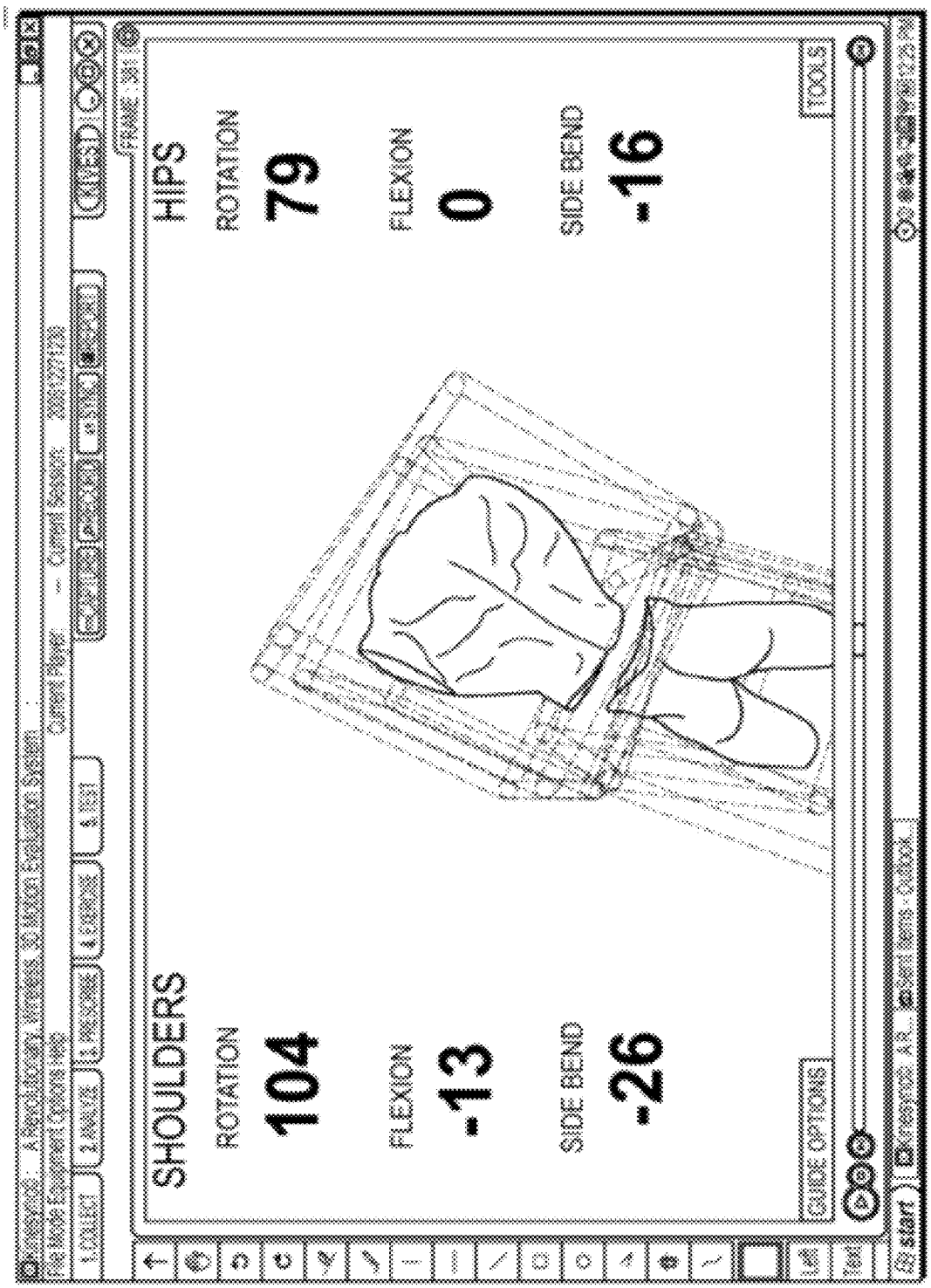
FIG. 13 is a screen shot of a multi-color animation illustrating the cage by which user-settable parameters for flexing during the swing motion are made apparent to the golfer as real-time feedback.
Figure 14:
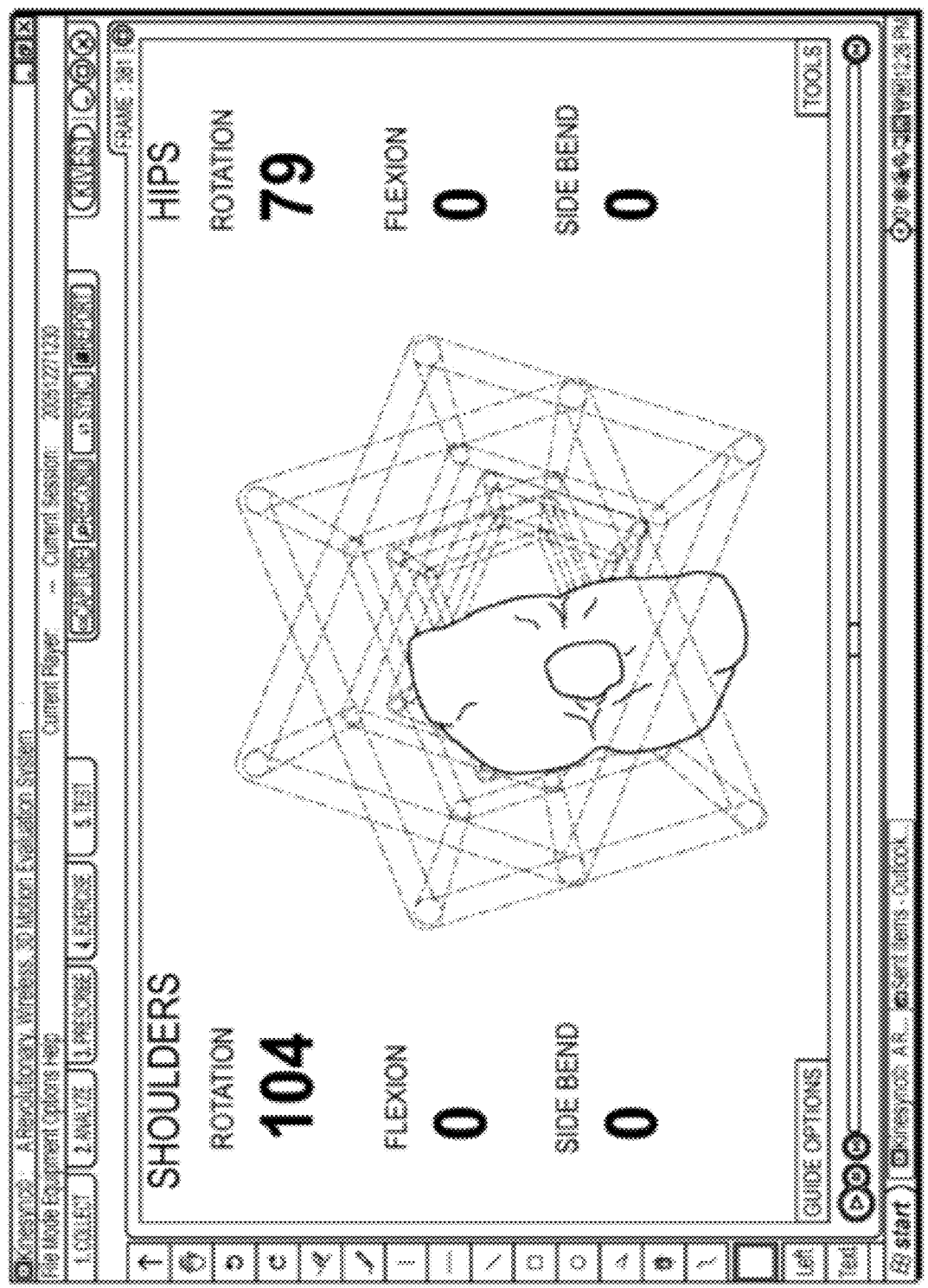
FIG. 14 is a screen shot of a multi-color animation illustrating the cage by which user-settable parameters for rotation during the swing motion are made apparent to the golfer as real-time feedback.

Further examples of the power of motion data animation as part or all of the presentation or "report" part of the methodology follow. FIG. 13 is a screen shot of a multi-color animation illustrating the three dimensional grid or open frame by which user-settable parameters for flexing during the swing motion are made apparent to the golfer as real-time feedback. FIG. 14 is a screen shot of a multi-color animation illustrating the "box" by which user-settable parameters for rotation.

Figure 15:
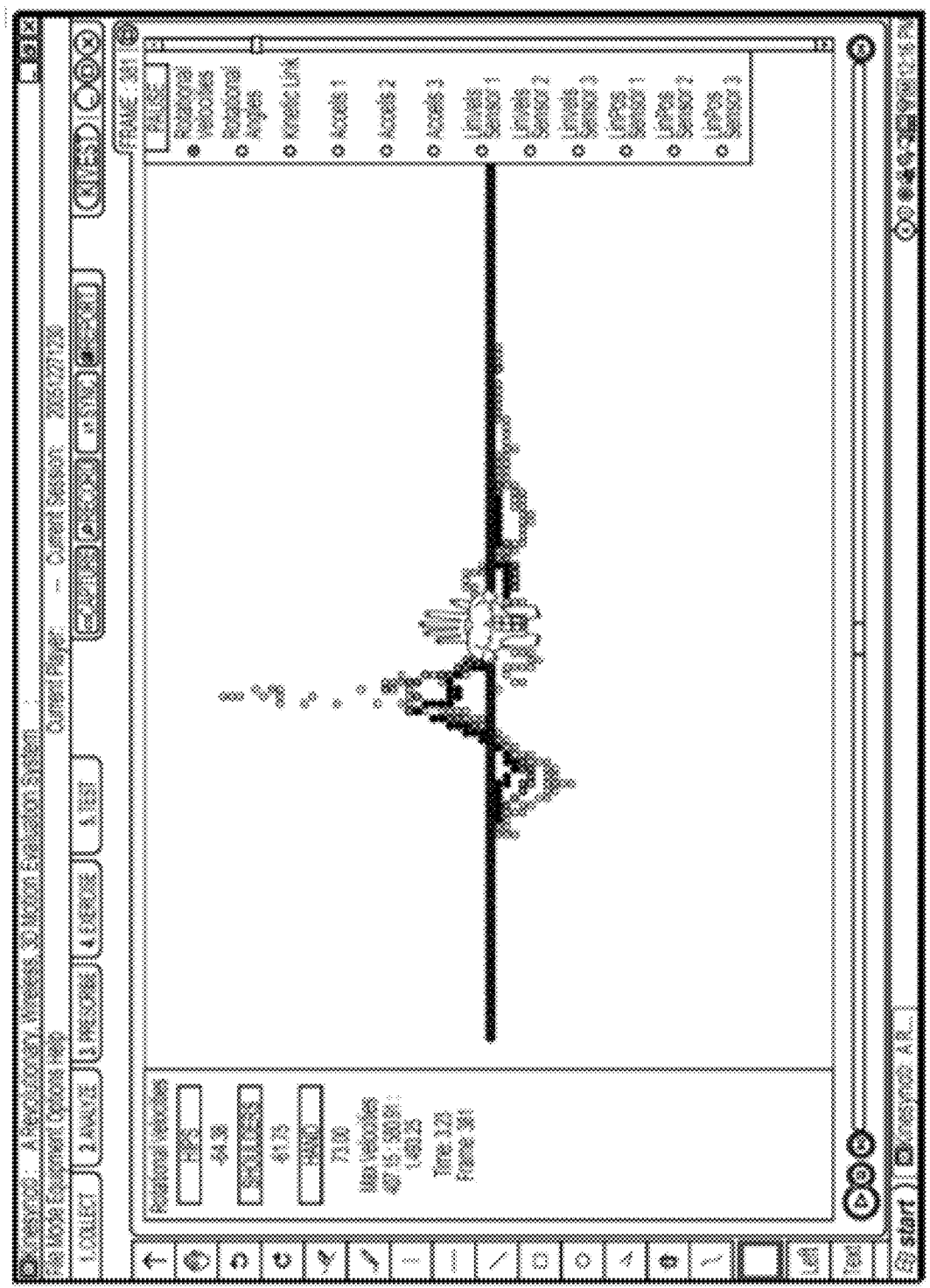
FIG. 15 is a screen shot of a multi-color line graph illustrating the coordination in time and amplitude of the rotational velocities of the hips, shoulders, and hand of the golfer during the swing motion.

The animation capability of the system can also be used to present an enhanced version of the time line traces or graphs. FIG. 15 is a screen shot of a multi-color line graph illustrating the coordination in time and amplitude of the rotational velocities of the hips, shoulders, and hand of the golfer during the swing motion.

It should be noted that although FIGS. 11 through 15 are illustrated here as full screen shots; these and other animations of the motion data and settable parameters are within the scope of the invention and can be presented in the multi-format form of FIG. 9, with synchronized video and graphs.

It is a goal of the invention to provide an objective, consistent analysis of each performance. The methodology of the invention depends on capturing motion data, processing it into the described parameters relating to body segments and components of the motion, providing a quantitative analysis of each component of motion, and then summing the scores for each component of motion so as to produce a unitary number or "kinetic index" for the performance as a whole. One embodiment of a system 70 for golf swing motion analysis processes motion data against benchmark values to produce a value on a uniform index scale of 0-50 for each of the following primary performance parameters: sequence, speed, stability, mobility, transfer, timing, club performance, and club accuracy. These values are summed in a pre-determined order to arrive at a unitary number representing the kinetic index for the total performance on a scale of 0-100, as described further below.

Objectivity and repeatability of the system for motion analysis depends on a consistent process that examines and gives weighted consideration of all relevant aspects of the motion in calculating a final performance factor or kinetic index.

Figure 16:
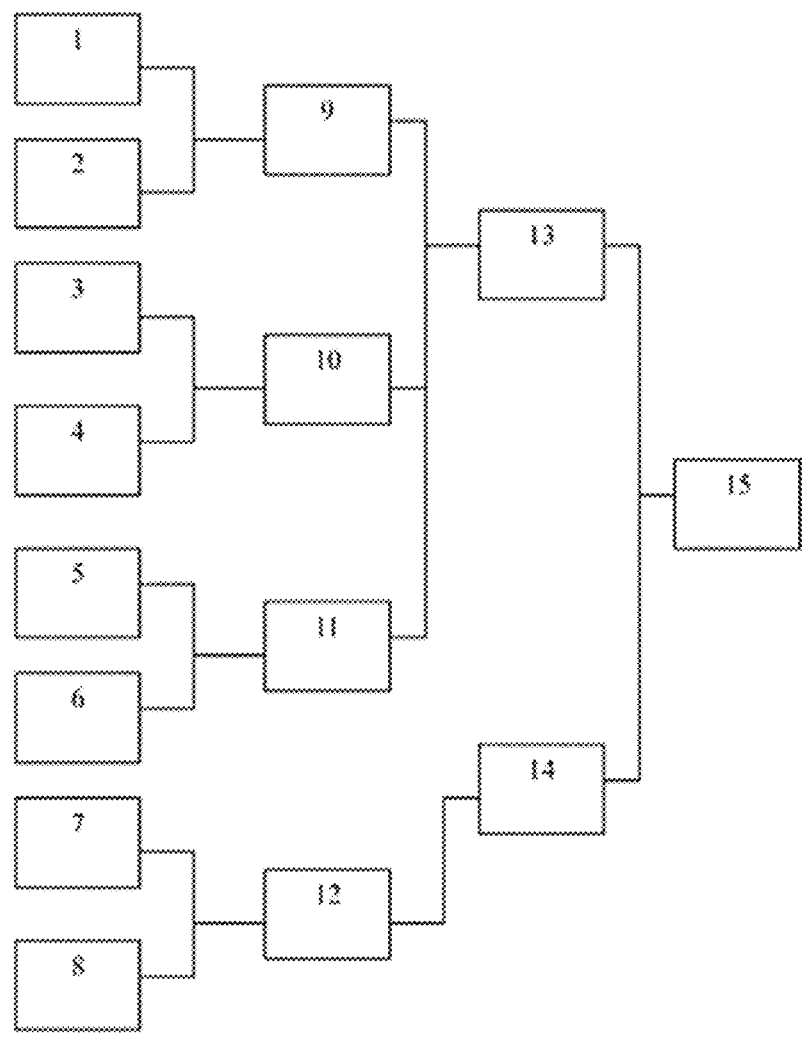
FIG. 16 is a simplified representation of a multi-step process for the reduction of multiple primary performance parameters to a fewer number of secondary performance parameters, hence to respective body and club performance factors, and finally to a single kinetic index reflecting an objective evaluation of the total performance of a swing motion.

Referring now to FIG. 16, one aspect of the methodology of this embodiment is illustrated in an objective, repeatable, computer-automated reduction of the basic or primary performance parameters 1-8 measured by system 70 against pre-selected benchmark values, into a single kinetic index. The system uses a multi-step process that sums the primary parameters into secondary parameters 9-12, then into body performance factor 13 and club performance factor 14, and finally merges these values into kinetic index 15, a quantification of the overall performance value of the swing motion being analyzed.

The FIG. 16 performance parameters are explained below:

Primary Parameters:

1. Sequence:

This parameter relates to the degree of timing and coordination of the rotational velocities of hips, shoulders and arms during the swing motion. For example, at 120 frames per second, the target or benchmark standard sequence for a golf swing motion is assumed to have maximum hip rotation velocity occur at 36 frames before maximum shoulder rotation; which should occur at 24 frames ahead of maximum arm rotation; which should occur at 16 frames ahead of the club impact on the ball. The total deviation in frame count from the pre-established or assumed ideal sequence for all segments is inversely weighted against a total maximum score or ideal performance index for the sequence parameter of 50, yielding a relatively lower score for respectively larger deviations.

2. Speed:

This parameter relates to the maximum peak rotational velocity of each body segment. The benchmark is set at: 400 degrees/second for hip rotation; 800 degrees/second for shoulders rotation; 1600 degrees/second for arms rotation; and 3200 degrees/second for club rotation. The sum of the differences is weighted inversely against a maximum score of 50, yielding a relatively lower score for respectively larger differences.

3. Stability:

This parameter relates to the orientation of the hip segment and shoulder segment in relation to the spine. It is measured in degrees. The benchmark for hips, shoulders, and arms are all 0 (zero). Again, the sum of the differences is weighted inversely and scaled against a maximum index of 50.

4. Mobility:

This parameter relates to the relative range of angular rotation of hips, shoulders, arms around the spine. The benchmark is that they be equal. The sum of the differences are weighted inversely and scaled against a maximum index of 50.

5. Transfer:

This parameter relates to the sum of the ratio of angular momentum of the hips to the shoulders, and hence to the arms. The measured transfer ratio is scaled against a benchmark maximum ratio of 6 and equated to a maximum index of 50. For example, using benchmark values, if 400 degrees/second of hip rotation produces 800 degrees/second for shoulders rotation, that is a transfer ratio of 800/400=2.0. Then if 800 degrees/second shoulders rotation results in 1600 degrees/second for arms rotation, and 3200 degrees/second for club rotation, then those transfer ratios are also 2.0 and 2.0 respectively; the sum of which is 6.0. A lesser actual score is divided by 6 and multiplied by 50 to generate a base-50 index score.

6. Timing:

This parameter relates to the difference in time or coordination of maximum rotational velocities of hips, shoulders, and arms in time. The scoring is based on the delta or difference in timing in the manner described above, scaled against a maximum index of 50.

7. Club Performance:

This parameter relates to the linear acceleration of the club, added to peak angular release velocity. The benchmark is 300 mph (miles per hour) for linear acceleration and 400 degrees/second of angular velocity. The simple sum, 700, is equated to a maximum performance index of 50, and the measured value scored accordingly.

8. Club Accuracy:

This parameter relates to the three dimensional movement of the club on the ball and is graded on the velocity of the straight-on axis less the velocities in each of the orthogonal axis, in miles per hour. The total is compared to a benchmark and the result scaled to a maximum performance index of 50.

Second Order Parameters

The primary parameter scores 1-8 are reduced in a first step by a simple summing of related parameters as follows:

9. Sequence & Speed:

the sum of the individual indexes of sequence 1 and speed 2 above, having a maximum index of 100.

10. Stability & Mobility:

the sum of parameters 3 and 4 as above.

11. Transfer & Timing:

the sum of parameters 5 and 6 as above.

12. Club Power Accuracy:

the sum of club performance 7 and club accuracy 8 indexes.

These second order parameters are further reduced to a body performance factor 13 and a club performance factor 14 as follows:

13. Body Performance Factor:

the sum of parameters 9, 10, and 11 divided by 3, having a maximum index of 100.

14. Club Performance Factor:

simply the club power accuracy 12 index brought forward.

The body and club performance factors 13 and 14 are summed and divided by 2 to yield the:

15. Kinetic Efficiency Index:

having a scale of 0 to maximum 100.

It will be appreciated that the pre-selected benchmark values of the individual parameters are somewhat arbitrary, selected to provide a performance challenge to the anticipated range of skills of a target pool of users. The use of other or alternative benchmark values and scoring formulas is within the scope of the invention. Also, the selection and ratio or weight giving to each performance parameter in the reduction process is somewhat arbitrary, the requirement being that each parameter is given a weight or degree of consideration recognized to be relevant to the overall performance.

The reduction process of primary performance parameters into a final kinetic index in the context of a golf swing analysis reflects the kinetic chain philosophy, that the performance value of the total motion is the sum of the performance value of the component parts of the motion executed in an optimal sequence, in order to transfer maximum energy and accuracy from feet to hips to shoulders to arms to the club and ultimately to the ball.

While this description of motion analysis and performance measurement has been cast in the context of a golf swing; the apparatus and methodology is equally applicable to other athletic motions involving, for example, running and kicking leg motions and swinging or chopping hand and arm motions.

Having evaluated individual performance parameters, which may also be referred to as "diagnostic" parameters, the system is able to compare the performance results to a catalog of exercises appropriate to the respective parameters and their test result, and provide an automated recommendation or prescription of exercises. The system may be further preprogrammed with the user's available training schedule and hence able to tailor the prescription to the training time available, with emphasis on the parameters most in need of improvement. In other words, referring back to FIG. 1, the invention extends the automated, objective, Report on performance to include a Prescription for improvement.

In this regard, performance parameters are also characterized as diagnostic parameters. In the golf swing context, they may relate to subsets, body segments or components of the motion including: feet, hip; and shoulder performance. For example, diagnostic parameters of CBL (center balance line) extension and flexion, and of CAL (center alignment line) left and right lateral bending, relate to feet performance. Exercises appropriate to CBL extension problems are scaled according to a pre-determined scheme to the severity or priority of the problem, on a scale of 0 (acceptable performance) to −20 degrees (significantly below acceptable performance). A rating of −5 degrees may generate a prescribed exercise called "posture stick", using particular training tools; a relatively lower rating of −10 may call for the same exercise but with a different training tool; and so on. The "posture stick" exercise, for example, requires manipulation of a club in a prescribed manner while standing on a base platform, to acquire and practice attaining a stance with the correct alignment of the major joint centers of the body for creating an optimal muscle length tension relationship to enhance the body's postural equilibrium. Other exercises are similarly focused on particular body segments and components of the golf swing.

The initial selection of exercises and tools and the pre-determined scheme for allocation of particular exercises for improving particular performance parameters is somewhat arbitrary, but calculated to induce improvements in performance of components of motion and hence to the total motion performance if practiced as prescribed. The following table 1 lists one embodiment of diagnostic parameters and appropriate exercises by priority by which prescriptions would be issued by the system to a user.

TABLE 1

Diagnostic Parameters and Exercises
Relating to Components of Motion

| Subject Area | Test/Measurement Parameter | Deviation (degrees) | Prescribed Exercise/Tool |
|---|---|---|---|
| Feet Posture #1 | Center Balance Line Extension | 0 | No Drill |
| | | −5 | Posture Stick/K-Pillow & club |
| | | −10 | Posture Stick/Full Foam Roller & club |
| | | −15 | Posture Stick/Half Foam Roller & club |
| | | −20 | Posture Stick/Base Platform & club |
| | Center Balance Line Flexion | 0 | No Drill |
| | | 5 | Posture Stick/K- Pillow & club |
| | | 10 | Posture Stick/Full Foam Roller & club |
| | | 15 | Posture Stick/Half Foam Roller & club |
| | | 20 | Posture Stick/Base Platform & club |
| Feet Posture #2 | Center Align. Line, Left Lat. Bend. | 0 | No Drill |
| | | −2 | Mini Drawbacks/Balance Board & club |
| | | −5 | Mini Swings/Balance Board & club |
| | | −10 | Mini Swings Level 2/ Balance Bd & club |
| | | −15 | Mini Swings Level 1/ Balance Bd & club |
| | | −20 | Mini Swings/Base Platform & 5 Iron |
| | Center Align. Line, Rt. Lat. Bend. | 0 | No Drill |
| | | 2 | Mini Drawbacks/Balance Board & club |
| | | 5 | Mini Swings/Balance Board & club |
| | | 10 | Mini Swings Level 2/ Balance Bd & club |
| | | 15 | Mini Swings Level 1/ Balance Bd & club |
| | | 20 | Mini Swings/Base Plaform & 5 iron |
| Hip | Rotation, Left | −20 | No Drill |
| | | −25 | Hockey Swings/Base Platform & club |
| | | −30 | Double Post Swing/Base Platform & club |
| | | −35 | Mini Swings/Full Foam Roller & club |
| | | −40 | Mini Swings/Half Foam Roller & club |
| | Rotation, Right | 20 | No Drill |
| | | 25 | Hockey Swings/Base Platform & club |
| | | 30 | Double Post Swing/Base Platform & club |
| | | 35 | Mini Swings/Full Foam Roller & club |

TABLE 1-continued

Diagnostic Parameters and Exercises
Relating to Components of Motion

| Subject Area | Test/Measurement Parameter | Deviation (degrees) | Prescribed Exercise/Tool |
|---|---|---|---|
| | | 40 | Mini Swings/Half Foam Roller & club |
| Shoulders | Rotation, Left | (neg)0-10 | No drill |
| | | (neg)15-20 | Torso Twist/Base Platform & Stability Ball |
| | | (neg)25-30 | Torso Twist Counter & Primary/Base Plat. |
| | | (neg)35-40 | Torso Twist Blast/Base Platform |
| | | (neg)45-50 | Torso Twist Drawbacks/ Base Platform |
| | Rotation, Right | 0-10 deg | No drill |
| | | 15-20 deg | Torso Twist/Base Platform & Stability Ball |
| | | 25-30 deg | Torso Twist Counter & Primary/Base Plat. |
| | | 35-40 deg | Torso Twist Blast/Base Platform |
| | | 45-50 deg | Torso Twist Drawbacks/ Base Platform |
| Hip | Linear Address to Max Backswing | 0-2 cm | Double Post Swings/club |
| | | 3-5 cm | Bentley Swings/Base Platform & club |
| | | 6-8 cm | Hans Jumps/Impact Bag & Base Platform |
| | Linear Impact to Max Finish | 0-2 cm | Double Post Swings/club |
| | | 3-5 cm | Bentley Swings/Base Platform & club |
| | | 6-8 cm | Hans Jumps/Impact Bag & Base Platform |
| Hips | Static Posture | 0 | No drill |
| | | 1-10 deg | Posture Stick/Base Platform & club |
| Shoulders | Static Posture | 0 | No drill |
| | | 1-10 deg | Posture Stick/Base Platform & club |

Explanations and detailed instructions for the user's prescribed exercises are available on the local system 70, or may be accessed directly or remotely via an internet access to a host enterprise (FIG. 2) with which the local system 70 is affiliated.

Referring to FIG. 1, steps of Test 100-Prescribe 500 require at least a local system 70, while the exercise step 600 is, of course, executed by the user until he or she is ready to retest. A change in performance in a given primary parameter may or may not change the final kinetic index, but it will result in a change in prescription to a next level of exercise applicable to that performance parameter.

Figure 17:
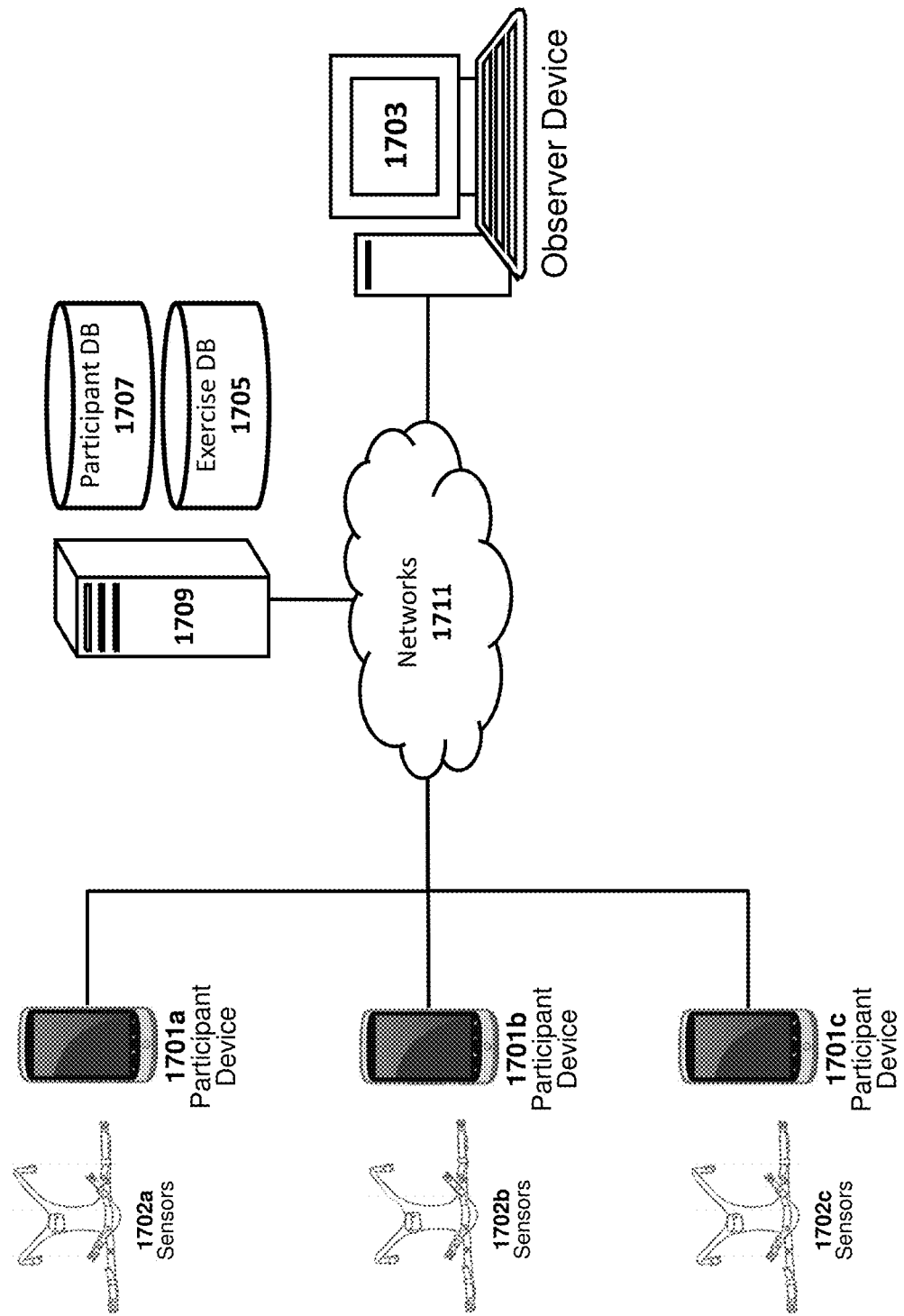
FIG. 17 shows components of a motion instruction system, according to an exemplary system embodiment.

FIG. 17 shows components of a motion instruction system 1700, according to an exemplary system embodiment. An exemplary system 1700 may comprise participant devices 1701, sensors 1702, observer devices 1703, an exercise database 1705, a participant database 1707, one or more servers 1709, and one or more networks 1711.

Participant devices 1701 may monitor and capture sensor data received from sensors 1702, and to communicate various types of data and instructions to and from devices of the system 1700, such as servers 1709 and observer devices 1703. A participant device 1701 may be any computing device comprising hardware and software components capable of performing the various tasks and processes described herein. Non-limiting examples of a participant device 1701 may include: laptop computers, desktop computers, smartphones, tablets, wearable devices (e.g., smart watches smart glasses, AR headsets, VR headsets, etc.), and the like.

A participant device 1701 may comprise a communications component configured to facilitate wired or wireless data communications between a set of one or more sensors 1702 and the participant device 1701. The communications component may comprise one or more circuits, such as processors and antennas, for communicating sensor data via a communications signal using an associated wired or wireless communications protocol. For example, the communications component of the participant device 1701 may include, for instance, a Bluetooth® or ZigBee® chip that may be configured to monitor and receive sensor data from the set of one or more sensors 1702 associated with the participant device 1701, via the requisite Bluetooth® or ZigBee® protocols. Other non-limiting examples of the communications component and associated protocols may include: a Network Interface Card (NIC) for LAN or Wi-Fi communications, a Near Field Communications (NFC) chip, and the like.

A participant device 1701 may comprise another communications component configured to communicate data and instructions with other devices of the system 1700, such as servers 1709 and observer devices 1703, over one or more networks 1711. For example, the communications component of the participant device 1701 may include, for instance, a wireless NIC allowing the participant device 1701 to communicate data and instructions with servers 1709 and/or observer devices 1703, over one or more networks 1711, using Wi-Fi, TCP/IP, and other, related protocols.

As mentioned, the communications component of a participant device 1701 may be configured to receive sensor data from a set of one or more sensors 1702 configured to capture motion and posture data of a participant, which may then be transmitted to the participant device 1701 as the sensor data. Sensors 1702 may include one or more types of sensors that may be configured to capture the motion and posture data of the participant. Non-limiting examples sensor types may include inertial or movement sensors having a gyroscope, an accelerometer and/or a magnetometer, heat sensors, image sensors (i.e., cameras) capturing still images and/or video images, optical body motion sensors, and the like. In some implementations, the sensors 1702 may be mixed-and-matched and the various types of sensor data may be synchronized, such that the participant device 1701 may receive, and, in some cases, process, the various types of sensor data. Portions of the sensor data may comprise performance parameters and/or diagnostic parameters. Parameters may correspond to fields of data models used by a computing device, such as servers 1709 or observer devices 1703, to model an expected motion or posture data for a particular motion or posture, category of activities, or exercises.

As an example, a factory employee instructional application executed by a participant device 1701 of a factory employee may be configured to teach the factory employee to perform a predetermined set of motions, and then monitor the employee's performance of the motions. While teaching the employee the predetermined motions, the participant device 1701 may receive sensor data from sensors 1701, and may then establish a baseline competency for the employee to perform the motions. This may be done using diagnostic parameters captured in the sensor data. The sensor data may then be transmitted to a server 1709 and/or an observer device 1703. A data library or database located on the participant device 1701, a server 1709, or an observer device 1703, may store data models for each of the predetermined motions. These data models may indicate which data fields or portions of the sensor data are part of the diagnostic parameters for each of the motions.

An observer device 1703 may be operated by an observer (e.g., coach, therapist, doctor, researcher, employer, instructor) and/or system administrator to monitor sensor data from, and communicate instructions with, any number of participant devices 1701a-c. Such monitoring and instructions can also be done autonomously through the use of a trained machine learning module (discussed in more detail below). The observer device 1703 may be any computing device comprising hardware and software components configured to perform the various tasks and processes described herein. Non-limiting examples of the observer device 1703 may include: a laptop computer, a desktop computer, a smartphone, and a tablet. The observer device 1703 may comprise communications components allowing the observer device 1703 to communicate with participant devices 1701a-c simultaneously or near-simultaneously, such that an observer operating the observer device 1703 may review sensor data received from and transmit instructions to, each of the participant devices 1701a-c.

A server 1709 may provide services for monitoring, storing, processing, and communicating sensor data and instructions between devices of the system 1700, such as participant devices 1701 and an observer device 1703. Such services may be cloud based. The server 1709 may be any computing device comprising hardware and software components configured to perform various tasks and processes described herein. Non-limiting examples of the server 1709 may include: a laptop computer, a desktop computer, a smartphone, and a tablet. The server 1709 may comprise communications components configured to allow the server 1709 to communicate with participant devices 1701a-c and/or the observer device 1703 simultaneously or near-simultaneously. For example, the server 1709 may receive sensor data from a plurality of participant devices 1701a-c, and may then covert the sensor data into a file format viewable, sometimes in real-time, from the observer device 1703 (and/or participant devices 1701a-c). As such, an observer device 1703 may access the server 1709 to review or receive real-time sensor data from the server 1709 while the server 1709 receives a data stream of sensor data from the participant devices 1701a-c.

A system 1700 may comprise one or more servers configured to host one or more databases, such as an exercise database 1705 and a participant database 1707. The servers hosting the databases may be any computing devices comprising a processor and non-transitory machine-readable storage media allowing the databases to perform the various tasks and processes described herein. In some embodiments, the databases may be hosted on the same device or on distinct devices. In addition, in some embodiments, a database may be hosted on a computing device that may be used for other purposes. For instance, an exercise database 1705 may be hosted on a server 1709, an observer device 1703, or a participant device 1701, while a participant database 1707 may be hosted on a server 1709.

An exercise database 1705 may store a plurality of exercise records containing data fields associated with exercises. The data fields of a particular exercise may include indicators of the activity categories (e.g., motions, postures, actions) that may benefit from the exercise. The exercise record may include a data model that models the sensor data inputs and parameters that may be used to measure how well the participant is performing the exercise.

A participant database 1707 may store a plurality of participant records containing data field associated with participants. The data fields of a particular participant may include data about the participant, such as vital information about the participant (e.g., name, participant identifier, height, weight), a history of sensor data and parameters, threshold values determined for the participant, and the like.

In some implementations, an observer device 1703 and/or a server 1709 may be configured to automatically generate a set of exercises for participants based the sensor data received from the participant devices 1701*a-c*. For example, the set of exercises may be based on diagnostic and/or performance parameters of the sensor data. Additionally or alternatively, the software application executed by the observer device 1703 and/or the server 1709 may generate a user interface allowing the observer to input parameter values and/or the set of exercise. For example, for implementations where the system 1700 automatically generates a set of exercises, the diagnostic parameters may be identified in the sensor data and then applied to a data model for a particular motion, or other activity category, to determine a participant's initial skill level, or diagnostic score, for a targeted motion. Based on a diagnostic score calculated for the activity category using the data model, the server 1709 and/or observer device 1703 may identify a set of exercises in an exercise database 1705 determined to be appropriate for the participant's capabilities for the activity category. The set of exercises may be updated and revised as the participant improves a diagnostic score that was calculated for a particular activity category, which may correspond to a particular motion, posture, collection of muscles, or other movement skill (e.g., throwing a baseball, swinging a golf club, a predetermined labor-related motion). The targeted motion may be defined by a data model comprising a set of parameters for motions or postures captured in the sensor data of particular motions or postures; an activity category may be used to identify exercises or other data points and data structures associated with improving upon the targeted motion. For example, the targeted motion and activity category may be associated with improving a runner's stride. In this example, diagnostic and/or performance parameters for this activity category may capture sensor data for aspects of a runner's stride (e.g., upright posture, length of leg extension, arm swing), and the exercises for this activity category may include exercises for improving upon speed and posture (e.g., squats, wall sits, leg extensions, sprints).

The observer device 1703 or server 1709 may generate a regime file, after selecting the set of exercises for an exercise regime to improve a participant's diagnostic score for an activity category or to improve a participant's performance for a given exercise. The regime file may contain data that may be used by an application executed by a participant device 1701 to identify the selected exercises, display the appropriate exercises on the user interface of the participant device 1701, and to capture and send the appropriate sensor data from the sensors 1702. The server 1709 or observer device 1703 may utilize data from the exercise, participant, and/or motion databases to generate each exercise in the regime file. For example, the server may query the exercise database from the latest performed range of motion exercise performed by a given participant and use this information to generate exercises in the regime file with appropriate ranges.

It should be appreciated that the regime file may be one or more machine-readable data files of nearly any file type that may be used as a binary or library of the application. Non-limiting examples of the regime file may include: a database file or database records (e.g., SQL code), a text document, an XML file, an HTML file, an executable file (.exe), a code script (e.g., python, java, C, C++, perl), and the like. The application may be configured to receive and read the data fields of the regime file, which may instruct the participant device 1701 to generate user interfaces displaying still images or multimedia examples of particular postures, motions, or exercises. In some cases, the application may have a set of APIs that correspond to the inputs and outputs of the regime file, allowing the regime file to pass data and instructions to the application. The regime file may contain data associated with the selected exercises; the server or observer device 1703 may query the exercise database 1705 to extract the data of the regime file from the data fields of the exercise records. In some implementations, the regime file may be transmitted directly from the observer device 1703 to participant devices 1701, using a communications protocol and application (e.g., email, FTP, communication protocol native to exercise application). In some implementations, a server 1709 may store a regime file in a participant database 1707 or other storage location, accessible to participant devices 1701 and an observer device 1703.

A system and method for analyzing and improving the performance of an athletic motion such as a golf swing may require: instrumenting a user with sensors (e.g., inertial or movement sensors) and optionally with video cameras, time of flight cameras, or radar-based systems capable of capturing 2D or 3D scene information at regular time intervals; monitoring a golf swing or other motion (athletic or otherwise) of interest; drawing upon and contributing to a vast library of performance data for analysis of the test results; scoring the motion; providing an information rich, graphic display of the results in multiple formats including video, color coded and stepped frame animations from motion data, and synchronized data/time graphs; and based on the results prescribing a user-specific training regime with exercises selected from a library of exercises. As discussed above, scoring the motion may involve scoring pre-defined parameters relating to component parts of the motion and combining the parameter scores to yield a single, kinetic index score for the motion.

Auto Capture

One or more embodiments of the invention may include an auto capture system in which data capture from the sensors (e.g., inertial sensors having a gyroscope, an accelerometer and/or a magnetometer, heat sensors, image sensors (e.g., cameras) capturing still images and/or video images, optical body motion sensors, and/or the like) is triggered by a specific input (e.g., a motion or gesture).

In such embodiments, streaming data may be processed in real time, or near real time, and when a specific input (e.g., gesture) is recognized (e.g., a golf swing), a time window of sensor data is automatically recorded. The time window being taken from a predetermined time period around the moment in time in which the specific input was recognized (e.g., when the gesture occurred). For example, the predetermined time period may include 2 seconds before the moment in time when the specific input was recognized and 3 seconds after the moment in time when the specific input was recognized.

Figure 18A:
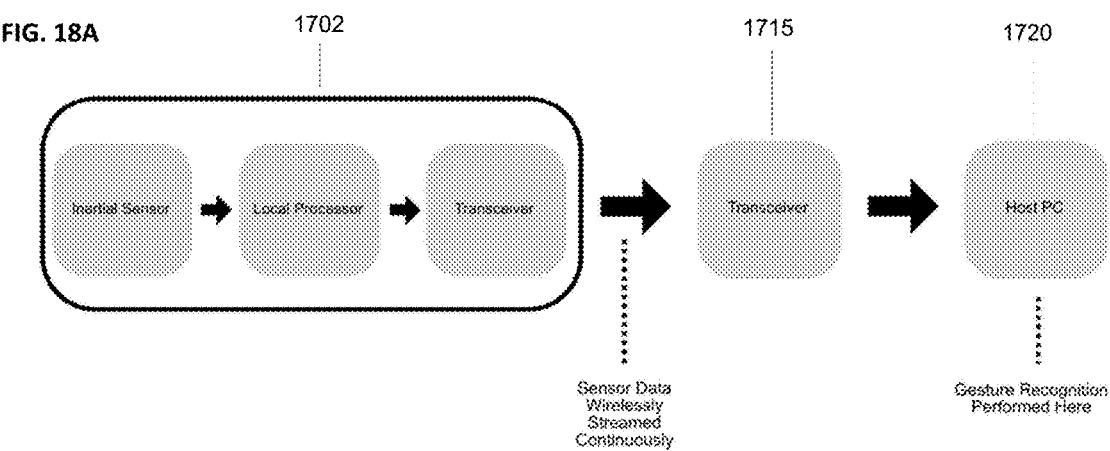
FIG. 18A shows a block diagram of an auto capture implementation of a motion instruction system, according to an exemplary system embodiment.
Figure 18B:
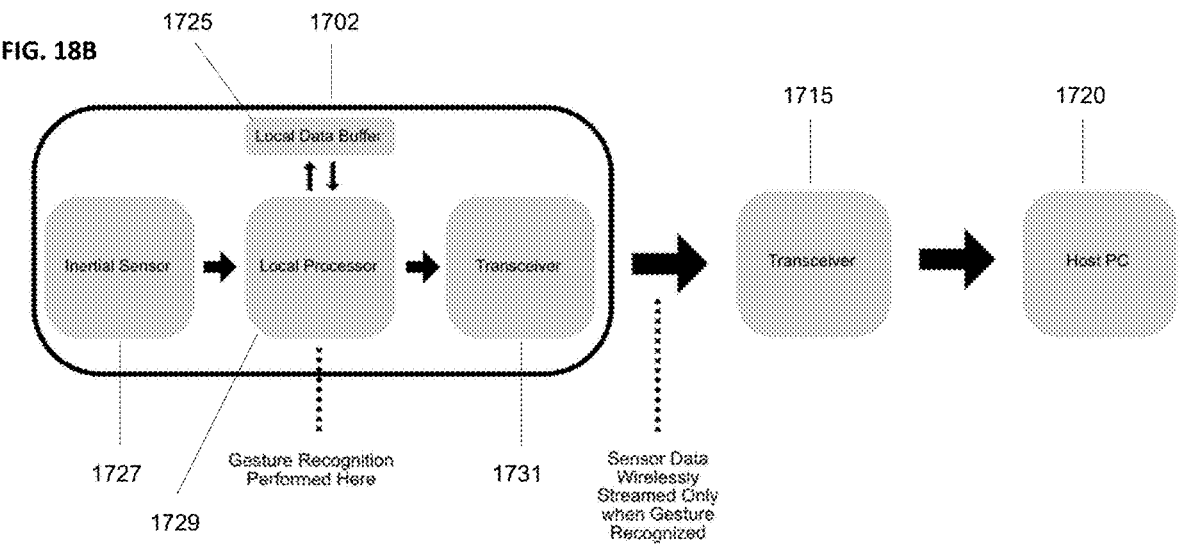
FIG. 18B shows a block diagram of another auto capture implementation of a motion instruction system wherein sensor data is transmitted from a sensor only upon recognition of a motion or gesture, according to an exemplary system embodiment.

Exemplary embodiments of the auto capture system are illustrated in FIGS. 18A and 18B.

According to the embodiment illustrated in FIG. 18A, gesture recognition for an auto capture system may be performed by a processor of the participant device 1701 and/or observer device 1703 or server 1709 (participant device 1701, observer device 1703, and server 1709 are collectively referred to herein as the "CPU"). Here, sensor data is continuously wirelessly streamed from the sensors 1702 to a transceiver 1715 of the CPU 1720. The sensor data is transmitted to the CPU transceiver regardless of whether any motion gesture (e.g., golf swing, baseball bat swing, etc.) has occurred. The transmitted sensor data may be buffered in a data buffer of the CPU. Upon recognition of the motion gesture, the CPU extracts from the data buffer sensor data in which is a predetermined time window around the moment in which the gesture took place, including before the gesture was recognized. The extracted sensor data is then processed by the CPU to generate a set of exercises for participants based on the sensor data received from the participant device 1701.

Alternatively, as shown in the embodiment illustrated in FIG. 18(b), gesture recognition for an auto capture system may be performed with an algorithm and processing being performed in the sensors 1702 themselves, as opposed to the CPU. Wirelessly transmitting sensor data from the sensors to the CPU transceiver requires significant power consumption that monotonically scales (i.e., increases) with greater transmission distance. Thus, it may be advantageous (e.g., with regard to power consumption and CPU processor efficiency) to perform gesture recognition locally on the sensor, and only transmit data to the CPU when a motion gesture is recognized. The transmitted data may include only sensor data in a predetermined time window around the moment in which the gesture took place, including before the gesture was recognized. This can be achieved in one embodiment through the use of a local data buffer 1725 in the sensors.

The local data buffers 1725 may exist in one or more of the sensors. The sensors may be considered separate from each other or be ganged or networked together in some relationship configuration. For example, sensor data may be transmitted from one or more sensors to a local data buffer existing in another sensor. The aggregate sensor data from the sensors may then be transmitted from that local data buffer 1725 to the CPU transceiver.

For example, as shown in FIG. 18B, an exemplary sensor 1702 itself may comprise a sensor 1727 (e.g., inertial sensor), a local processor 1729, a local data buffer 1725, and a transceiver 1731. The sensor data is initially buffered in the local data buffer 1725. Alternatively, one or more sensors may include more or less components. Upon recognition by the local processor of a motion gesture, the local processor extracts from the local data buffer sensor data in a predetermined time window around the moment in which the gesture took place, including before the gesture was recognized. Only the extracted buffer sensor data is wireless transmitted to a transceiver of the CPU. Thus, in this embodiment, the algorithm and processing for motion gesture is performed in the sensor as opposed to the CPU. The transmitted sensor data include only sensor data in a predetermined time window around the moment in which the gesture took place, which is advantageous in that it decreases wireless sensor data transmission and corresponding power thereby improving efficiency.

For example, in a golf scenario, an impact that occurs when a golfer strikes a golf ball may result in a particular signature of at least one of acceleration data, body segment orientation data, and rotational velocity data. This impact can be measured by a handset sensor, wrist sensor, and/or a club mounted sensor. The signature may be used by the system to automatically identify a particular motion gesture (e.g., golf swing). Then, as discussed above, a predetermined time window of the sensor data may be analyzed by the system.

Similarly, in a baseball scenario, an impact that occurs when a batter strikes a baseball may result in a particular signature of at least one of acceleration data, body segment orientation data, and rotational velocity data. This impact can be measured by a handset sensor, wrist sensor, and/or a club mounted sensor. The signature may be used by the system to automatically identify a particular motion gesture (e.g., baseball bat swing). Then, as discussed above, a predetermined time window of the sensor data may be analyzed by the system.

Autonomous Training

Figure 19A:
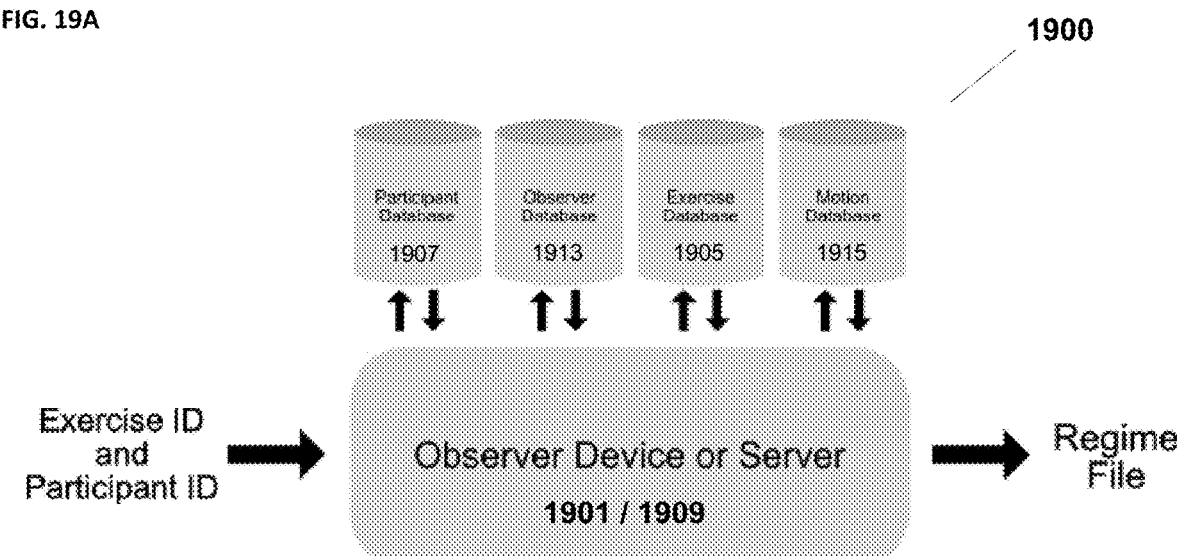
FIG. 19A shows a block diagram of a regime file generation process, according to an exemplary system embodiment.
Figure 19B:
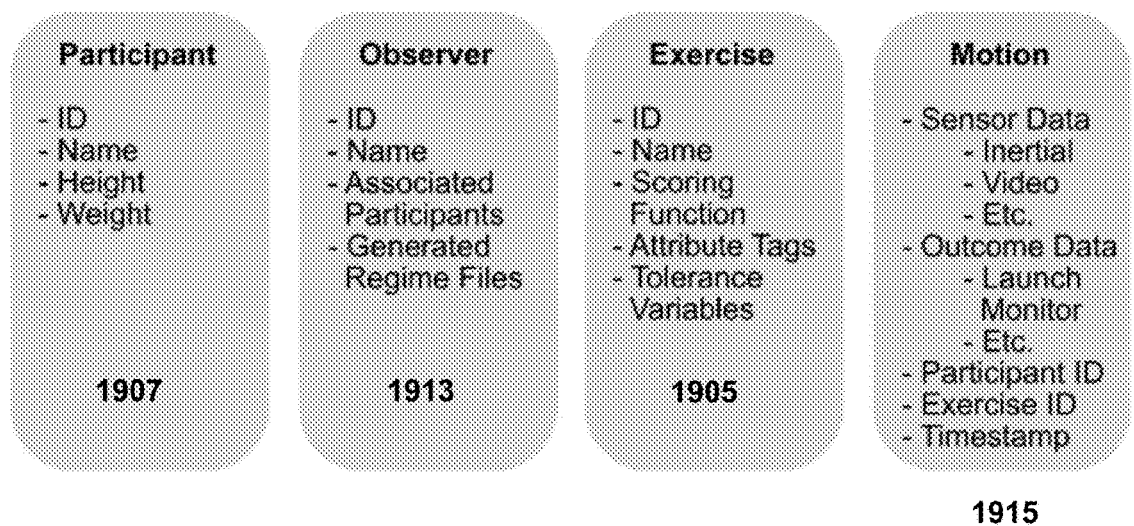
FIG. 19B shows an exemplary block diagram of proposed data fields for the regime file generation process of FIG. 19A.

An alternative embodiment of an autonomous training system for a motion instruction system 1900 is illustrated in FIGS. 19A and 19B, wherein the regime file (e.g., list of recommended exercises) is customizable for individual participants based on data in a participant database. A separate description of the portions of the system having the same structure and function as those of the previous embodiment are omitted for purposes of convenience to the reader, and the differences from the previous embodiment are herein described.

The customizable regime files may be of particular use with (although not limited to) large groups of participants wherein each participant is at a different level of proficiency. The customizable regime files allow all participants to be together but some to work completely alone (without coaching or training) while others receive coaching; and where all of the participants receive unique versions of the same program based on the individual participant profiles.

As previously described with regard to the embodiment illustrated in FIG. 17, the motion instruction system 1900 may comprise participant devices 1901, sensors 1902, observer devices 1903, one or more databases, one or more servers 1909, and one or more networks 1911. As illustrated in FIG. 19A, the one or more databases may include an exercise database 1905, a participant database 1907, an observer database 1913, a motion database 1915. A separate description of the portions of the system 1900 having the same structure and function as those of the previous embodiments are omitted for purposes of convenience to the reader, and the differences from the previous embodiment are herein described.

FIG. 19B illustrates various data fields that may be associated with the exercise database 1905, participant database 1907, observer database 1913, and motion database 1915, which may be collectively used to generate the regime file. In alternative embodiments, additional or different data may be used to generate the regime file.

The participant database 1907 may store user or participant related information. The information stored therein may consist of data fields such as Participant ID, Participant Name, Participant Height, Participant Weight, etc.

The observer database 1913 may store observer (e.g., coach, trainer, etc.) related information. The information stored therein may consist of data fields such as Observer ID, Observer Name, Associated Participants (e.g., participants associated with the observer, such as a class of 50 trainees), Generated Regime Files, etc.

The exercise database 1905 may store exercise related information. For purposes herein, it is understood that "exercise" may include a training exercise (e.g., bend at address) as well as movements such as a golf swing (previously referred to herein as an Activity Category). Each exercise may include one or more component motions. The information stored therein may consist of data fields such as Exercise ID, Exercise Name, Scoring Function, Attribute Tags, Tolerance Variables, etc.

The motion database 1915 may store captured motion data for an exercise. The information stored therein may consist of data fields such as Sensor Data (e.g., inertial, video, etc.), Outcome Data (e.g., launch monitor, etc.), Participant ID, Exercise ID, a Timestamp, etc.

In a non-limiting example, such as shown in FIG. 19A, when an Exercise ID (e.g., ID for golf swing) and Participant ID are input, an observer device 1903 and/or server 1909 utilizes data from the exercise database 1905, participant database 1907, observer database 1913, and motion database 1915 to generate a regime file customized to the participant. The regime file may be generated autonomously using a content-based filtering approach, which leverages a machine learning model trained on data associated with a participant matching the Participant ID input (discussed in more detail below). Alternatively, the regime file may be generated autonomously using a collaborative filtering approach, which leverages a machine learning model trained on data associated with all participants. Alternatively, the regime file may be generated with a hybrid approach of both content-based filtering and collaborative filtering. Thus, the observer device 1903 and/or a server 1909 may be configured to automatically generate a set of exercises for participants based on diagnostic and/or performance parameters of the sensor data received from the participant devices 1901.

In a non-limiting example, generating the regime file using the content-based filtering approach may involve having a library or exercise database 1905 of N different training exercises for which an exercise vector of length N can be initialized and updated as follows:

Initialization: For a new user, initialize the exercise vector to the zero vector. For example, for a library of 5 exercises consisting of "Rotation at Impact", "Bend at Address", "Rotation at Impact", "Hip Twister", and "Duck Walks", the exercise vector would be initialized to [0, 0, 0, 0, 0].

Update Algorithm:

Step 1. After a specific interval of time after a user performs one or more training exercises, calculate an output score ($S_{AFTER}$) based on all swings taken since the training exercises were performed. For example, this score could be the average carry distance of a golf ball for all swings taken within 12 hours since the last of the training exercises was performed.

Step 2. Calculate an output score ($S_{BEFORE}$) based on all swings taken within a specific interval of time before the user performed the training exercises. For example, this score could be the average carry distance of a golf ball for all swings taken within 12 hours before the first of the training exercises was performed.

Step 3. Calculate the change in output scores as: $\Delta S = S_{AFTER} - S_{BEFORE}$.

Step 4. For each of the exercises that were performed in this iteration, add the change in output scores to the corresponding element of the exercise vector.

Exercise Recommendation Algorithm: For each user, the exercise vector provides a means of ranking training exercises based on how much they improve the output score of interest. For example, an exercise recommendation algorithm could be to recommend M exercises with the highest values in the exercise vector, where M<=N. However, this approach may be prone to converge on a local optimum as soon as M exercises achieve values greater than 0 in the exercise vector. Another exercise recommendation algorithm could be to recommend M+L exercises (where M+L<=N), consisting of M exercises with the highest values in the exercise vector and L exercises chosen at random from the remaining N-M exercises. The invention is of course not limited to these two exemplary content-based filtering exercise recommendation algorithms In a non-limiting example, the collaborative filtering approach for generating the regime file may involve implementing a collaborative filtering algorithm by extending the content-based filtering approach described above. In order to do this, for example, an augmented exercise vector of length N may be defined. The elements of a user's augmented exercise vector corresponding to exercises that have been performed at least once by the user are assigned the same values as the corresponding elements in the user's exercise vector. The elements of a user's augmented exercise vector corresponding to exercises that have never been performed before by the user are assigned the same values as the corresponding elements in the exercise vector of the user in the participant database who is most similar to the user of interest. Similarity between two users can be determined by the inner product of their normalized exercise vectors (higher values indicate greater similarity). With the foregoing technique, an exercise recommendation algorithm could be that for each user, recommend M+L exercises (where M+L<=N), consisting of M exercises with the highest values in the augmented exercise vector and L exercises chosen at random from the remaining N-M exercises. The invention is of course not limited to the foregoing collaborative filtering exercise recommendation algorithm.

Dynamic Motion Scoring and Training

According to another embodiment of the invention, the motion instruction system 1900 may operate in a dynamic biofeedback mode. In this mode, the processing computer performs a dynamic motion scoring process and trains a dynamic motion as opposed to one or more static postures. A separate description of the portions of the system having the same structure and function as those of the previous embodiment are omitted for purposes of convenience to the reader, and the differences from the previous embodiment are herein described.

In the dynamic biofeedback mode, the motion instruction system 1900 may compare biomechanical parameters computed for a captured motion (discussed above) to a previously generated motion template stored in a database. The motion instruction system 1900 may then compute a similarity score. For example, a similarity score of 0 may be used to represent a perfect similarity match (i.e., the derived biomechanical parameters are identical to the motion template), and a similarity score of positive values (e.g., 1-100) may be used to represent degree of mismatch. The similarity score may then be displayed on the participant device 1701, or another display or recipient device that is configured to convey feedback to the user.

Figure 20:
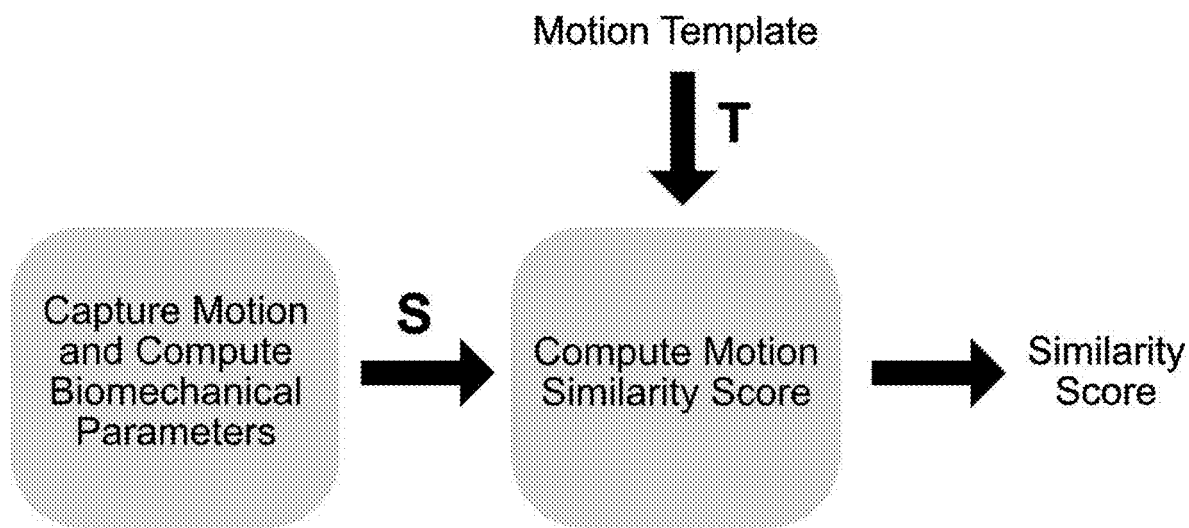
FIG. 20 is a block diagram of an process for computing a motion similarity score, according to an exemplary system embodiment.

FIG. 20 is a block diagram of an exemplary process for computing a motion similarity score. As shown, the motion instruction system 1900 computes a motion similarity score based on a comparison of biomechanical parameters computed for a captured motion (discussed above) to a motion template stored in a database. The motion template may have been generated from a single captured motion (e.g., best golf swing), multiple captured motions (e.g., top 5 best golf swings), or manually synthesized.

Based on the similarity score, the motion instruction system 1900 can then generate an auditory, visual, and/or haptic biofeedback signal. The biofeedback signals may be different depending on the similarity score. For example, the similarity score may range from 0 to 100, with zero being ideal and 100 representing a high divergence from the ideal. In this example, a red light might follow an exercise in which a derived biomechanical parameter badly diverged from ideal (e.g., score of 50-100), a yellow light might follow an exercise in which a derived biomechanical parameter only somewhat diverged from ideal (10-49), and a green light might follow an exercise in which a derived biomechanical parameter is ideal or diverged from ideal by less than the pre-assigned margin of error (0-9). The signal light may be the background color of an animation or avatar displayed on the participant device 1901 and/or observer device 1903, or another display or recipient device that is configured to convey feedback to the user. Similar differences in biofeedback signals could be done using audio or haptic signals.

Furthermore, unlike static posture training, where only differences in posture are considered, the dynamic biofeedback similarity score may also capture differences in timing.

An exemplary algorithm for generating a similarity score is described below:

Step 1:

Create a motion template T in the form of an M×N matrix, where each of M rows represents a motion parameter time series of length N. For example, the motion template may include timestamps or time samples that are evenly spaced in time based on a sampling rate (e.g., 200 Hz so that the samples are 5 ms apart). Alternatively, the motion template may include time spacing that is unequal in order to capture key moments in a movement, such as address, top, and impact of a golf swing. The motion parameters may include but are not limited to 3D orientation data (yaw, pitch, roll); raw 3-axis sensor data (accelerometer$_x$, accelerometer$_z$, accelerometer$_z$, gyroscope$_x$, gyroscope$_y$, gyroscope$_z$, magnetometer$_x$, magnetometer$_y$, magnetometer$_z$) from one or more inertial sensors; sensor data from other sensors such as heat sensors, image sensors (i.e., cameras) capturing still images and/or video images, optical body motion sensors, and the like; as well as subsequently derived biomechanical parameters. The biomechanical parameters may include, for example, one or more of: 'Shoulder Flexion', 'Hip Flexion', 'Hand Flexion', 'Upper Arm Flexion', 'Shoulder Tilt', 'Hip Tilt', 'Hand Tilt', 'Upper Arm Tilt', 'Shoulder Alignment', 'Hip Alignment', 'Hand Alignment', 'Upper Arm Alignment', 'Shoulder Rotation', 'Hip Rotation', 'Hand Rotation', 'Upper Arm Rotation', 'Pelvis Rotation', 'Torso Rotation', 'Shoulder Lateral Bend', 'Hip Lateral Bend', 'Hand Lateral Bend', 'Upper Arm Lateral Bend', 'Shoulder Pitch', 'Hip Pitch', 'Hand Pitch', 'Upper Arm Pitch', 'Shoulder Angle', 'Hip Angle', 'Hand Angle', 'Upper Arm Angle', 'Shoulder Direction', 'Hip Direction', 'Hand Direction', 'Upper Arm Direction', 'Torso Rotational Velocity', 'Pelvis Rotational Velocity', 'Hand Rotational Velocity', 'Upper Arm Rotational Velocity', 'Spine Angle', 'Pelvis Angle', 'Wrist Angle', 'Spine Direction', 'Pelvis Direction', 'Wrist Direction', 'Upper Body Bend', 'Upper Body Side Bend', 'Pelvis Bend', 'Pelvis Side Bend'.

Step 2:

Build an M×K matrix S from a captured motion consisting of K samples, where K≥N, such that each of M rows represents the same motion parameters as in the motion template matrix T.

Step 3:

Align S to T using cross-correlation and truncate non-overlapping columns as follows:

i. Select a motion parameter row to use for alignment (e.g. torso sensor yaw).

ii. Calculate the lag $\tau$ between $T_{i,*}$ and $S_{i,*}$ as: $\tau = \underset{n}{\mathrm{argmax}}(T_{i,*} * S_{i,*})[n]$ iii. If 0≤τ≤K−N, truncate the first r columns and last (K−N−τ) columns of S to yield M×N matrix $$\hat{S} = \begin{bmatrix} S_{0,\tau} & \cdots & S_{0,\tau+N-1} \\ \vdots & \ddots & \vdots \\ S_{M,\tau} & \cdots & S_{M,\tau+N-1} \end{bmatrix}.$$

Else, if τ<0 or τ>K−N, stop here and raise an error indicating that the captured motion does not contain data matching the entire template.

Step 4:

Compute the overall similarity score as a weighted sum of normalized root mean square error (NRMSE) values between corresponding rows of $\hat{S}$ and T:

$$\text{Similarity Score} = \sum_{i=0}^{M} w_i * \frac{\|T_{i,*} - \hat{S}_{i,*}\|}{\|T_{i,*}\|}$$

where each value $w_i$ is a scalar weight applied to the NRMSE for row i.

According to one or more of the foregoing embodiments, the biofeedback mode of the motion instruction system 1900 allows a user to "train to his or her best motion." According to a non-limiting example, such training may be accomplished by:

(1) storing motion data for one or more captured motions for an exercise in a motion database 1915;

(2) computing and assigning a score for each captured motion. Such scoring can be assigned manually through user-tagging, or, as discussed above, computed automatically through a scoring algorithm based on a comparison of biomechanical parameters computed for a captured motion to a motion template stored in a database;

(3) computing the user's "best motion" based on a comparison of the captured motion data and assigned scores; and (4) generating a corresponding set of static postures and/or motion templates for use in biofeedback training exercises.

According to one or more of the foregoing embodiments, the motion instruction system 1900 may generate comprehensive user health, fitness, and skill scores based on many component diagnostic scores. Although some prior embodiments describe "activity categories," it is understood that such activity categories may relate to exercises, which can include training exercises (e.g. bend at address) and specific motions (e.g. golf swing) and "diagnostic scores," and the concept of "scoring functions" can be assigned to each exercise. The outputs of these scoring functions may be used to represent performance on specific training exercises, quality of specific motions, and even things like range of motion for particular body segments. Furthermore, group health, fitness, and skill scores can be generated for groups of users (e.g. teams or organizations) based on the individual user health, fitness, and skill scores of their members. This may be beneficial for group competitions where one group of users competes against another group of users, such as in a group training class.

According to one or more of the foregoing embodiments, the motion instruction system 1900 may be configured to continually monitor user compliance with a training regime. For example, in the factory worker example discussed above, user compliance with an exercise regime (e.g., assigned exercise score is above a predetermined threshold), or lack thereof (e.g., assigned exercise score is below a predetermined threshold, or the assigned exercise is not being performed), may be transmitted to an observer (via text message, e-mail message, alert on web portal, etc.). Preferably, such alert is transmitted to the coach or observer in real time so that the exercise regime may be revised or changed accordingly.

For example, such continual monitoring may be performed so that employers can ensure that their employees are complying with a particular training regime while in the workplace. Pre-determined movements of employees may be measured as they perform their regular day-to-day work tasks, such as, for example, lifting or walking. Such continual monitoring can be important to prevent injuries for employees performing repetitive tasks, such as those in hospitality (e.g., making beds), in a warehouse (e.g., lifting, pick and place movements), etc. Using the captured motion data, the motion instruction system 1900 assigns an exercise score for a particular exercise or movement being performed. When the exercise score is below a predetermined threshold or the assigned exercise or movement is not being performed, then the motion instruction system 1900 may transmit an alert to an observer (via text message, e-mail message, alert on web portal, etc.) to inform the employer that the employee is moving incorrectly (which puts them at risk of injury). Preferably, such alert is transmitted to the observer (employer) in real time so that the exercise regime may be revised or changed accordingly. Additionally, when the exercise score is below a predetermined threshold or the assigned exercise or movement is not being performed, then the motion instruction system 1900 may transmit an alert to the participant device so that the employee may have an opportunity to self-correct. If the employee fails to self-correct (i.e., the exercise score remains below the predetermined threshold), then the motion instruction system 1900 may send an alert to the participant device 1901 (as well as the observer device 1903) ordering the employee to stop and then guide the user through a protocol to activate muscles and remind them of the correct movement pattern via instructions (graphical, video, and/or textual) displayed on the participant device 1901 and/or the observer device 1903, or another display or recipient device configured to convey feedback to the employee.

According to an embodiment of the invention, the system 1900 may be configured to provide real-time alerts to a user, such as a coach/observer, to prevent injury. For example, a coach, organization, or general user (such as a participant) can set a custom alert trigger based on sensor data for a specific user or group of users. For example, a coach may set a trigger such that whenever a player with a back injury risk exceeds 60 degrees of forward bend of the torso, an alert is sent to him or her in the form of an email, text message, phone call, etc.

According to an embodiment of the invention, the system 1900 may be configured to provide real-time athlete monitoring for group training. In this embodiment, a group of users repeatedly train the same biofeedback exercise or perform swing motions at the same time. The motion data for each user is captured locally and immediately sent to the cloud, where it is processed to determine how well each user is performing each biofeedback exercise or swing motion. This data is then used to render a web dashboard to be viewed on an observer device 1903 by a coach. The rendering represents each user as a simple tile, which turns red if the user if performing poorly and green if the user is performing well (not limited to any particular color or look). This allows the coach to identify users in the group that are struggling or excelling during a live training session.

According to one or more of the foregoing embodiments, motion instruction system 1900 may be configured so that during exercise routines, real-time feedback or analysis may be provided to the user based on sensed data, including image data, about the user. In this manner, the system 1900 may function as a "virtual coach" to the user to help make exercising more interactive and help achieve results and goals of the user faster. In other words, such real time feedback may be based on any of a number of data inputs, such as personal data of the user, real-time exercise parameters of a current exercise session, and/or archived exercise parameters of past exercise sessions. The feedback may be transmitted from an observer device 1903 and/or server 1909 to the participant device 1901, or another display or recipient device that is configured to convey feedback to the user.

The virtual coach feature may operate by automatically generating useful tips and exercise lessons based on motion data from the sensors. For example, with a sport such as golf, such virtual coach feedback may be based on motion data from inertial sensors, club and ball data from a launch monitor apparatus (e.g., club speed, ball speed, launch angle, spin, and azimuth), and virtual course data from a golf simulator (e.g., ball position, course difficulty, weather conditions, terrain, etc.). These tips and lessons can be communicated to the user in real-time through text, audio, vibration, an animated coach avatar in the golf simulator, or any combination thereof. The same concept can be altered for other sports and activities, such as baseball, tennis, exercising, etc. Moreover, this concept may be extended to all forms of motion monitoring.

Training Motion Scoring Models with Supervised Machine Learning Algorithms

According to one or more of the foregoing embodiments, the system 1900 may apply machine learning techniques to learn relationships, functions, and categories associated with various analysis procedures, which may include modeling or scoring a particular motion gesture (e.g., golf swing) or exercise based on the sensor data. A supervised machine learning algorithm offers flexibility as it trains motion scoring models based on data, such as data contained in exercise database 1905, participant database 1907, observer database 1913, a motion database 1915, and/or subsets thereof.

An exemplary embodiment of a machine learning technique that may be used with one or more embodiments of the motion instruction system 1900 described herein is illustrated in FIGS. 21A and 21B and FIGS. 22A and 22B, and described below.

The machine learning algorithm may generally be configured to train two model categories: classification and regression. The classification model may output discrete class categories, e.g., classifying an input motion as "expert", "novice", or "beginner". The classification model may include, but is limited to, logistic regression, decision trees, decision forests, support vector machines, naïve bayes, k-nearest neighbors, and convolutional neural networks. The regression model may output continuous values, e.g., assigning a numerical score to an input motion. The regression model may include, but is not limited to, linear regression, polynomial regression, k-nearest neighbors, and convolutional neural networks. Trained classification and regression models can then be used to score input motions.

Figure 21A:
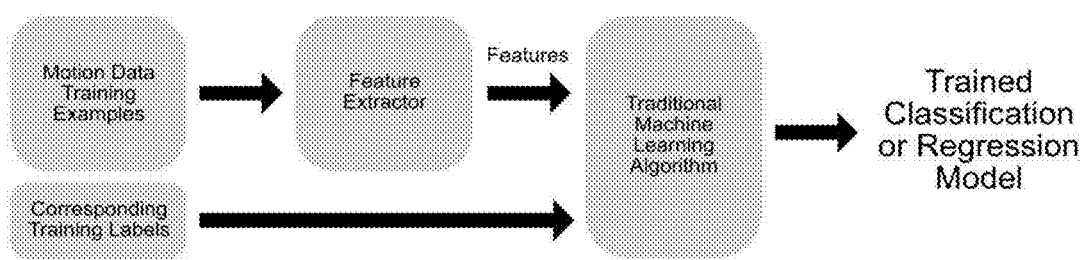
FIG. 21A is a block diagram of motion scoring model training using a traditional machine learning approach which leverages hand-engineered feature extraction, according to an exemplary system embodiment.

As shown in exemplary FIG. 21A, the motion scoring model training may use a traditional machine learning algorithm that leverages a hand-engineered feature extraction technique. The hand-engineered feature may include, but is not limited to, summary statistics, such as maximum rotational velocities, maximum accelerations, maximum body angles, average rotational velocities, average accelerations, average body angles, minimum rotational velocities, minimum accelerations, minimum body angles, etc. With such an approach, motion data training templates or examples with corresponding training labels (e.g., ground truth class labels for each training example when training a classification model, or ground truth numerical labels for each training example when training a regression model) are employed.

Figure 21B:
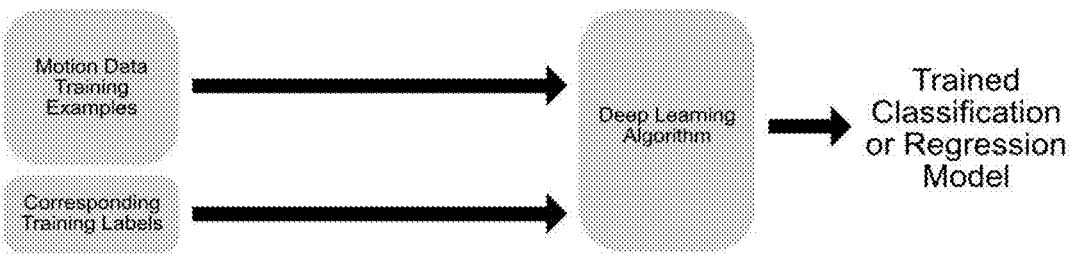
FIG. 21B is a block diagram of motion scoring model training using a deep learning framework technique, according to an exemplary system embodiment.

Alternatively, as shown in exemplary FIG. 21B, the motion scoring model training may use a deep learning framework. Unlike with the traditional machine learning algorithm such as shown in FIG. 21A, the deep learning framework does not leverage a hand-engineered feature extraction technique. With the deep learning framework, however, motion data training templates or examples with corresponding training labels (e.g. ground truth class labels for each training example when training a classification model, or ground truth numerical labels for each training example when training a regression model) are employed.

Figure 22A:
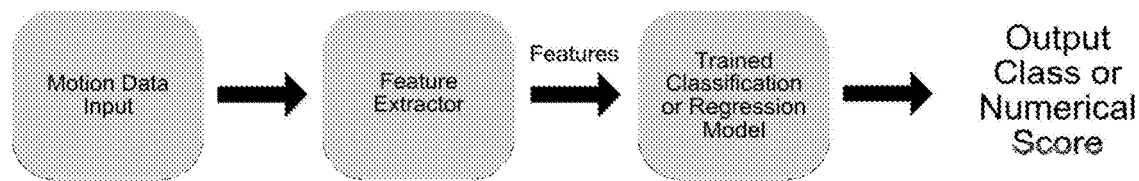
FIG. 22A is a block diagram of scoring motion data inputs using trained classification or regression models trained using a traditional machine learning approach which leverages hand-engineered feature extraction, according to an exemplary system embodiment.
Figure 22B:
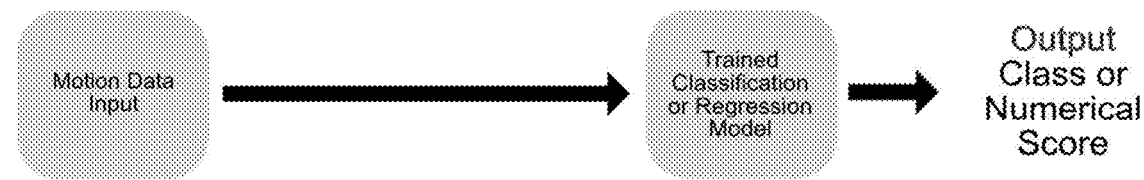
FIG. 22B is a block diagram of scoring motion data inputs using trained classification or regression models trained using a deep learning framework technique, according to an exemplary system embodiment.

FIGS. 22A and 22B are block diagrams of exemplary scoring motion data inputs using trained classification or regression models. More particularly, FIG. 22A illustrates an exemplary technique for scoring motion data inputs using a traditional machine learning approach which leverages hand-engineered feature extraction (such as shown in FIG. 21A). FIG. 22B illustrates an exemplary technique for scoring motion data inputs using a deep learning framework (such as shown in FIG. 22B). It is understood that for trained classification models, the output may be a class category, whereas for trained regression models, the output may be a numerical score (e.g., 0-100).

In one or more of the foregoing embodiments, the motion instruction system 1900 may be used for training a user (e.g., golfer) in a set of exercises based on continuously captured data (e.g., capture or auto capture motion data, measure the data, assess the data, coach the user, and prescribe training regime). The training may be based on pre-captured data (e.g., load and train a prebuilt program). The training may be for on a single motion parameter, or for more than one motion parameter. The user and or observer (coach) may select which motion parameter to target and/or which body segment to be trained.

In one or more of the foregoing embodiments, the motion instruction system 1900 may be used to train a user based on captured data. For example, instrumenting a user with sensors (e.g., inertial or movement sensors) and optionally with video cameras, time of flight cameras, or radar-based systems capable of capturing 2D or 3D scene information at regular time intervals; monitoring a golf swing or other motion (athletic or otherwise) of interest; capturing or auto capturing motion data of interest; drawing upon and contributing to a library of performance data for analysis of the test results; scoring the motion; providing an information rich, graphic display of the results in multiple formats including video, color coded and stepped frame animations from motion data, and synchronized data/time graphs; and based on the results prescribing a user-specific training regime. As discussed above, the system 1900 may apply machine learning techniques to learn relationships, functions, and categories associated with various analysis procedures, which may include modeling or scoring a particular motion gesture (e.g., golf swing) or exercise based on the sensor data.

In one or more of the foregoing embodiments, a user may train to his or her best swing (or any swing, any shot, or any ball flight) using captured or auto captured motion data. For example, a golfer may swing the club ten times and then select one of those swings (e.g., their best swing or a swing based on their desired body/ball performance) as a model swing. The motion instruction system can then automatically develop and prescribe a user-specific training regime based on the model swing. In this manner, a user-specific training regime can be prescribed for any motion that a user desires to repeat (e.g., their best swing). Thus, a dynamic training program can be generated for the selected swing so that a user can be coached and trained to perform the exact captured movement with video, audio, and/or haptic cues according to one or more of the above described embodiments.

Figure 23:
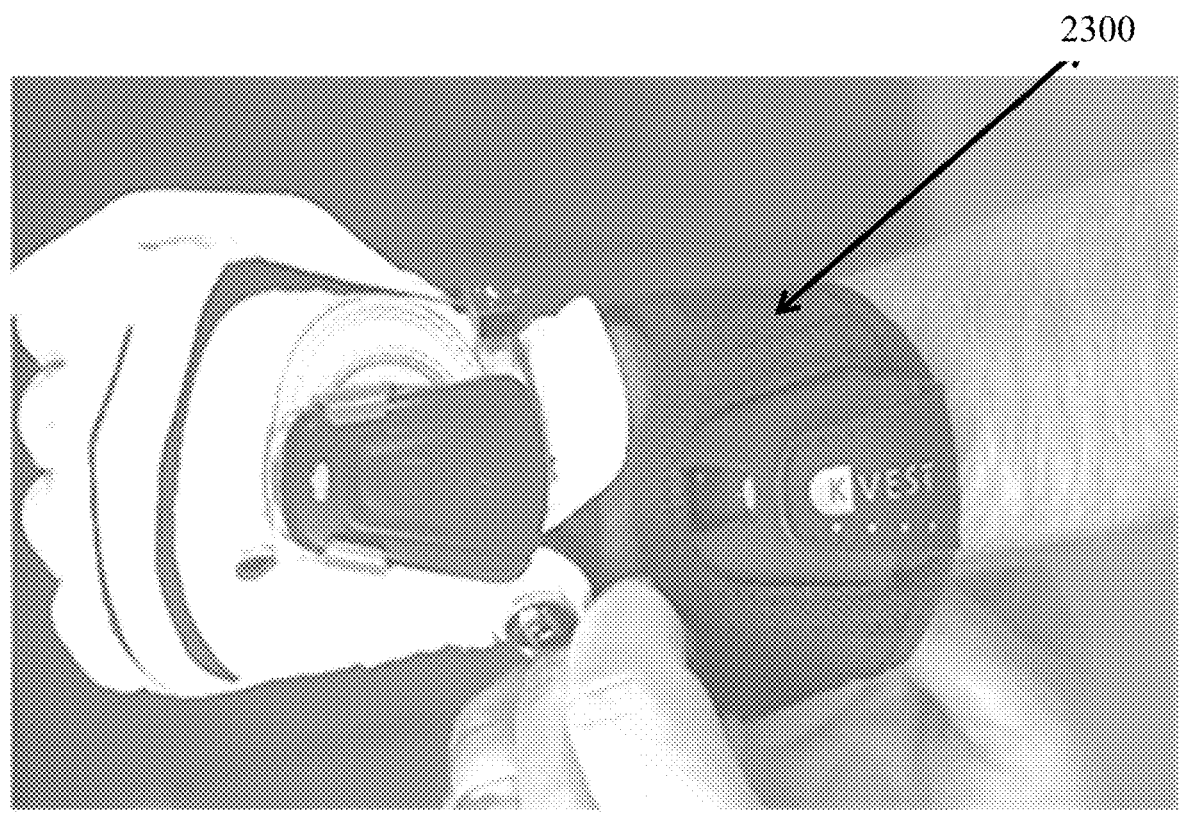
FIG. 23 is a photograph of an exemplary wrist sensor according to an embodiment of the present invention FIG. 24. is a screenshot of an animation illustrating wrist movement for an exercise during a live training session according to an embodiment of the invention.

In one or more of the foregoing embodiments, a user may be instrumented with a wrist sensor 2300 (e.g., inertial sensor) that is attached or worn on his or her wrist, such as shown in exemplary FIG. 23. The wrist sensor 2300 may be used independently of, or in conjunction with, the other body mountable sensors discussed herein. The wrist sensor 2300 may be used to capture motion data of interest relating to wrist movement, such as inertial and magnetic measurements and wrist flexion or radial/ulnar deviation. The wrist sensor 2300 may be a wrist-wearable type or a glove type sensor. For example, the wrist sensor 2300 may include one or more multi-axis accelerometers (e.g., three, six, and nine axis inertial sensors) which can capture the movements of each joint of the palm and fingers. A wrist gesture recognition may be performed with an algorithm and processing being performed in the wrist sensor 2300 itself or by a processor of the observer device 1703 and/or server 1709. The wrist sensor 2300 may be used with other instrumented sensors in order to more fully capture a motion of the arm or other body segments. For example, with respect to golf, the wrist sensor 2300 may be used in conjunction with club and ball data obtained from a launch monitor apparatus (e.g., club speed, ball speed, launch angle, spin, and azimuth). In this manner, for example, by linking wrist movement to the ball movement through wrist angles and ball launch monitors, the primary influencers of club face control are better understood and can be more accurately and dynamically coached and trained according to one or more of the above described embodiments. Moreover, this allows the user to be better connected to the ball movement and understand why how the user's swing directly affects launch parameters and ball flight.

According to an embodiment of the invention, performance indicators and real-time feedback or analysis may be provided to the user based on the wrist sensor motion data and/or wrist sensor motion data in conjunction with club and ball data obtained from the launch monitor apparatus. The feedback may be transmitted from the observer device 1903 and/or server 1909 to a user interface presented in the participant device 1901, or another display or recipient device that is configured to convey feedback to the user.

For example, the server 1909 (or observer device 1903) may be configured to generate different graphical user interfaces and display them on different computing devices described herein. As previously discussed, the server 1909 hosting the databases may comprise a processor and non-transitory machine-readable storage media comprising a set of instructions allowing the various databases to perform various tasks and processes described herein, such as to display various graphical user interfaces. Each instruction within the set of instructions may command and cause a different module of the server 1909 or processors to display a particular section or container of the graphical user interfaces described below. For example, a first instruction may instruct (e.g., command or cause) a first module of the server 1909 to query pertinent data from the exercise database 1905, participant database 1907, observer database 1913, or motion database 1915 and display a first section of a graphical user interface; and a second instruction may instruct a second module of the server 1909 to query pertinent data from a different database and display a second section of the graphical user interface. Although described herein as separate modules, it is intended that these modules can be configured as at least one module. Moreover, the server 1909 may be a database server comprising a processor capable of performing the various tasks and processes described herein. Non-limiting examples may include a server, desktop, laptop, tablet, and the like. The server 1709 may host an online service, such as cloud-computing application service, or any other service that provide web-based applications that collect data through we-based client interactions over one or more networks such as network 1911. Accordingly, the server 1909 may generate and display different graphical user interfaces on different computing devices described herein.

According to another embodiment, for example, the one or more servers 1909 include an analytics engine that further includes a data extraction module and data processing module. The analytics engine can be a software component stored on a computer readable medium and executed by a processor, e.g., as specially-programmed software on a server (referred to and used interchangeably as an analytics engine server). The analytics engine can be configured to receive user input from one or more participant devices 1901 and/or one or more observer devices 1903, receive data from a database (e.g., exercise database 1905, participant database 1907, observer database 1913, motion database 1915, etc.), produce solution data from the received user input and data, and provide the produced solution data to one or more participant devices 1901 and/or one or more observer devices 1903. Thus, for example, a user may request a report, such as an Evaluation Report, regarding the status of a particular training program, and the analytics engine may generate and present the report on different computing devices described herein.

In some embodiments, the analytics engine is implemented as a set of computer instructions executed by one or more servers 1909 that run computer executable program instructions or related algorithms.

Figure 24:
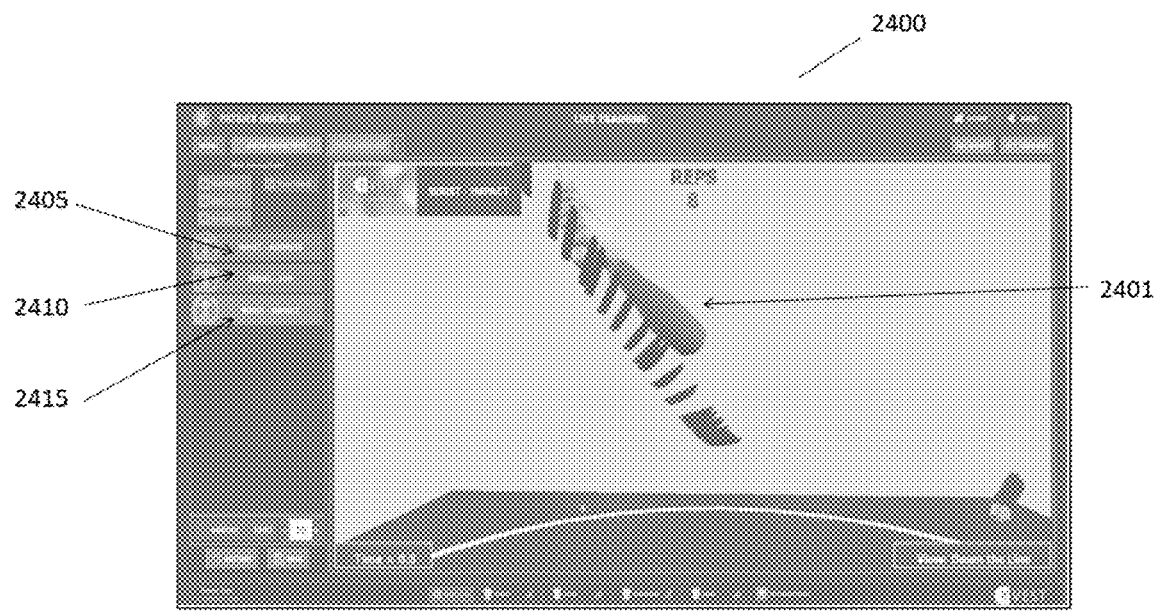
Figure 25:
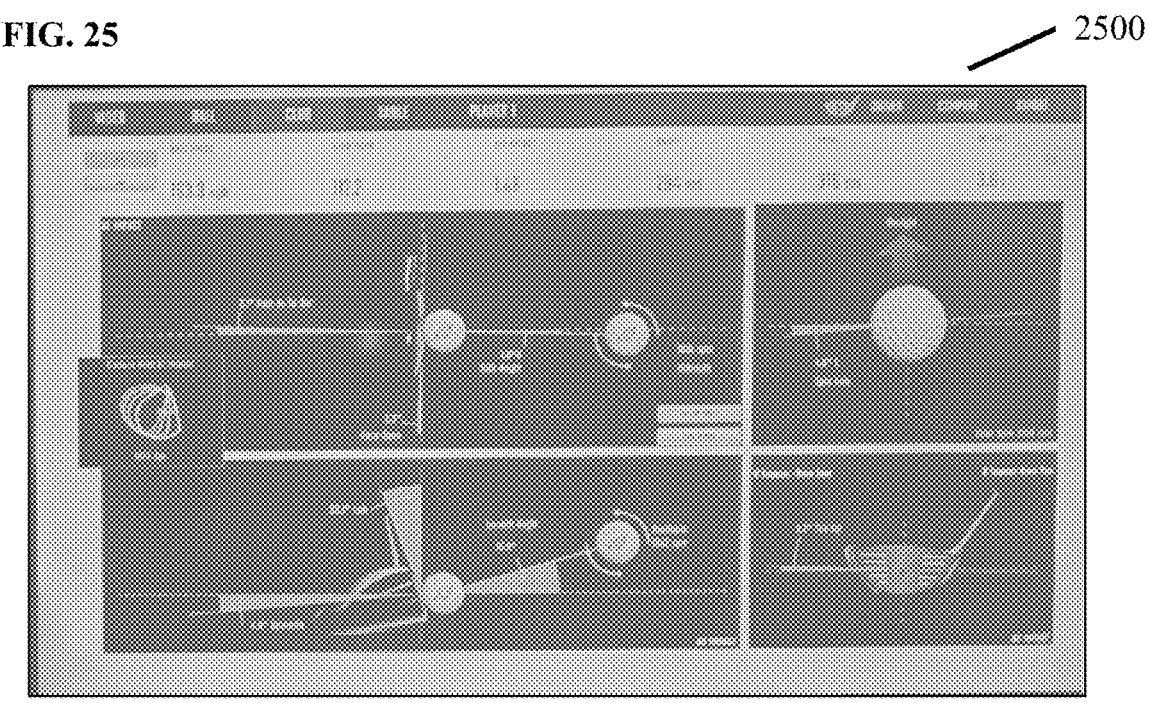
FIG. 25 is a screenshot of a graphical user interface illustrating various angles and movement of the golf club and golf ball for each swing exercise according to an embodiment of the invention.

FIGS. 24 and 25 are screenshots of exemplary graphical user interfaces generated by the server 1909 in real time during monitoring of wrist movement using one or more sensors including a wrist sensor 2300, such as describe above. The illustrated graphical interface (GUI) may be presented on one or more participant devices 1901 (e.g., computer, table computer, smart phone, or the like) and/or one or more observer devices 1903. The user interfaces may display a range of information and content and are not limited to the information and content shown in the exemplary embodiments.

Referring to FIG. 24, the screenshot 2400 shows wrist movement for an exercise during a live training session. In other words, the wrist movement shown by the animated FIG. 2401 is processed and displayed by the server 1909 (in accordance with one or more of the embodiments discussed above) in real-time during a swinging motion. Here, three biofeedback exercises are shown, which are programmed with desired ranges of wrist flexion and radial/ulnar deviation at three key points in a golf swing: Address 2405, Top 2410, and Impact 2415. The amount of time that a user must achieve wrist flexion and radial/ulnar deviation within the specified range of a given biofeedback exercise to count as a single repetition (rep) is programmable. So it is possible to set this rep time to something like 1 second for static biofeedback training of the individual swing points. When a rep of the first biofeedback exercise in the list is completed, a ding sound is played to provide audio feedback, and the next biofeedback exercise will be loaded automatically. It is also possible to set rep time to 0 seconds for dynamic biofeedback training. In this case, a user can simply perform a golf swing at regular speed. If the wrist flexion and radial/ulnar deviation is within range at each point in the swing (Address, Top, Impact) according to the three biofeedback exercises, then three ding sounds will be played and the first biofeedback exercise will become active. If, on the other hand, the user is within range for the first two biofeedback exercises, but not the third, then only two ding sounds will be played, and the third biofeedback exercise will remain active.

The multi-color animation of the animated FIG. 2401 and/or area surrounding the animated FIG. 2401 may provide for real time biofeedback to the user. For example, a red light might follow a swing in which a diagnostic parameter badly diverged from ideal and a blue light might follow a swing in which the same diagnostic parameter diverged from ideal by less than the pre-assigned margin of error. The signal light may be the background color of the animated figure or in a surrounding animation. Alternatively, segments of the avatar 2401 may change color depending on whether the selected motion is within range (e.g., red color for out of range and green color for within range). The biofeedback may likewise be presented in other audio, textual, numerical and/or graphical formats, including numbers, bar graphs, line graphs and text messages. The animation capability of the system 1900, driven by the sensor inputs, offers additional opportunities for presenting more detailed illustrations of the swing motion in real time or playback mode.

FIG. 25 is an exemplary screenshot of a graphical user interface 2500 generated by the server 1909 based on integration with a launch ball monitor apparatus, which illustrates the various angles and movement of the golf club and golf ball for each swing exercise. It is understood that the launch ball monitor apparatus can be integrated or integral with the system 1900.

Figure 26:
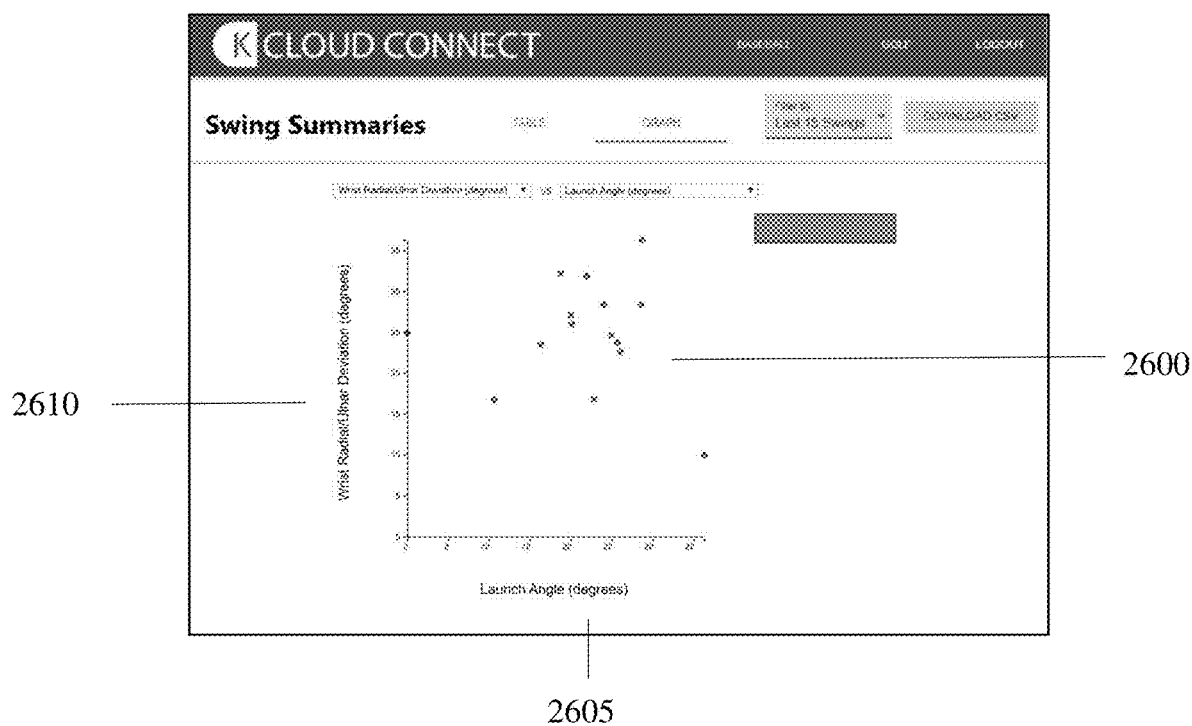
FIG. 26 is an exemplary scatterplot generated by the server that is a two-dimensional data visualization of Launch Angle (degrees) along the x-axis and Wrist Radial/Ulnar deviation (degrees) along the y-axis according to an embodiment of the invention.

FIG. 26 shows an exemplary scatterplot 2600 generated by the server 1909 that is a two-dimensional data visualization of Launch Angle (degrees) 2605 along the x-axis and Wrist Radial/Ulnar deviation (degrees) 2610 along the y-axis for the participant's last 15 swings. As discussed above, the Wrist Radial/Ulnar deviation is determined by the CPU based on sensor data from the wrist sensor 2300 and the Launch Angle is obtained from the launch ball monitor apparatus connected to the system 1900. The server 1909 retrieves the Launch Angle and Wrist Radial/Ulnar deviation data stored in one or more databases, correlates the data, and generates the scatterplot 2600 to be displayed on a display screen of the observer device 1901 and/or participant device 1903 according to one or more of the foregoing embodiments.

In one or more of the foregoing embodiments, the motion instruction system may be configured to provide/prescribe the user with an exercise or workout of the day that is based in part on the user's prior performance of various motions as assessed by the system based on diagnostic parameters from the sensor data. Such prescription can also be done autonomously through the use of a trained machine learning module or manually by an observer/coach based on the sensor data. The information may be delivered to the user via a user interface presented in the participant device 1901, or another display or recipient device that is configured to convey feedback to the user.

It is understood, for example, that the observer/coach may prescribe a workout of the day to one or more users (unlimited number of users). The prescribed workout (e.g., regime file) may be pushed to each user's participant device or provided on a website accessible by a web browser. The prescribed workout may be identical for each user, or individually customized to each user based on performance data associated with each user. In other words, each user may be prescribed the same exercise at the same time (e.g., squats for a one minute time period); however, the prescribed workout for each of the users may be customized based on performance data associated with that particular user (e.g., advanced user may be prescribed 15 squats in the one minute time period, while a novice user may be prescribed 10 squats—in this way all users in the workout are performing the same exercise at the same time).

The workout may be generated in conjunction with an auto capture system; an autonomous training system; a dynamic motion scoring and training system; and/or a training motion scoring models with machine learning algorithms system, such as described herein, as well as biofeedback. Motion data may be transmitted to the observer/coach in real time or at the conclusion of the prescribed workout so that that the trainer/coach can provide feedback or additional coaching to the user. Furthermore, performance data from one or more users can be used to generate a leaderboard, points, competitions, etc. in conjunction with the prescribed workout of the day. The system may further include a database of observers/coaches such that the user may select an observer/coach from the database based on the user's preference (e.g., gender, age, intensity of workouts, music playlists, personality, etc.). The foregoing embodiments are advantageous in that they provide for a cloud-based student monitoring platform with biofeedback learning loop embedded software for analyzing and improving the performance of an athletic motion such as a golf swing. The cloud-based student monitoring program shows the observer/coach every repetition of every player's training.

As discussed, the motion instruction system 1900 links a coach to one or more users of the system. The system 1900 is configured to automatically generate a training program based on user data (personal, biometrics, motion data, etc.) and transmit the training program to a user interface. The user can then follow the training program on site or remotely, and motion data for the prescribed exercises are sent to the coach or observer in real-time. The system 1900 provides the coach or observer with every repetition of every user's training.

Figure 27:
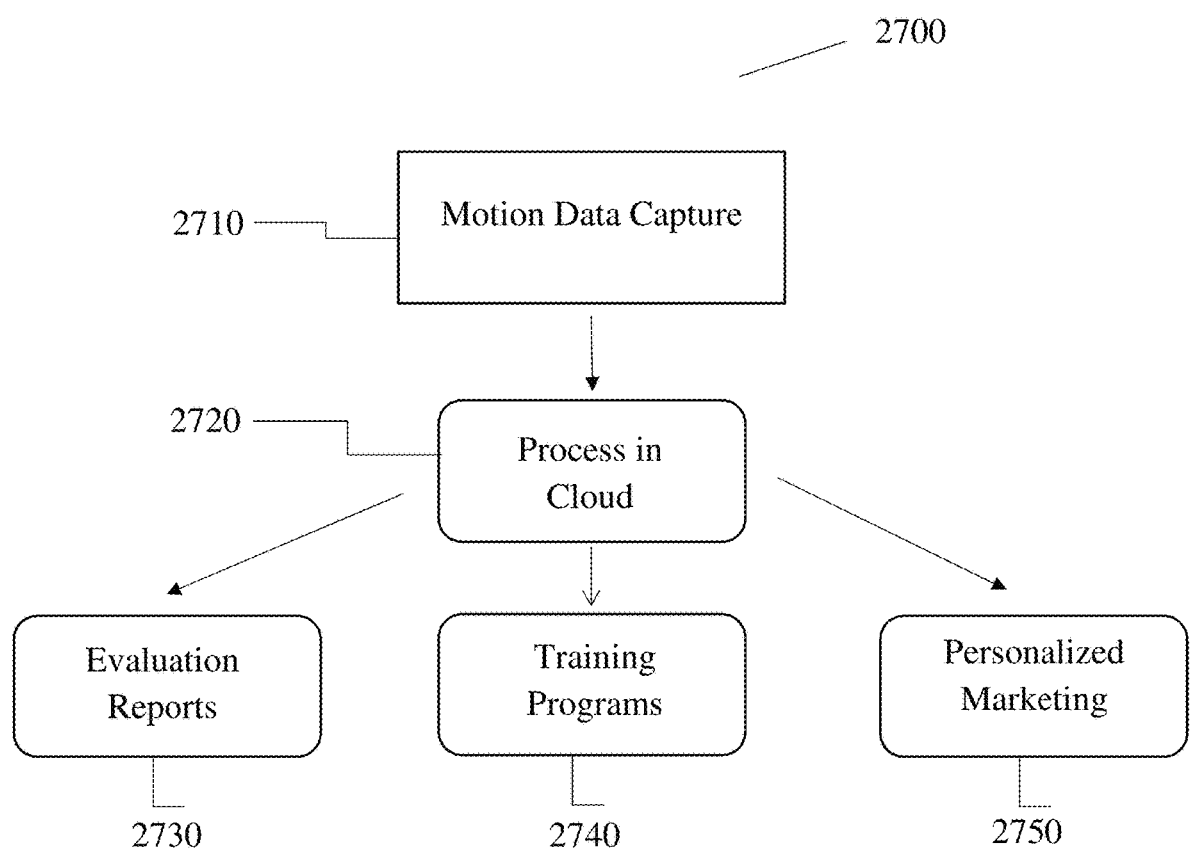
FIG. 27 is a process flowchart for a cloud-based motion instruction system according to an embodiment of the invention.

FIG. 27 illustrates an embodiment of a process flow for a cloud-based motion instruction system (e.g., "K-Cloud") in accordance with the foregoing embodiments. According to the embodiment, the cloud-based system 2700 may include one or more participant devices 1901, one or more observer devices 1903, and a server 1909 (participant device 1901, observer device 1903, and server 1909 are collectively referred to herein as the "CPU"). As discussed above, sensor data is continuously wirelessly streamed from the sensors to a transceiver of the CPU. The sensor data may be transmitted to the CPU transceiver regardless of whether any motion gesture (e.g., golf club swing, baseball bat swing, etc.) has occurred. The transmitted sensor data may be buffered in a data buffer of the CPU. Upon recognition of the motion gesture, the CPU may extract from the data buffer sensor data in which is a predetermined time window around the moment in which the gesture took place, including before the gesture was recognized. The extracted sensor data may then be processed by the CPU to generate a set of exercises for participants based on the sensor data received from the participant device 1901.

Accordingly, the system 2700 may be configured to perform: 1) a local capture process 2710 in which the CPU captures motion data, such as described above (e.g., captured motion data from wearable inertial sensors 1702*a-c*, a wrist sensor 2300, a launch monitor, video camera, radar system, etc.); and 2) cloud-processing techniques 2720 in which the captured motion data is received, analyzed, and processed by the CPU to generate one or more exercises for the participant to perform based on the sensor data, such as described above. Based on the cloud-processing techniques 2720, the CPU can generate, among other things: (a) an evaluation report 2730 based on the captured motion data to provide an objective record of the type and degree of changes in performance that the user has experienced; (b) a training program 2740 for the selected movement (e.g., swing) so that a user can be coached and trained to perform the exact captured movement with video, audio, and/or haptic cues according to one or more of the above described embodiments; and (c) personalized content marketing to deliver content or messages to the user based on the motion data and/or information provided by the user. Additionally, the cloud-based system 2700 may process information provided by the user to target advertising to users in real-time or at the conclusion of a prescribed workout across any platforms. Such advertising can be targeted based on personal data, performance characteristics, or any other data gathered by the system 2700.

In various exemplary embodiments the user (e.g., participant, observer/coach) can use a graphical user interface generated by the CPU and displayed on the participant device 1903 and/or the observer device 1901 to view and/or select a range of different information on the display. The graphical user interface can provide a wide range of control and informational windows that can be accessed by a click, touch, or gesture. Such windows may provide information about the user's own performance and/or the performance of other participants in the same who are performing the same or different activity—both past and present.

The graphical user interface may be used to access user information, login and logout of the system 2700, as well as access live training instruction and archived content. Such user information may be displayed in a variety of formats and may include past and present performance and account information, social networking links, achievements, etc. The user interface may also be used to access the system to update user profile information, manage account settings, and control participant device 1903, observer device 1901, and/or server 1909 settings.

Figure 28:
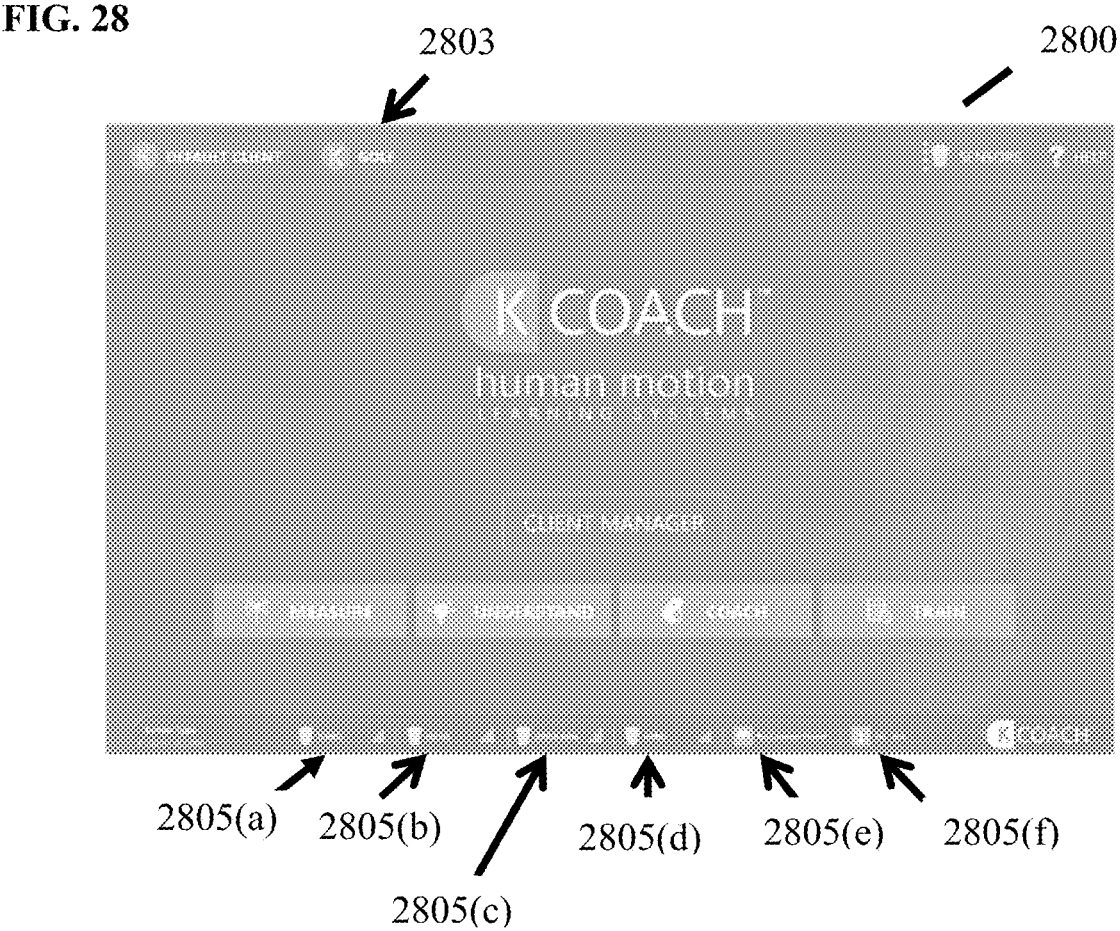
FIG. 28 is a screenshot of a graphical user interface generated by the CPU illustrating a Client Manager application according to an embodiment of the invention.

Referring to FIG. 28, a graphical user interface generated by the CPU may be displayed on the display screen of the observer device 1901 and/or participant device 1903. In this example, the graphical user interface displayed is a Client Manager screen 2800 that is directed to a coach/observer for monitoring a participant. The Client Manager screen 2800 may include an indicator 2801 that identifies the participant being monitored. Here, the name is shown as "K DEFAULT CLIENT;" however, a participant's name, such as Jane Doe, would preferably appear. The client manager screen 2800 may be used to toggle between different activity modes being monitored by the system 2700, such as golf, baseball, physical therapy, lead wrist, etc. Here, the indicator "K GOLF" 2803 at the top of the screen indicates that golf is the current motion activity being analyzed by the system 2700 so it is operating in a golf mode. The bottom tab shows sensor information (may be located anywhere on the screen). An indicator, such as a green light, denotes sensor connection with the system, e.g., a Bluetooth connection. As shown, a torso sensor 2805(a), a pelvis sensor 2805(b), an upper arm sensor 2805(c), and a hand sensor 2805(d) are connected to the system 2700 (reflected by the green indicator light); however a camera 2805(e) and a launch monitor 2805(f) are not connected (no indicator light). It is understood that the invention is not limited to the sensors and peripheral monitoring devices shown in FIG. 28. There may be more or less sensors, or different sensors and/or peripheral monitoring devices, such as, for example, a wrist sensor 2300, a club or bat mounted sensor, etc. The number and type of sensors and/or other peripheral monitoring devices that are used may be based on the activity mode and/or motion being detected and analyzed.

Figure 29:
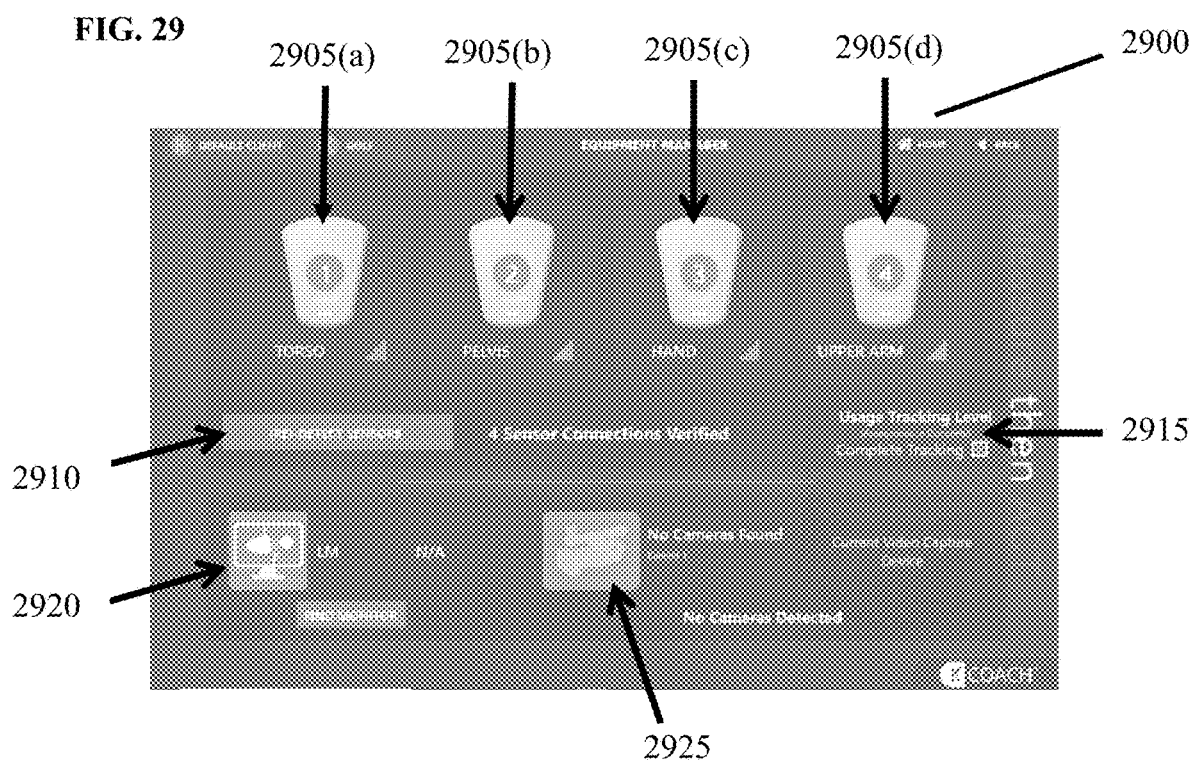
FIG. 29 is a screenshot of a graphical user interface generated by the CPU illustrating an Equipment Manager application according to an embodiment of the invention.

FIG. 29 is a screenshot of an exemplary graphical user interface generated by the CPU for an Equipment Manager screen 2900 that may be displayed on the display screen of the observer device 1901 and/or participant device 1903. The Equipment Manager screen 2900 allows the user to easily manage/control the various sensors and peripheral monitoring devices that are configured to interact with the system 2700. For example, looking at FIG. 28, at the top of the Equipment Manager screen 2900, various sensor icons are displayed, labeled, and numbered. Specifically, a first sensor icon 2905(a) is labeled "torso" and assigned number 1 (torso sensor), a second sensor icon 2905(b) is labeled "pelvis" and assigned number 2 (pelvis sensor), a third sensor icon 2905(d) is labeled "hand" and assigned number 3 (hand sensor), and a fourth sensor icon 2905(c) is labeled "upper arm" and assigned number 4 (upper arm sensor). The Equipment Manager screen 2900 includes connection indicators (e.g., green color indicating connection, no color or red color indicating no connection) for each of the four sensor icons to indicate whether or not the sensor is connected to the system 2700. Here, it is readily apparent that all four sensors are connected to the system 2700—as indicated by the respective bar symbols in green and the numbers 1-4 located on the respective sensor icons in green. The connection indicators are not limited to those shown in FIG. 29. Additionally, as shown, the graphical user interface may include a box that identifies how many of the sensors are connected to the system 2910 ("4 Sensor Connections Verified").

The graphical user interface generated for the Equipment Manager screen 2900 may further include a "(RE)-DETECT SENSORS" button 2910 that the user can press or touch to direct the system 2700 to reestablish a connection to the sensors in the event that any of the sensors are not connected to the system 2700.

The graphical user interface generated for the Equipment Manager screen 2900 may further include a "Usage Tracking Level" button 2915 that may be toggled by the user to allow the system 2700 to continually track the amount of usage of the various sensors connected thereto. As shown, the user has the option to turn off the tracking so that such sensor usage is anonymous and not tracked by the system 2700.

The graphical user interface generated for the Equipment Manager 2900 screen may further include a section for monitoring and detecting peripheral monitoring device, such as a launch monitor manager 2920 and a camera manager 2925. Similar to the "(RE)-DETECT SENSORS" button 2910 described above, the screen may include a "FIND MONITOR" button that the user can press or touch to direct the system 2700 to establish (or reestablish) a connection to with a launch monitor device. Here, the launch monitor is not connected to the system 2700.

Figure 30:
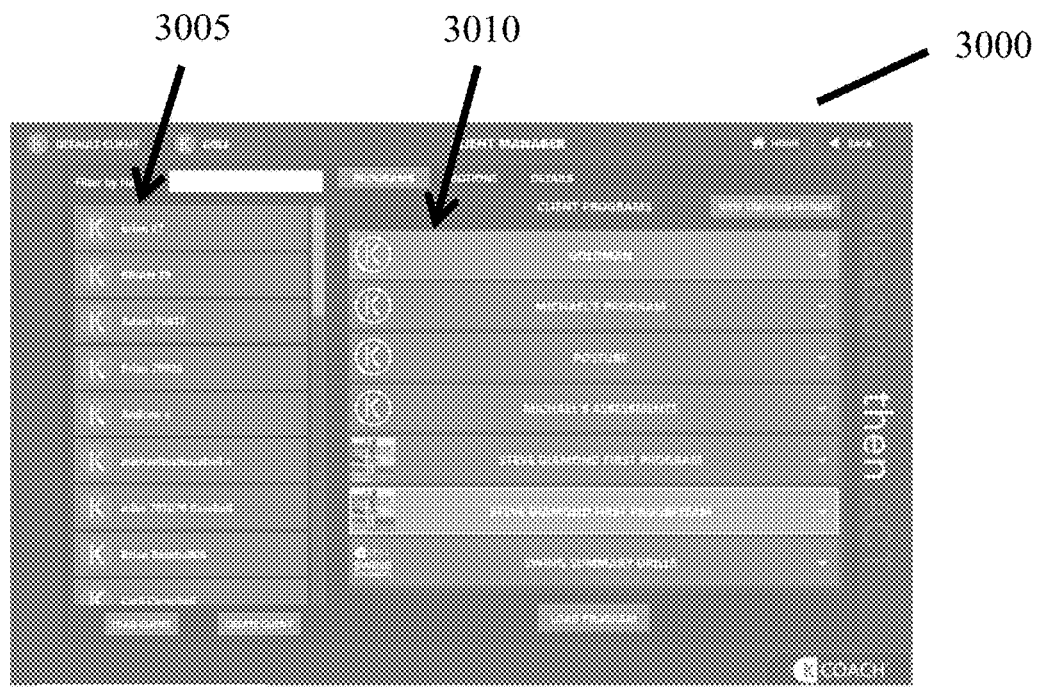
FIG. 30 is another screenshot of a graphical user interface generated by the CPU illustrating a Client Manager application according to an embodiment of the invention.
Figure 31:
FIG. 31 is another screenshot of a graphical user interface generated by the CPU illustrating a Client Manager application according to an embodiment of the invention.
Figure 32:
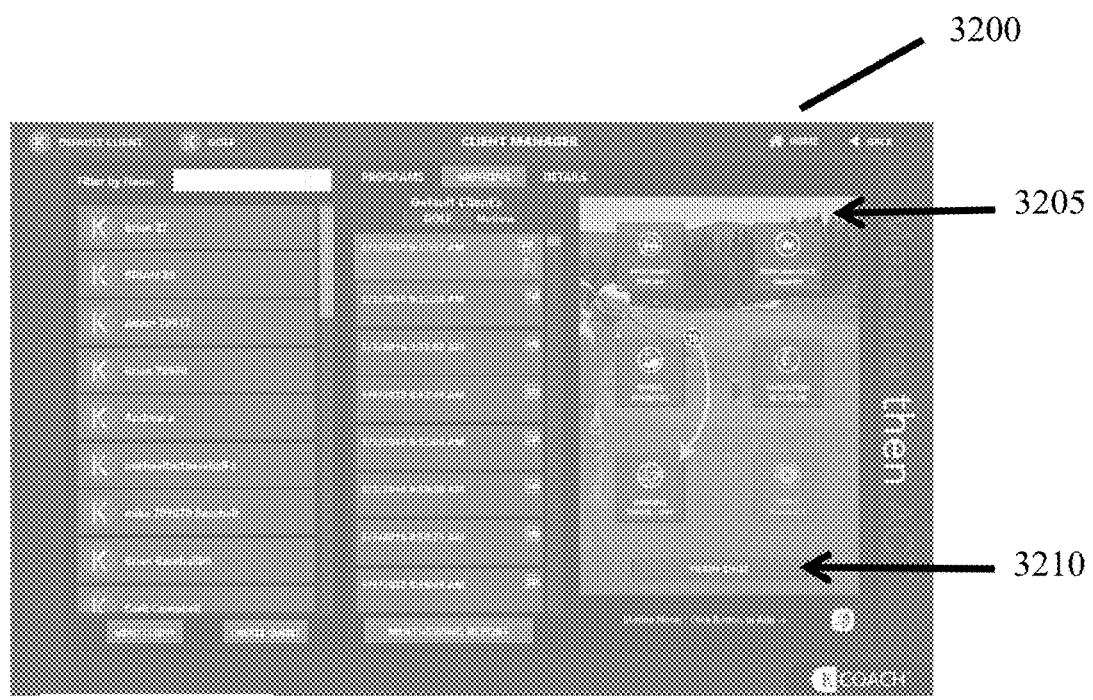
FIG. 32 is another screenshot of a graphical user interface generated by the CPU illustrating a Client Manager application according to an embodiment of the invention.

FIGS. 30-32 are screenshots of an exemplary graphical user interface generated by the CPU for a Client Manager 3000 that may be displayed on the display screen of the observer device 1901 and/or participant device 1903. The Client Manager 3000 is a central hub or portal that allows a user to manage a participant or client. For purposes of this disclosure, it is understood that participant and client are used interchangeably. The Client Manager 3000 allows the user to perform a variety of tasks, including, for example, create clients (e.g., profiles), load clients, load graphs, load reports, load animations, create training programs, train shots, view activities, compare motions to other motions stored in database, etc.

Referring to FIG. 30, this screenshot shows a list of UI elements (e.g., clickable or pressable buttons) labeled with client names 3005 ("brian 27, BRIAN 29, . . . Brian Baseball08 . . . ") and a list of UI elements labeled with client programs 3010 ("GOLDMAN, MICHAEL'S PROGRAM, POSTURE . . . SWING SUMMARY DRILLS") that the user or coach may select by pressing or clicking on the respective UI element. The Client Manager 3000 is configured to allow a single coach to easily create and load profiles for several different clients on the same computer. The user may also view a client's training history from this screen. Referring to FIG. 31, among other information, this screenshot shows a list of past swing motions 3105 captured for a selected client. As shown, each of the past swing motions may be provided as a UI element labeled with the date and time that the respective swing motion was captured that the user or coach may select by pressing or clicking on the respective UI element in order to obtain more information about the selected swing motion. Referring to FIG. 32, among other information, this screenshot shows a window 3205 with information related to a selected past training session for the selected client. As shown, each of the types of information that can be generated by the CPU related to the captured swing, including, for example, an Efficiency Report, Swing Summary, Performance Graphs, Animation Playback, Improve Swing—DVT, Video Playback (if applicable), etc., may be provided as a UI element labeled with the name of the information type to be generated that the user or coach may select by pressing or clicking on the respective UI element in order for the CPU to generate the selected information. In this example, the Default Client's golf swing motion that was captured on May 3, 2018 at 9:37:57 AM is selected and UI elements for the various types of information that may be generated by the CPU upon further user instruction are displayed. Additionally, the Client Manager 3000 may be configured to enable a user to instruct the CPU to automatically create a linked biofeedback exercise with ranges at key swing points (e.g. Address, Top of Backswing, or Impact) based on the ranges recorded for the selected motion (e.g., golf swing). For example, as shown, the graphical user interface may include a UI element called TRAIN SHOT 3210, which the user may press or click to have the CPU automatically create a linked biofeedback exercise program for the client to perform. As previously discussed, the linked biofeedback exercise program may be transmitted to one or more participant device to be viewed and accessed by the client. The Client Manager is advantageous in that it provides users with a single hub from which they can quickly launch into training or revisit past swings.

As discussed above, the system 2700 may be configured to continually monitor participant compliance or progress with a training regime and transmit information related thereto to a user, such as a coach/observer (or the participant them self), in real time. This may be done via a web portal, a mobile app, or other electronic means. FIGS. 33-36 are screenshots of an exemplary iOS mobile app that displays a participant's training progress, the mobile app having a graphical user interface generated by the CPU based on cloud-processing techniques 2720 described above. The mobile app may be accessed by a coach/observer or the participant at any time to monitor the participant's progress.

Figure 33:
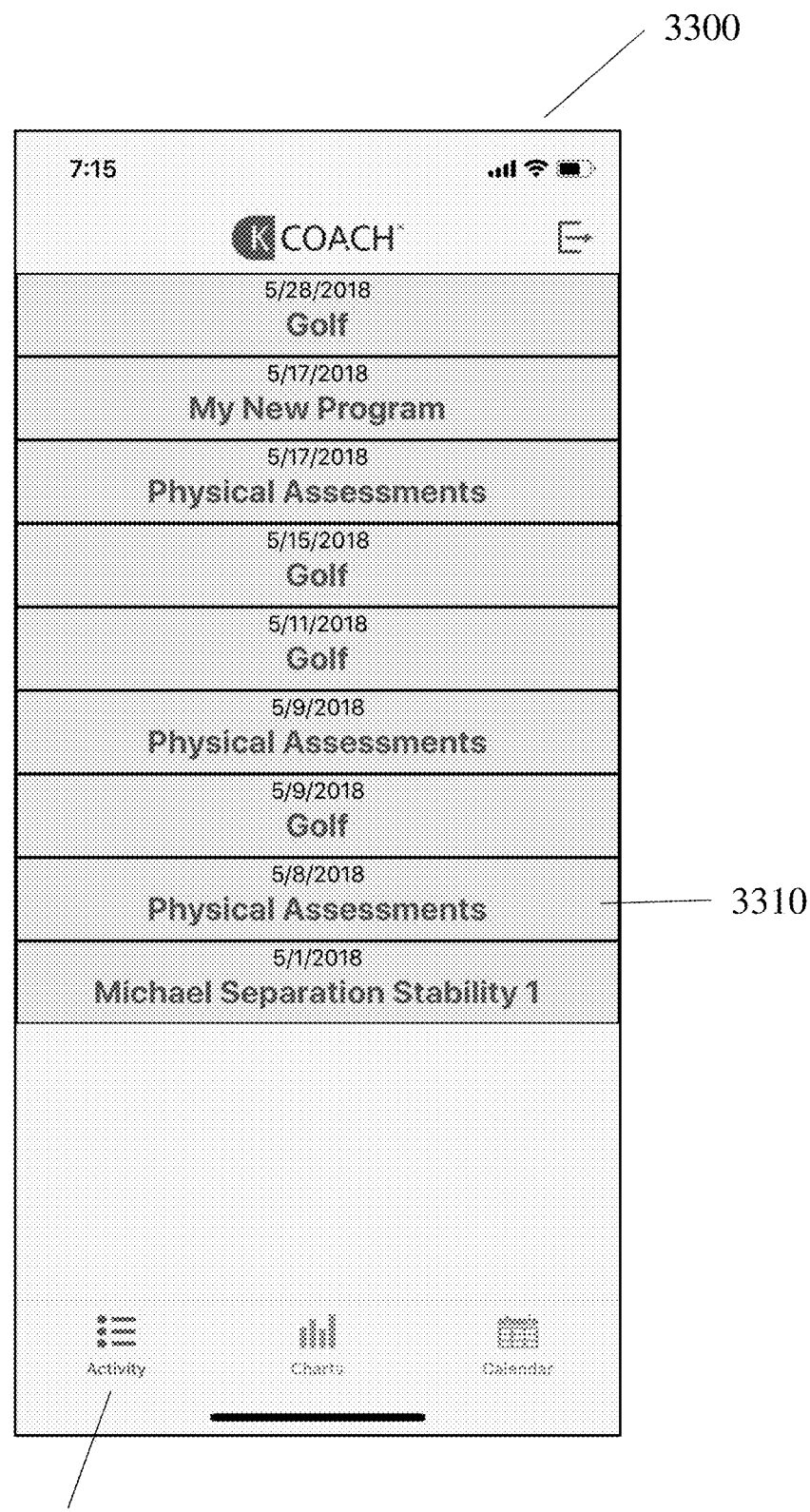
FIG. 33 is a screenshot of a graphical user interface generated by the CPU for a mobile application according to an embodiment of the invention.
Figure 34:
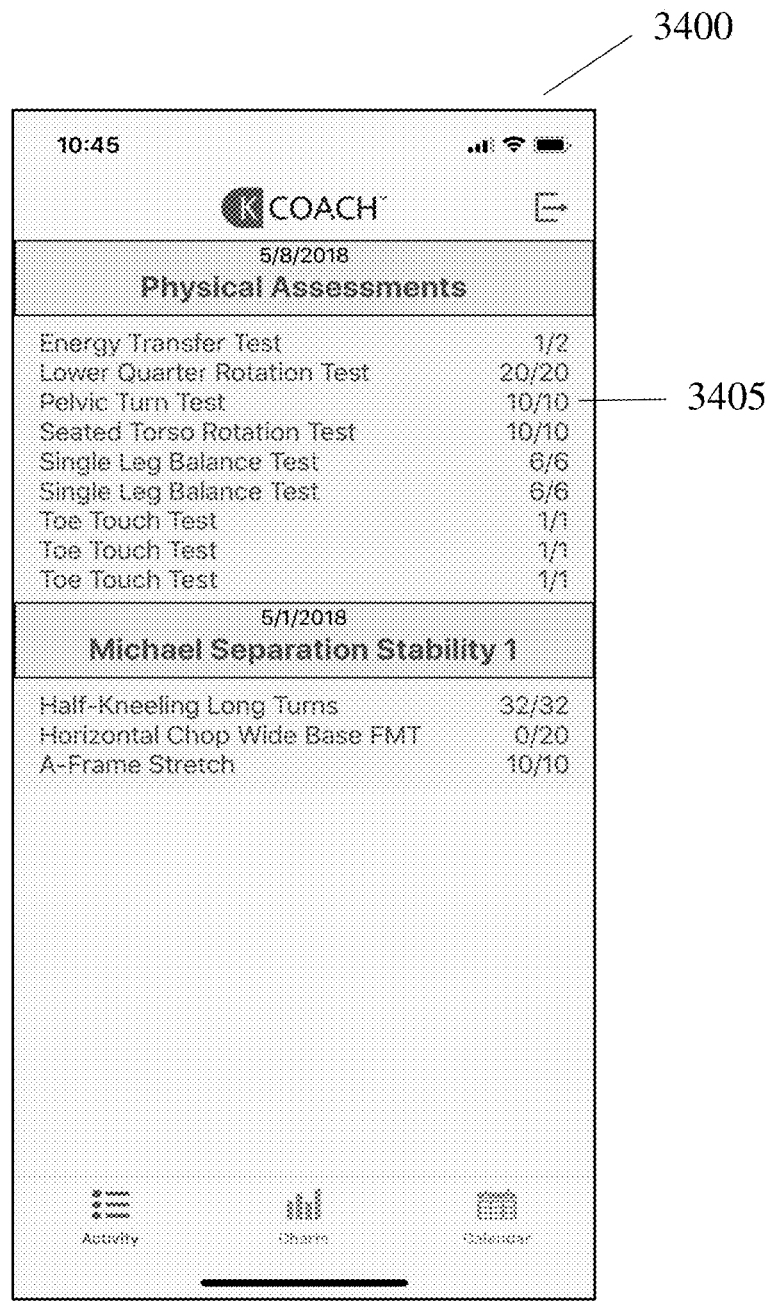
FIG. 34 is a screenshot of another graphical user interface generated by the CPU for a mobile application according to an embodiment of the invention.
Figure 35:
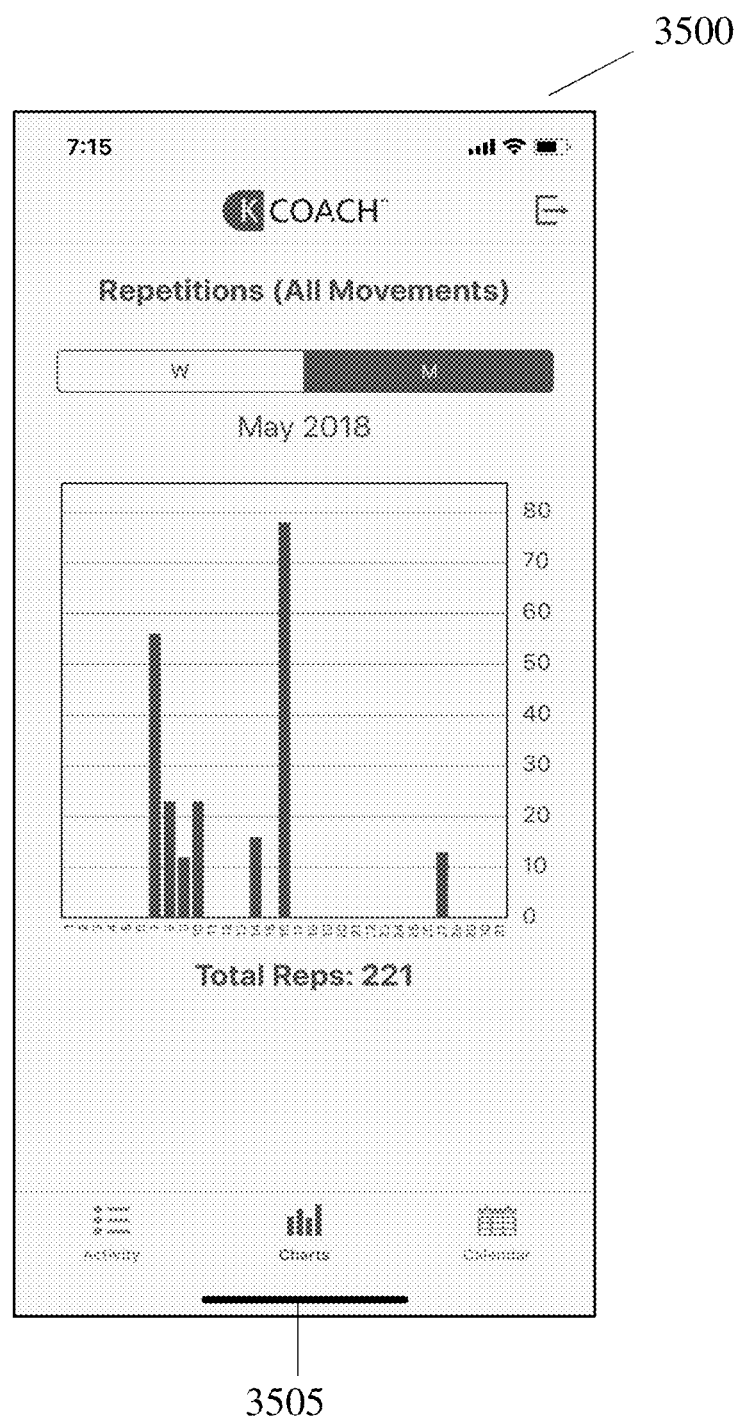
FIG. 35 is a screenshot of another graphical user interface generated by the CPU for a mobile application according to an embodiment of the invention.
Figure 36:
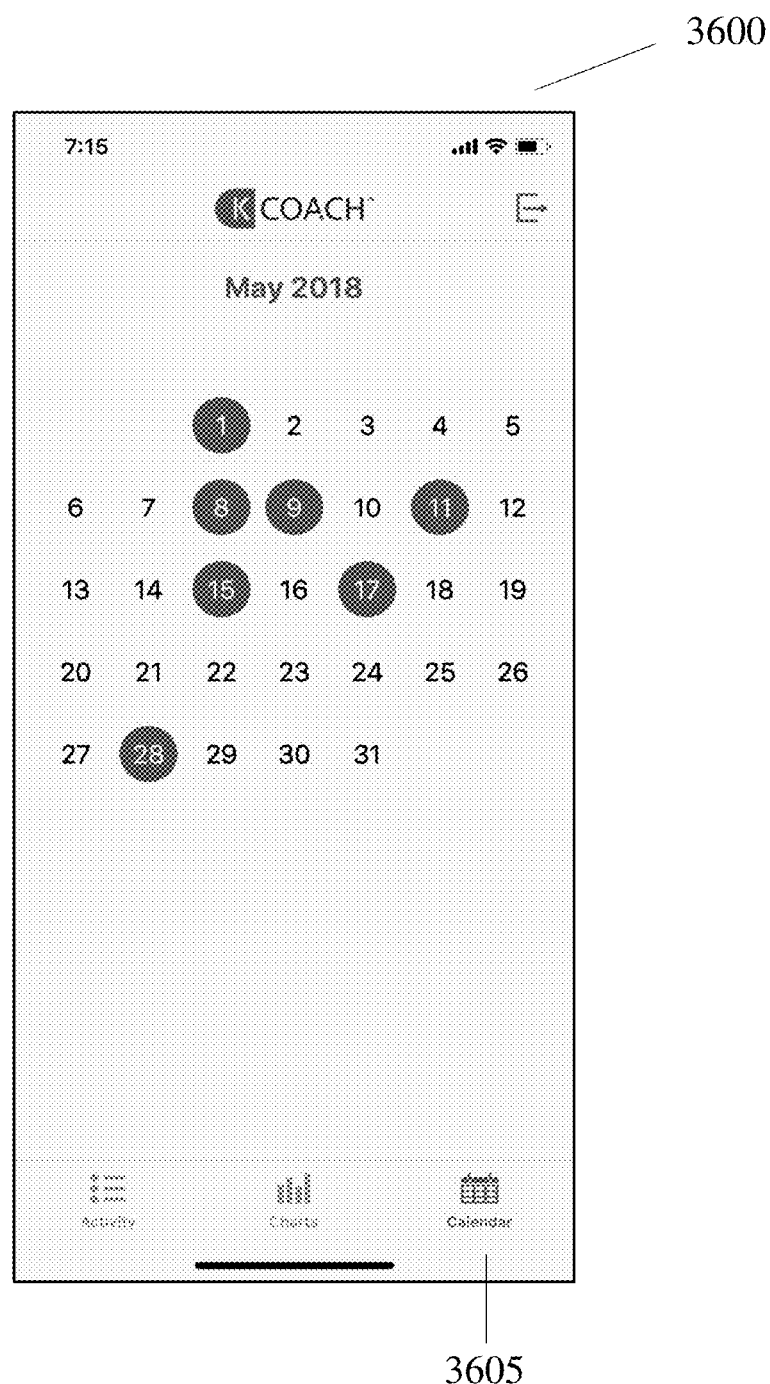
FIG. 36 is a screenshot of another graphical user interface generated by the CPU for a mobile application according to an embodiment of the invention.

In this exemplary embodiment, FIG. 33 shows an Activity screen 3300 that is available by pressing a UI element labeled Activity 3305, which is a tab located on the display. The Activity screen 3300 displays a list of UI elements consisting of any Training Programs 3310 (regimes) trained by a participant during a given time period (e.g., week or year). Each Training Program 3310 may be identified by a name and a date performed. As shown in FIG. 34, by pressing on an individual Training Program 3310 button, the list will expand it to show all component Training Activities 3405 that belong to that program (left) and number of completed reps/assigned reps (right). With this interface configuration, the user can quickly determine that the participant may need additional training with the horizontal chop wide base FMT movement since the participant successfully completed 0 out of 20 reps of that movement. FIG. 35 shows a Charts screen 3500 that is available by pressing a UI element labeled Charts 3505, which is a tab located on the display. The Charts screen 3500 may show the number of reps (for all activities) completed per day. The Charts screen 3500 may also show the total number of reps completed over a given time period (here the number is 221). In this example, the time period can be toggled by the user to either one week or one month (not limited thereto). The user may swipe left or right on the display screen to view data from different time periods, such as the prior or next week or month. FIG. 36 shows a Calendar screen 3600 that is available by pressing a UI element labeled Calendar 3605, which is a tab located on the display. The Calendar screen 3600 may show a calendar view of training. The days in which training occurred may be visually distinguishable from days in which no training occurred. Here, for example, the days in which training occurred are highlighted in green. The user may swipe left or right on the display screen to view data from different time periods, such as the prior or next week or month. In this example, the user may view data from April 2018 by swiping left on the display screen and data from June 2018 by swiping right on the display screen.

FIGS. 37-50 illustrate an embodiment of an Evaluation Report 2730 for a golf activity that is generated by the CPU in accordance with the foregoing embodiments upon the completion of a set of one or more golf swings. The Evaluation Report 2730 may be stored locally and/or in the cloud, and presented on a display of the observer device 1901 and/or participant device 1903. The Evaluation Report 2730 may be generated automatically by the CPU, or generated upon user command. As described in more detail below, the processed information is reported in a unique, synchronized, multi-format presentation of the motion data. To generate the Evaluation Report 2730, for example, the CPU can comprise a plurality of independent cores, such as a multicore processor comprising a computing component with two or more independent processing units, which are the units that read and execute program instructions, such as via multiprocessing or multithreading. The instructions are processing instructions, such as add, move data, or branch, but the cores can run multiple instructions concurrently, thereby increasing an overall operational speed for the software application, which is amenable to parallel computing. The cores can process in parallel when concurrently accessing a file or any other data structure, as disclosed herein, while being compliant with atomicity, consistency, isolation, and durability (ACID) principles, which ensure that such data structure operations/transactions, such as read, write, erase, or others, are processed reliably, such as for data security or data integrity. For example, a data structure can be accessed, such as read or written, via at least two cores concurrently, where each of the cores concurrently processes a distinct data structure record or a distinct set of data such that at least two data structure records or at least two sets of the data are processed concurrently, without locking the data structure between such cores. However, note that data locking is possible. Note that there can be at least two cores, such as two cores, three cores, four cores, six cores, eight cores, ten cores, twelve cores, or more. The cores may or may not share caches, and the cores may or may not implement message passing or shared-memory inter-core communication methods. Common network topologies to interconnect cores include bus, ring, two-dimensional mesh, and crossbar. Homogeneous multi-core systems include only identical cores, heterogeneous multi-core systems can have cores that are not identical. The cores in multi-core systems may implement architectures, such as very long instruction word (VLIW), superscalar, vector, or multithreading. In some embodiments, whether additionally or alternatively, in whole or in part, at least one of the server 1909, participant device 1901, or observer device 1903 can comprise a plurality of independent cores, such as a multi-core processor comprising a computing component with two or more independent processing units, which are the units that read and execute program instructions, such as via multiprocessing or multithreading, as disclosed herein. Such configurations may enable parallel processing of relevant information, as disclosed herein, thereby efficiently increase system computational speed.

Figure 37:
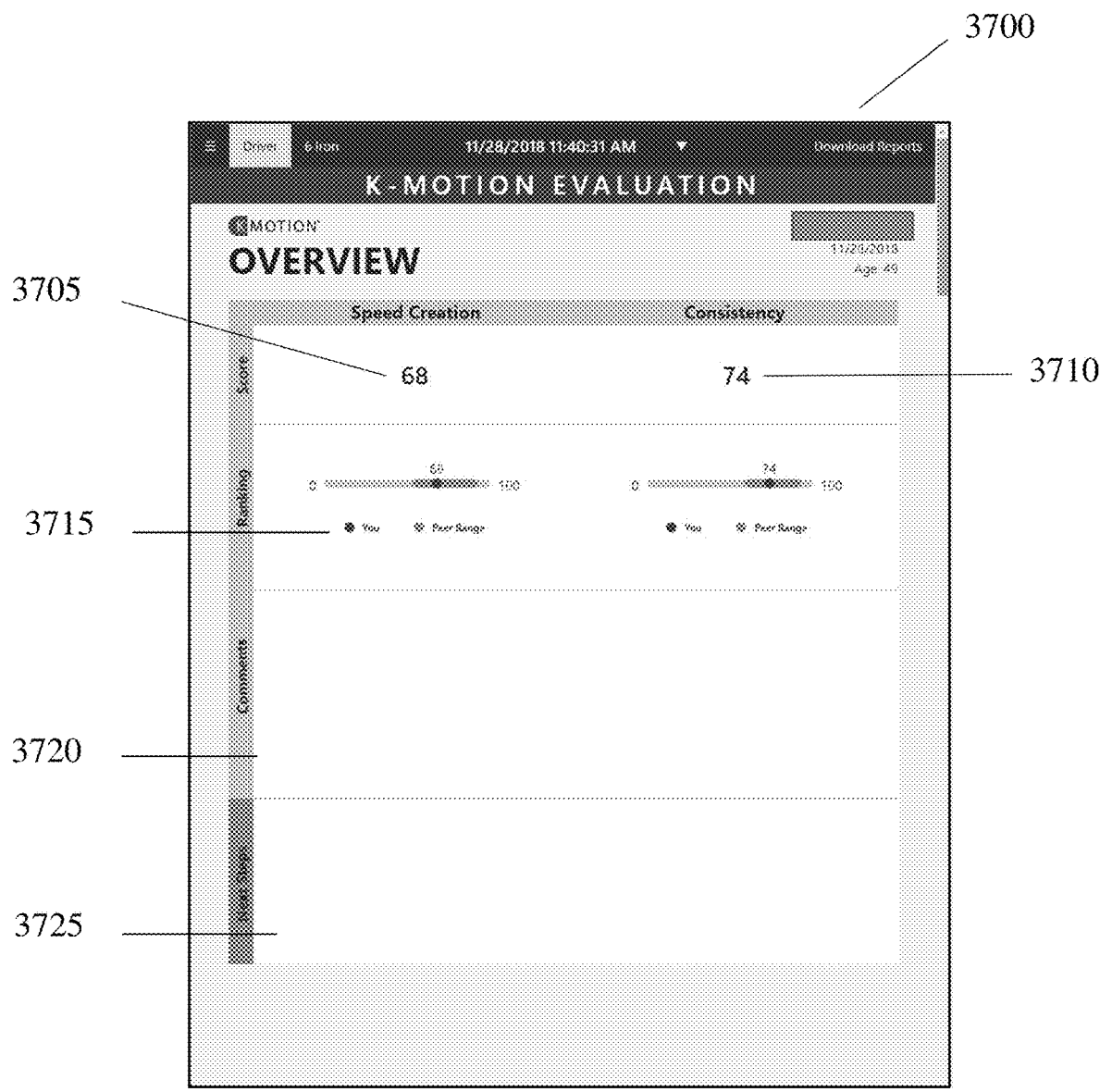
FIG. 37 is a screenshot of an Evaluation Report generated by the CPU for a golf activity according to an embodiment of the invention.

FIG. 37 is an embodiment of an Overview page 3700 that may be generated by the CPU as part of the Evaluation Report 2730. The Overview page 3700 may include a variety of general information, including the participant's name and age, and the date that the report was created. The Overview page 3700 may further include a Speed Creation Score 3705, a Consistency Score 3710, a Visualization 3715, a Comments field 3720, and/or a Next Steps field 3725 (not limited thereto). The Speed Creation Score 3705, the Consistency Score 3710, and the Visualization 3715 may be automatically generated by the CPU in accordance with one or more of the foregoing embodiments.

The Speed Creation Score 3705 is a measurement of how well the participant can create club speed with his or her body relative to a database of thousands (or more) male and female golfers of all ages. Because club speed is generated from the ground up, greater weight may be applied to the speed of body segments that are closer to the club (pelvis <torso <upper arm <lower arm <hand). In this example, the Speed Creation Score 3710 is 68.

The Consistency Score 3710 is a measurement of how consistent the participant's golf swing is in terms of both body angles and timing relative to a database of thousands (or more) male and female golfers of all ages. The body angles component measures variability of pelvis and torso angles at address, top, and impact, while the timing component measures variability of backswing and downswing times. The overall body angles component and timing component may be weighted equally by the CPU. In this example, the Consistency Score is 74.

The Visualization 3715 shows how the participant's score ranks against the range of scores for other players in his or her peer group (e.g., same gender and age group). The Text Field 3720 is a text field where a user (e.g., coach) can enter his or her comments on the Evaluation results. The Next Steps Field 3725 is a text field where a user (e.g., coach) may enter recommended next exercises for the participant to perform based on the evaluation results. The comments entered into the Text Field 3720 and/or Next Steps Field 3725 may be processed by the CPU and stored in one or more databases of the system 2700.

Figure 38:
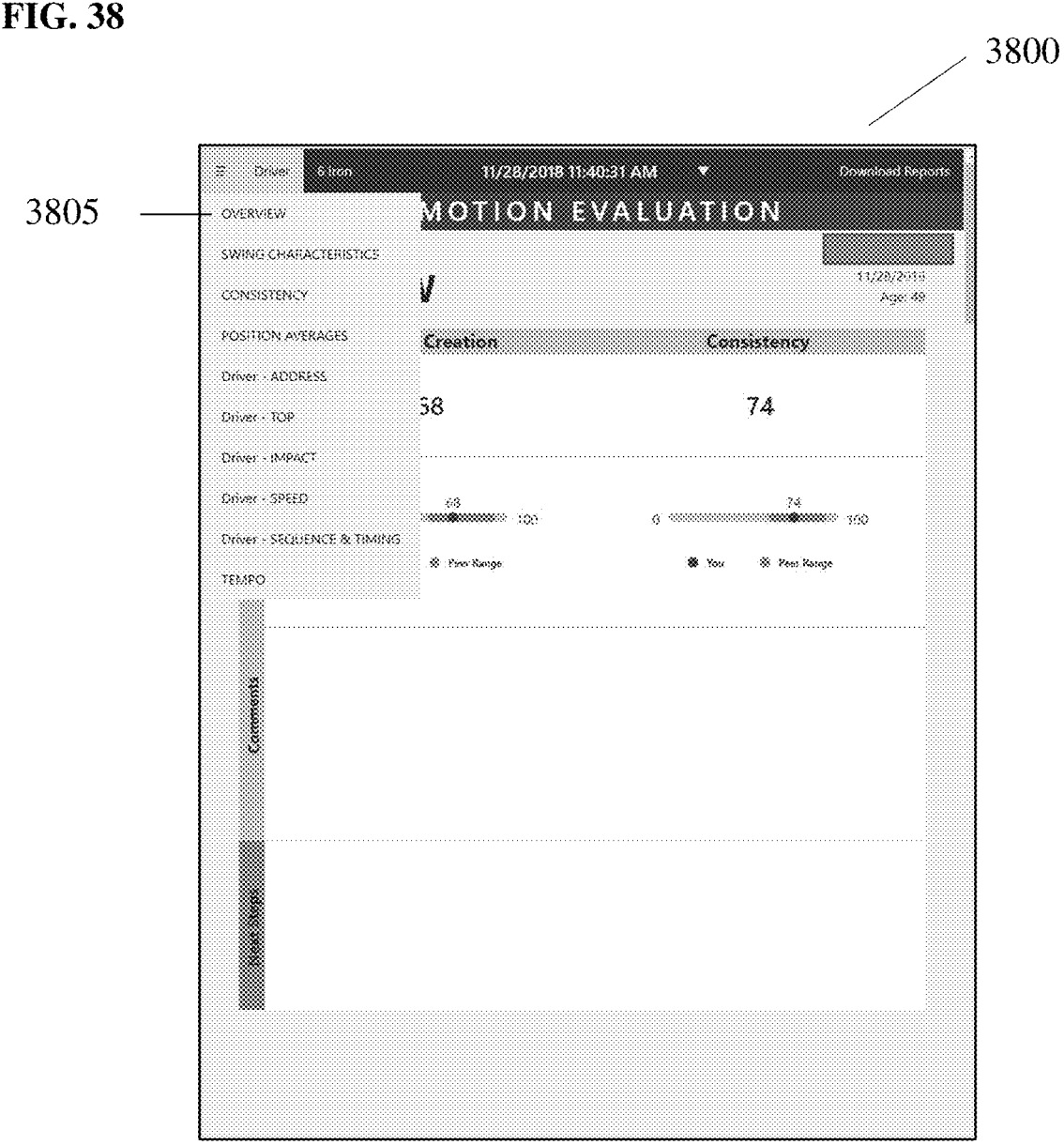
FIG. 38 is another screenshot of an Evaluation Report generated by the CPU for a golf activity according to an embodiment of the invention.
Figure 39:
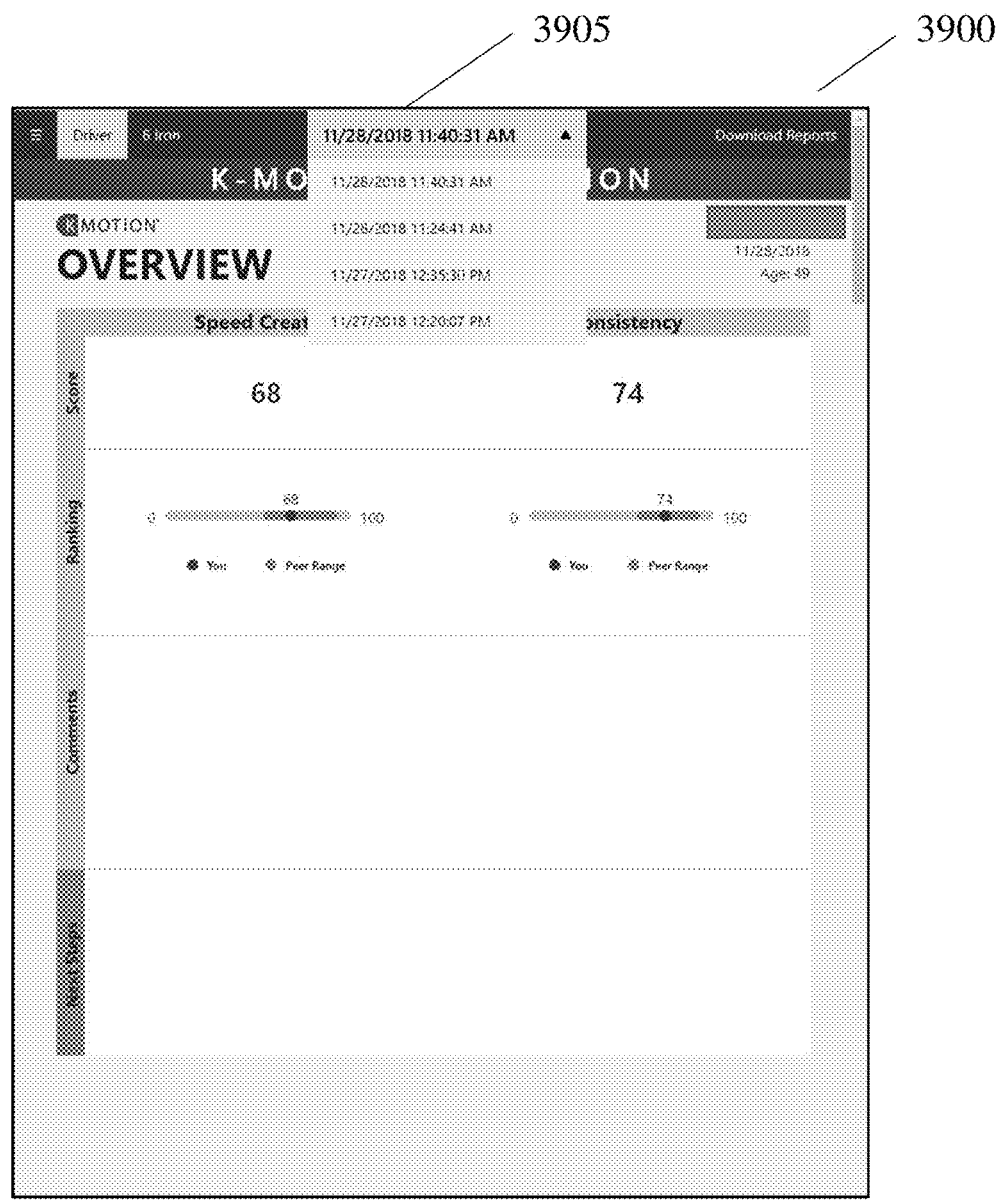
FIG. 39 is another screenshot of an Evaluation Report generated by the CPU for a golf activity according to an embodiment of the invention.
Figure 40:
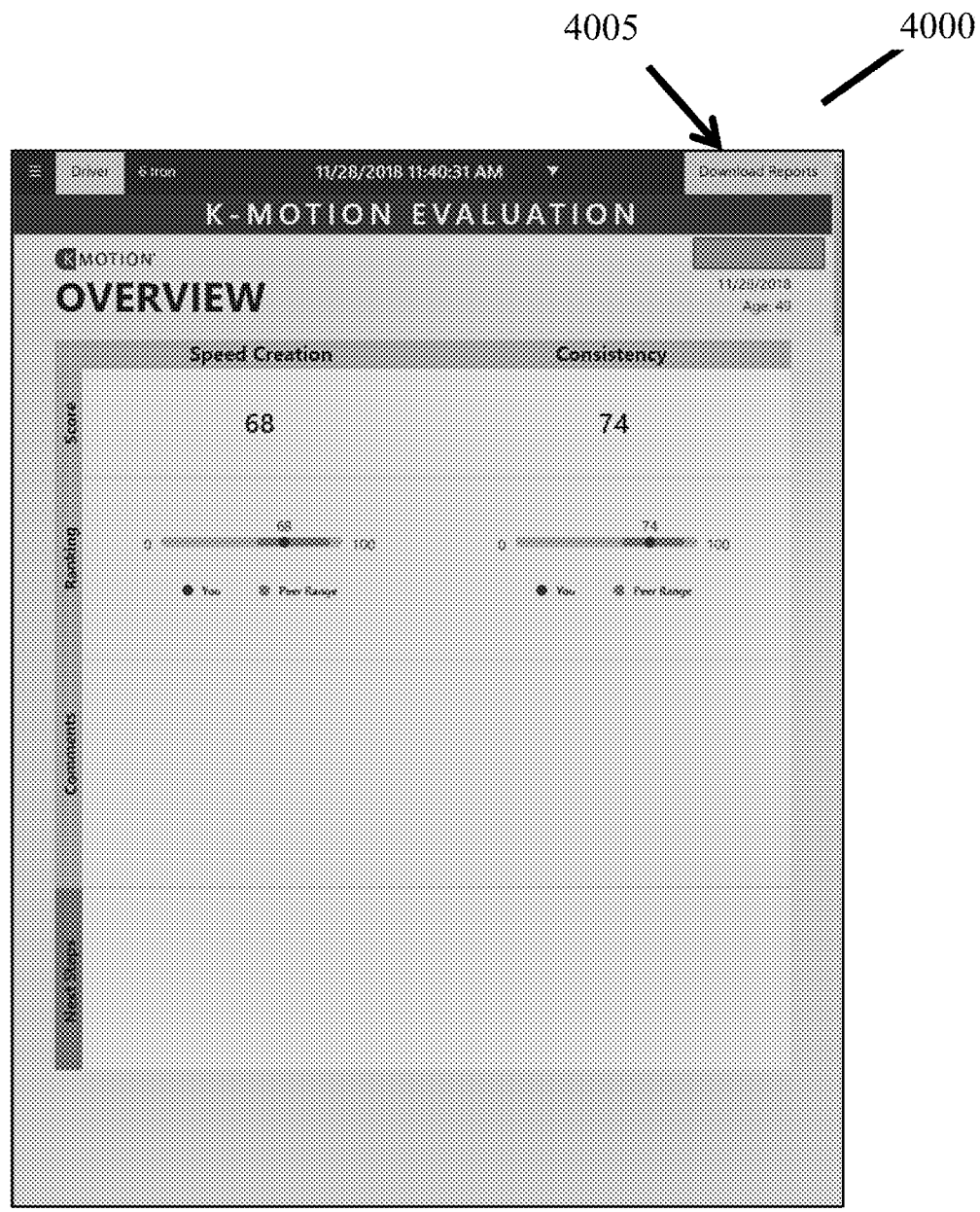
FIG. 40 is another screenshot of an Evaluation Report generated by the CPU for a golf activity according to an embodiment of the invention.
Figure 41:
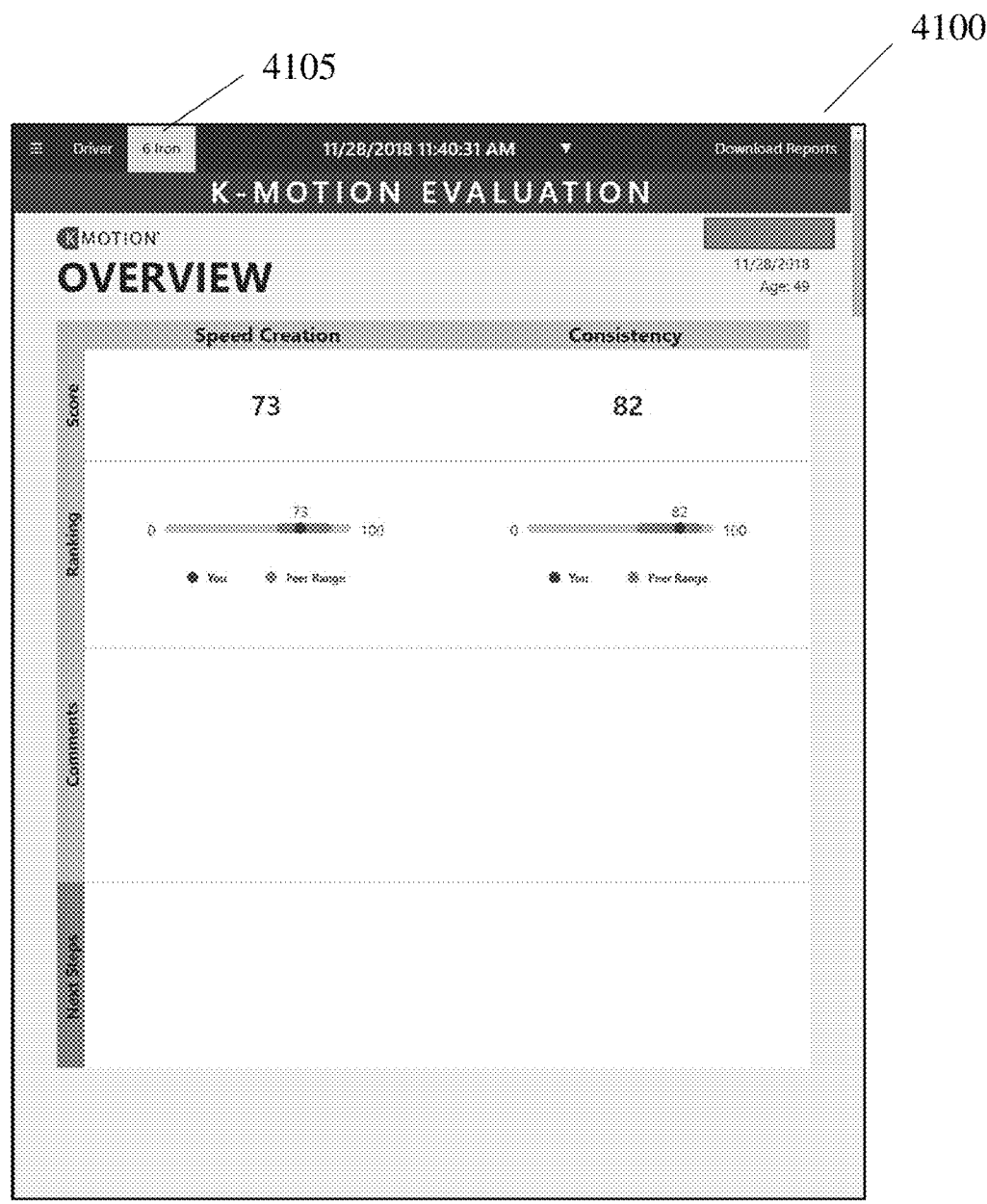
FIG. 41 is another screenshot of an Evaluation Report generated by the CPU for a golf activity according to an embodiment of the invention.

As shown in FIG. 38, the Overview 3700 report may include a menu tab 3805 that provides a drop down navigation menu that allows the user to easily navigate to different pages or reports in the Evaluation Report 2730 with a single click or touch. As shown in FIG. 39, the Overview 3700 report may include a past evaluations tab 3905 that provides a drop down menu that lists past Evaluations that have been captured for the current participant. Clicking or pressing on any of the items in the drop down menu will update the Evaluation Report 2730 accordingly. As shown in FIG. 40, the Overview 3700 report may include a Download Reports button 4005 that the user may click or press to have the CPU download the entire Evaluation Report 2730 in a single document, such as PDF format, for easy sharing. As shown in FIG. 41, the Overview 3700 report may include a club tab 4105 that the user may click or press in order to have the report generated with respect to a particular club used by the participant. For example, this Evaluation Report 2730 capture consists of five shots with a 6 Iron and five shots with a Driver. By default, data for the Driver is shown. However, by clicking or pressing on the club tab 4110, the user may update the Evaluation Report 2730 to show data for the 6 Iron.

Figure 42:
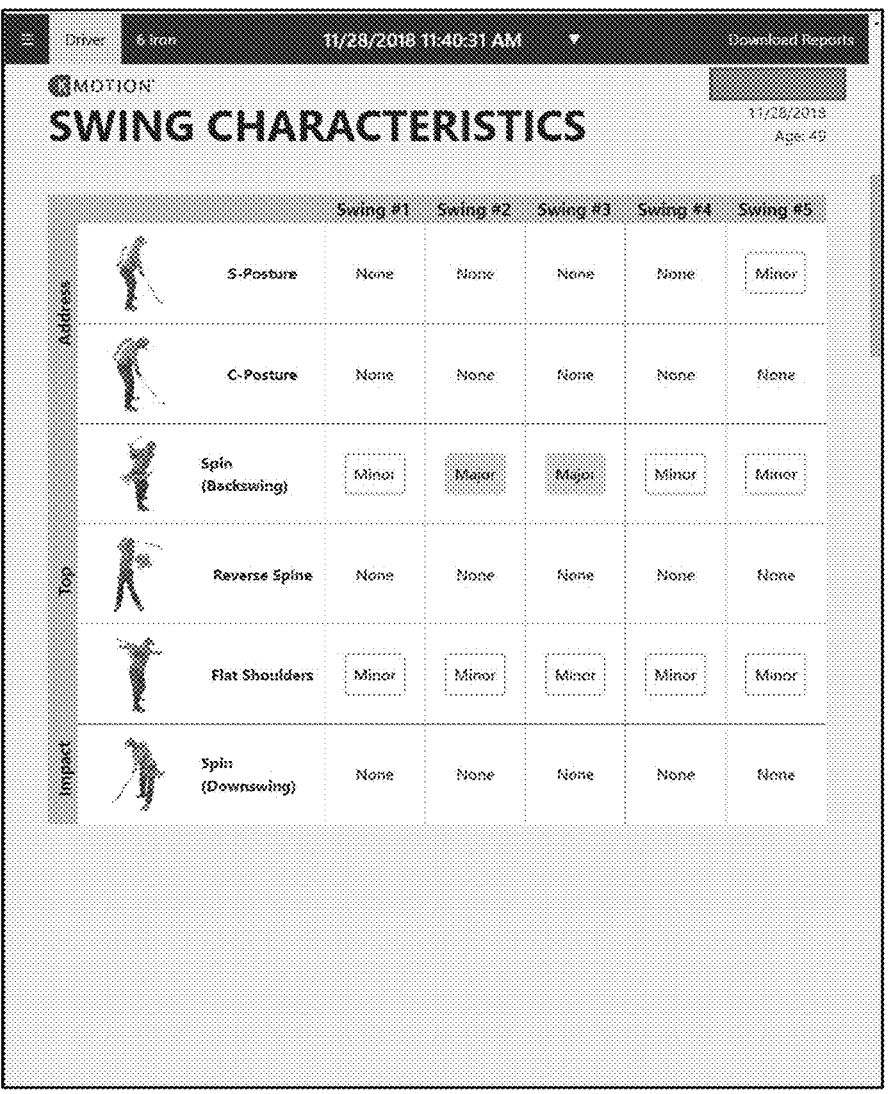
FIG. 42 is another screenshot of an Evaluation Report generated by the CPU for a golf activity according to an embodiment of the invention.

FIG. 42 is an embodiment of a Swing Characteristics 4200 report that may be generated by the CPU as part of the Evaluation Report 2730. The CPU automatically computes the severity of specific swing characteristics for each swing in an evaluation capture, and presents them on the display in accordance with one or more of the foregoing embodiments. In this example, the swing characteristics include "S-Posture" and "C-Posture" during an Address point of the swing; "spin (backswing)," "reverse spine," and "flat shoulders" during a Top portion of the swing; and "spin (downswing)" during an Impact portion of the swing. For each swing characteristic, the CPU automatically computes whether the movement was within a predetermined range, and then assigns each movement as "None" if the movement is determined to be within the predetermined range (no further training necessary), "Minor" if the movement is determined to be outside of the predetermined range but within an acceptable tolerance (may require further training); and "Major" if the movement is determined to be outside of an acceptable threshold of the predetermined range (requires further training and/or training modification).

Figure 43:
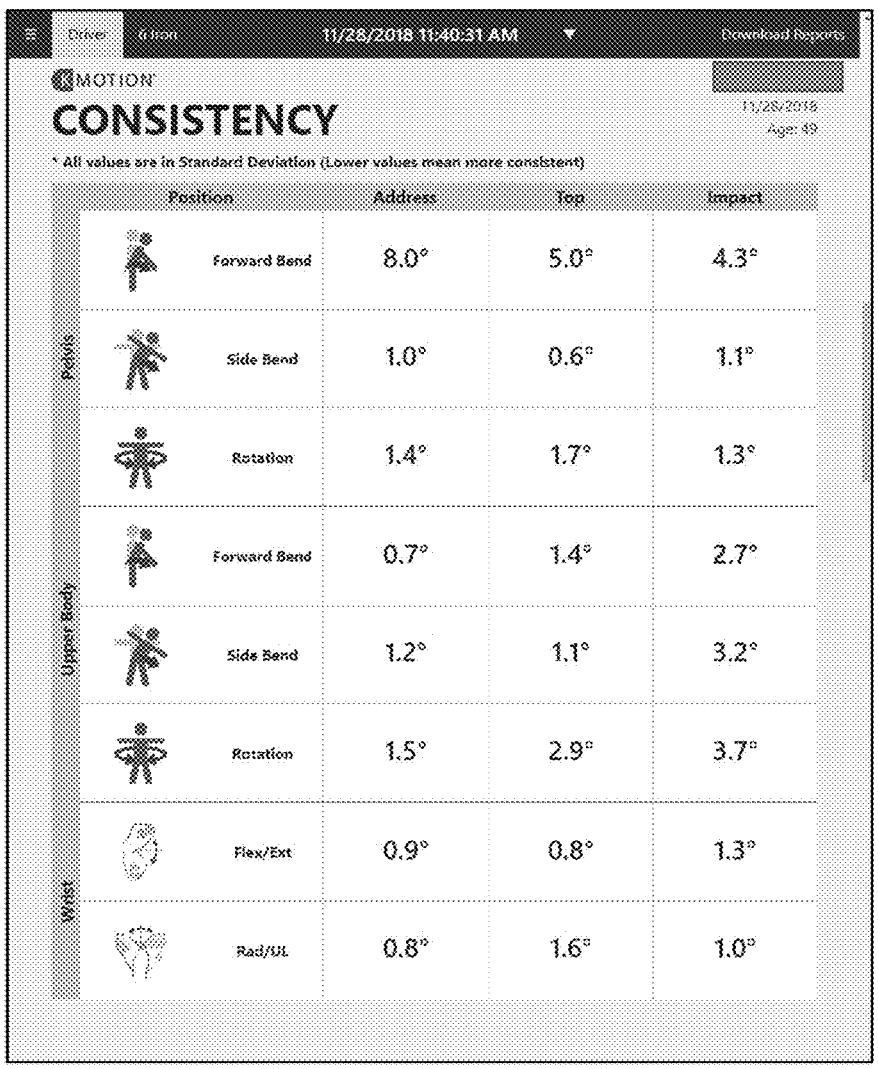
FIG. 43 is another screenshot of an Evaluation Report generated by the CPU for a golf activity according to an embodiment of the invention.

FIG. 43 is an embodiment of a Consistency 4300 report that may be generated by the CPU as part of the Evaluation Report 2730. Here, for example, the CPU may automatically compute the standard deviation of measured 3D body angles at key swing points (Address, Top, Impact) across all Evaluation swings and present the resultant information on the display as shown in accordance with one or more of the foregoing embodiments.

Figure 44:
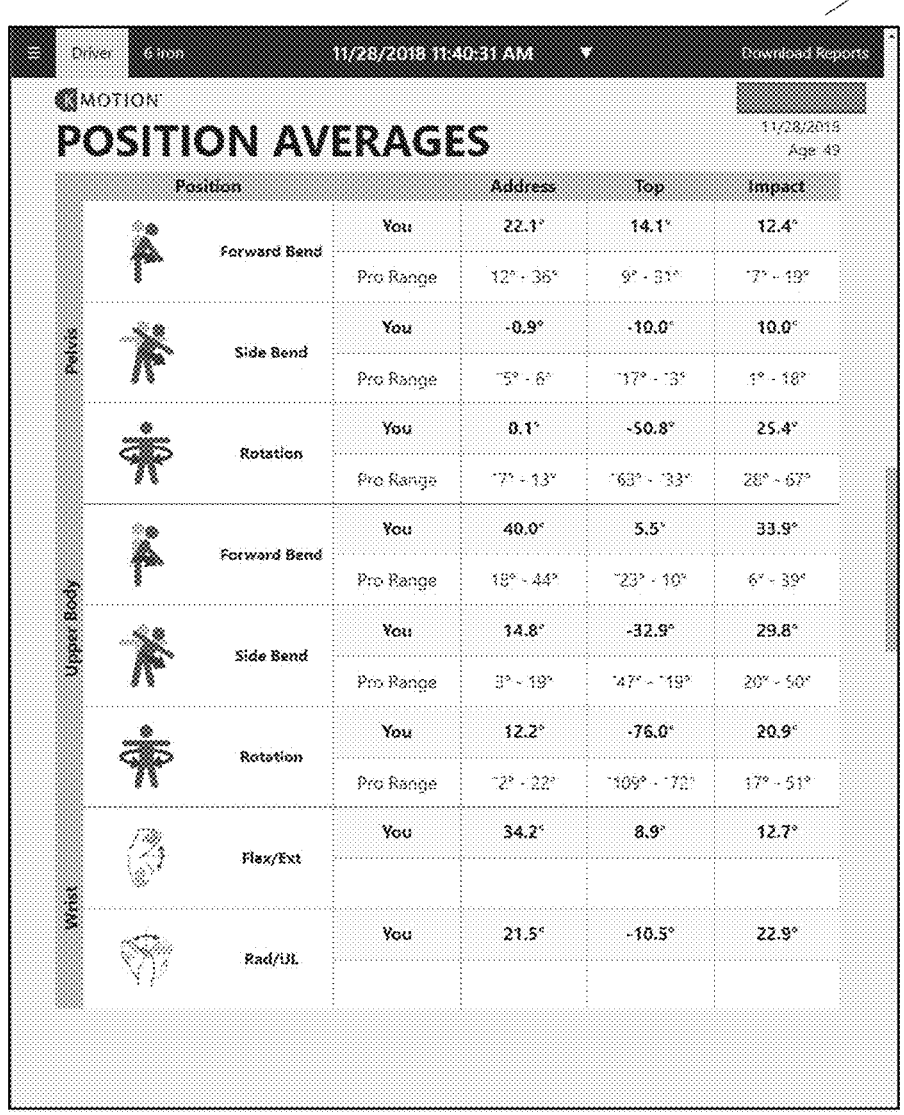
FIG. 44 is another screenshot of an Evaluation Report generated by the CPU for a golf activity according to an embodiment of the invention.

FIG. 44 is an embodiment of a Position Averages 4400 report that may be generated by the CPU as part of the Evaluation Report 2730. Here, for example, the CPU may automatically compute the averages of measured 3D body angles at key swing points (Address, Top, Impact) across all Evaluation swings and corresponding ranges for Pro players and present the resultant information on the display as shown in accordance with one or more of the foregoing embodiments.

Figure 45:
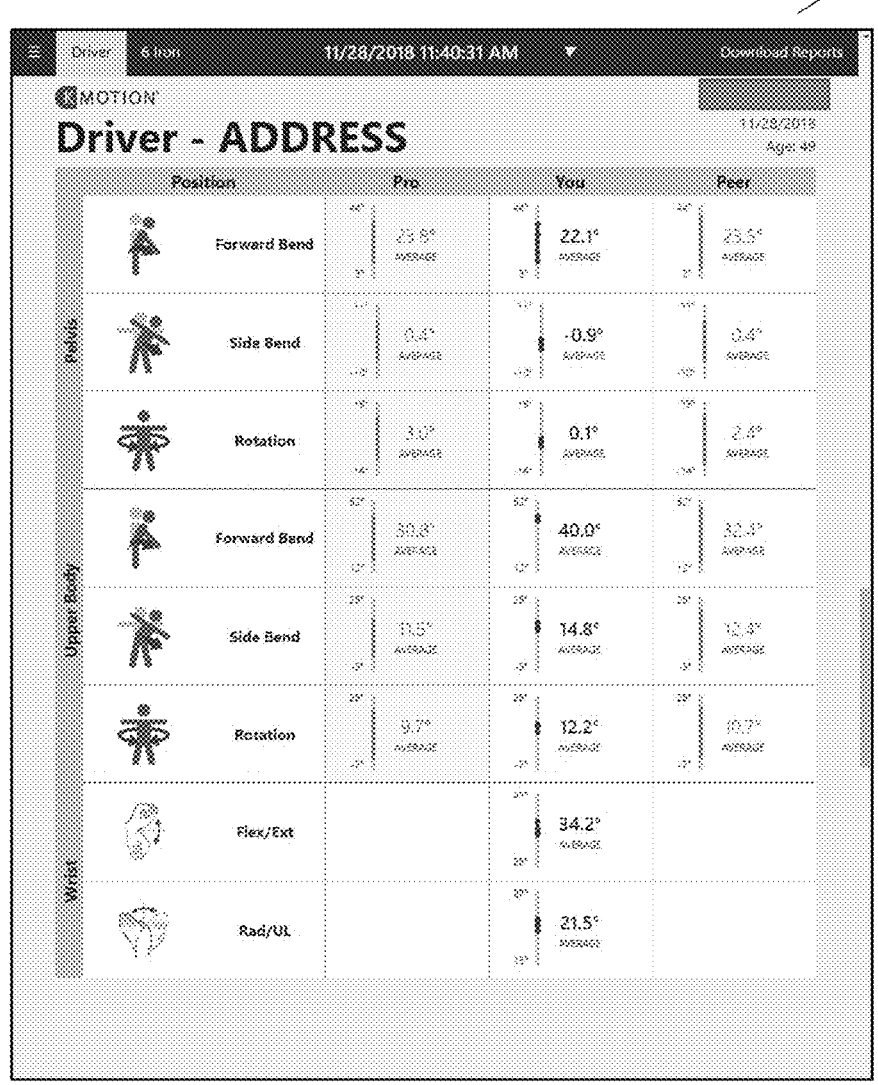
FIG. 45 is another screenshot of an Evaluation Report generated by the CPU for a golf activity according to an embodiment of the invention.

FIG. 45 is an embodiment of a Driver—Address 4500 report that may be generated by the CPU as part of the Evaluation Report 2730. Here, for example, the CPU may automatically generate a 1D plot of measured 3D body angles at single key swing point (Address) for each captured Evaluation swing (center), corresponding Pro range (left), and Peer range (right), and present them on the display as shown in accordance with one or more of the foregoing embodiments.

Figure 46:
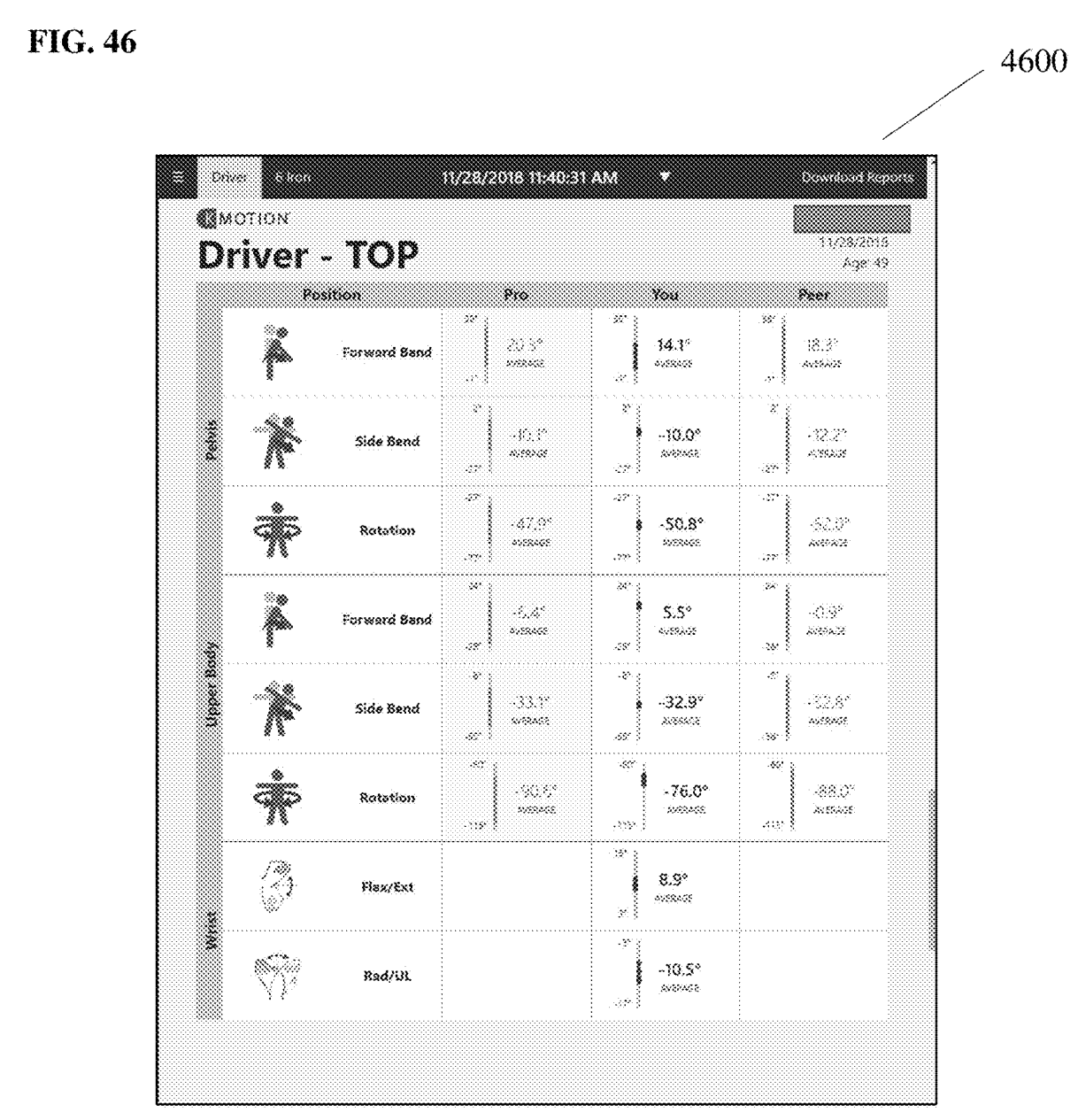

FIG. 46 is an embodiment of a Driver—Top 4600 report that may be generated by the CPU as part of the Evaluation Report 2730. Here, for example, the CPU may generate a 1D plot of measured 3D body angles at single key swing point (Top) for each captured Evaluation swing (center), corresponding Pro range (left), and Peer range (right), and present them on the display as shown in accordance with one or more of the foregoing embodiments.

Figure 47:
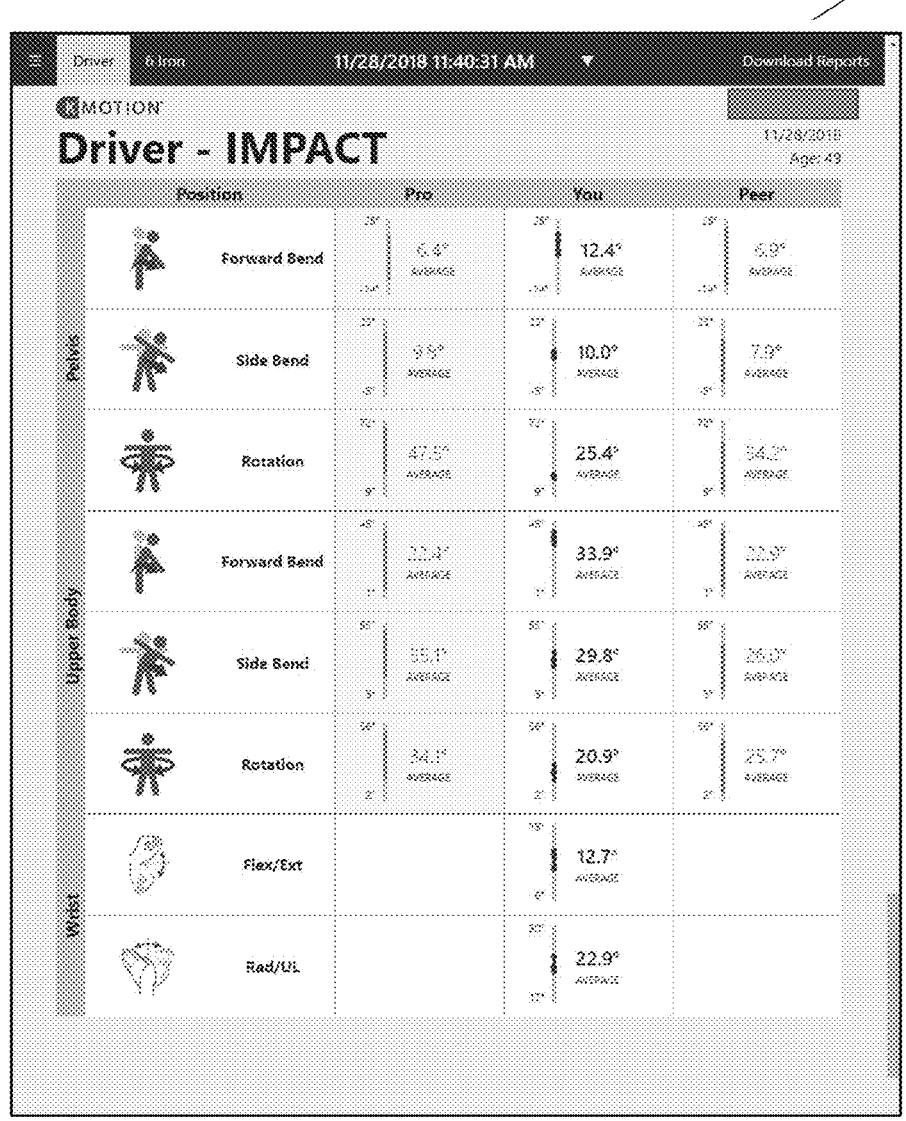
FIG. 47 is another screenshot of an Evaluation Report generated by the CPU for a golf activity according to an embodiment of the invention.

FIG. 47 is an embodiment of a Driver—Impact 4700 report that may be generated by the CPU as part of the Evaluation Report 2730. Here, for example, the CPU may generate a 1D plot of measured 3D body angles at single key swing point (Impact) for each captured Evaluation swing (center), corresponding Pro range (left), and Peer range (right), and present them on the display as shown in accordance with one or more of the foregoing embodiments.

Figure 48:
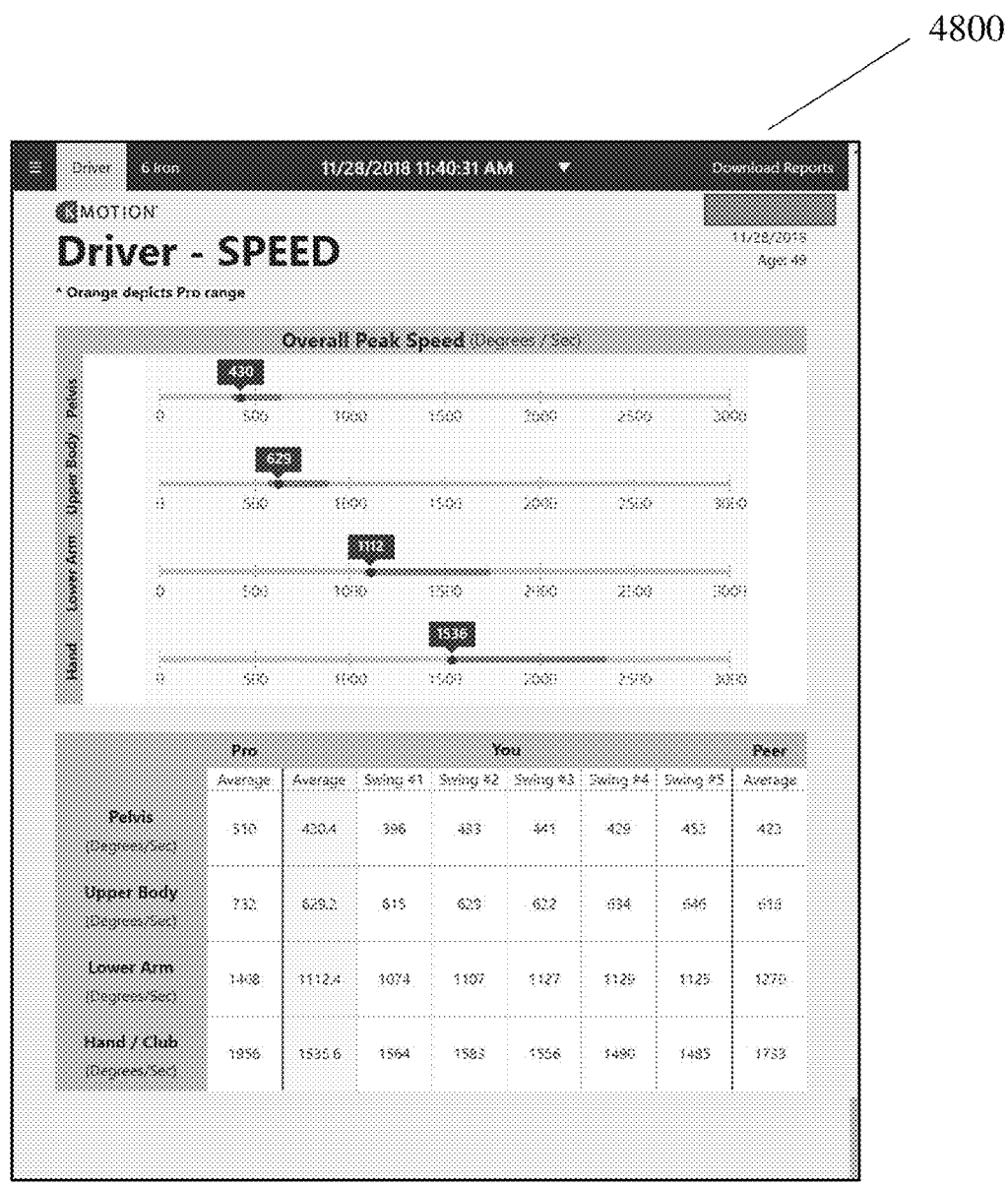
FIG. 48 is another screenshot of an Evaluation Report generated by the CPU for a golf activity according to an embodiment of the invention.

FIG. 48 is an embodiment of a Driver—Speed 4800 report that may be generated by the CPU as part of the Evaluation Report 2730. Here, for example, the CPU may compute average peak speeds (degrees/second) for various body segments (e.g., pelvis, upper body, lower arm, hand, etc.) across all Evaluation swings (shown in blue) and corresponding Pro range (shown in orange) and present them on the display as shown (top of FIG. 48) in accordance with one or more of the foregoing embodiments. Furthermore, the CPU may compute average peak speeds for each body segment for Pro (left), participant (middle), and Peers (right), as well as the participant's peak speeds for each body segment for each individual Evaluation swing (middle), and present them on the display as shown (bottom of FIG. 48) in accordance with one or more of the foregoing embodiments.

Figure 49:
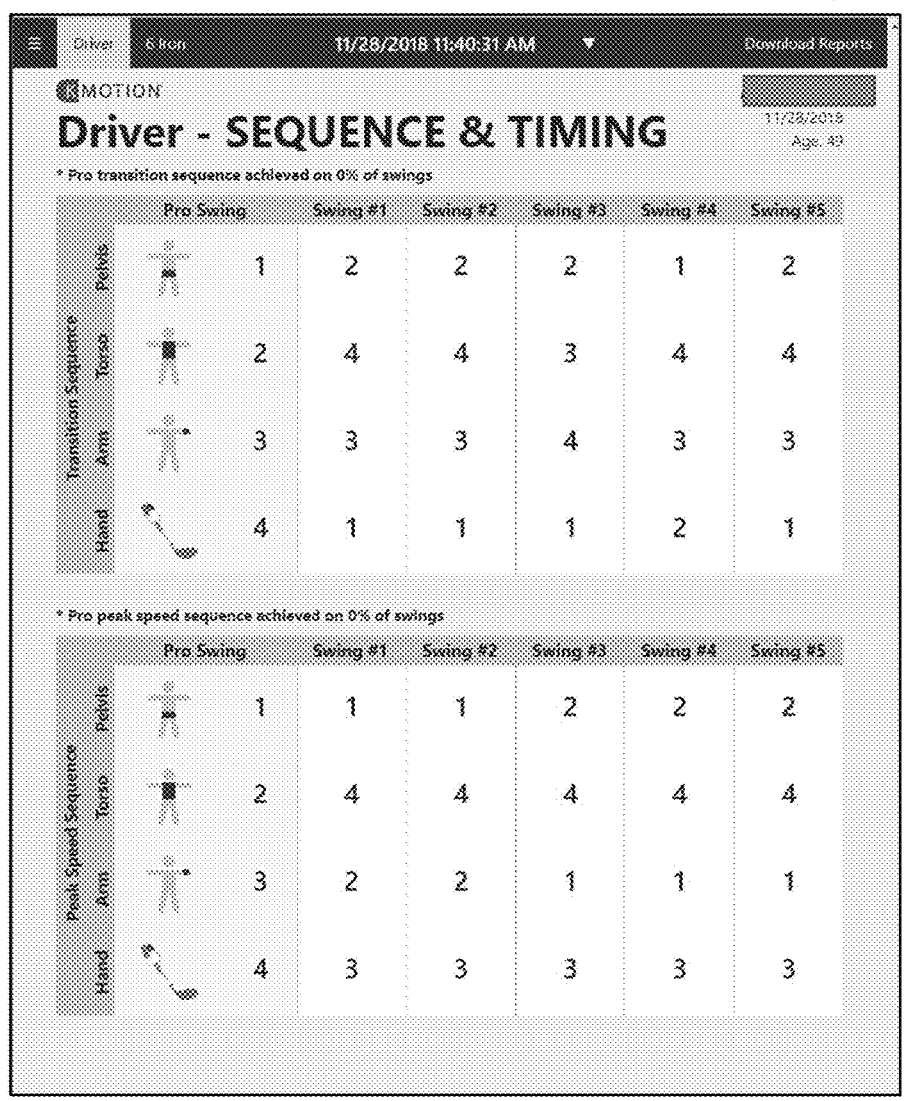
FIG. 49 is another screenshot of an Evaluation Report generated by the CPU for a golf activity according to an embodiment of the invention.

FIG. 49 is an embodiment of a Driver—Sequence & Timing 4900 report that may be generated by the CPU as part of the Evaluation Report 2730. Here, for example, the CPU may compute the participant's transition sequence, which is the order in which body segments start rotating forward, for each Individual swing, and present them on the display as shown (top of FIG. 49) in accordance with one or more of the foregoing embodiments. Furthermore, the CPU may compute the participant's peak speed sequence, which is the order in which body segments reach their peak rotational velocity, for each individual Evaluation swing, and present them on the display as shown (top of FIG. 49) in accordance with one or more of the foregoing embodiments.

Figure 50:
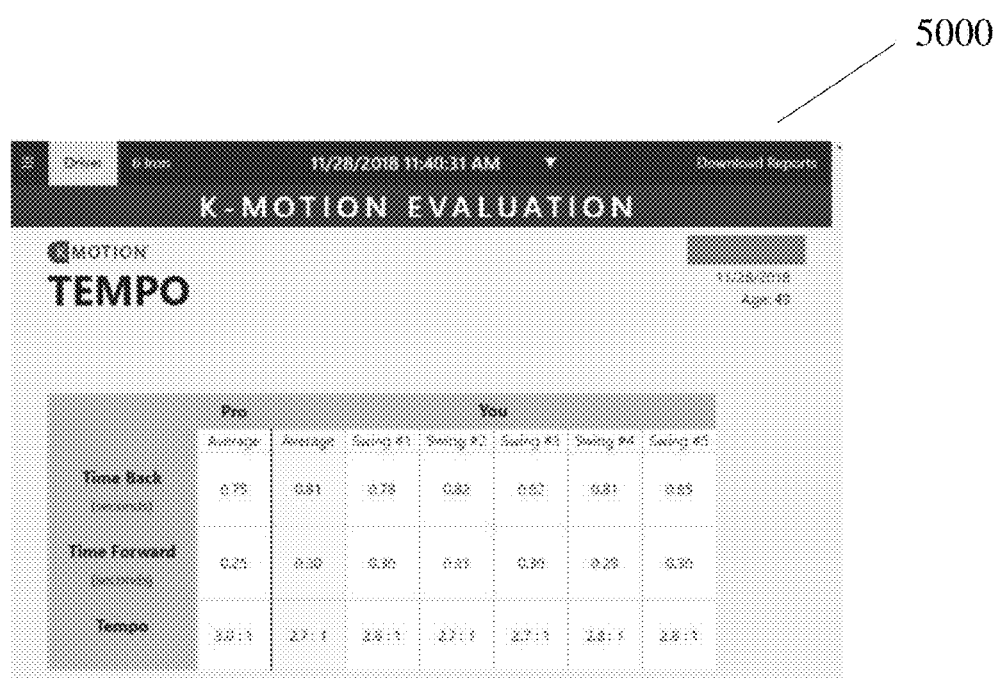
FIG. 50 is another screenshot of an Evaluation Report generated by the CPU for a golf activity according to an embodiment of the invention.

FIG. 50 is an embodiment of a Tempo 5000 report that may be generated by the CPU as part of the Evaluation Report 2730. Tempo is a measure of a participant's backswing and downswing times as a ratio (not to be confused with swing speed, which is a measure of how fast the club is moving at a particular point in the swing). Here, for example, for each swing the CPU may compute the participant's backswing time (Time Back) and downswing time (Time Forward), and then determine the participant's tempo as a ratio between Time Back and Time Forward. As shown, the CPU may present the data Average swing timing for Pro (left), player (middle), and Peers (now shown), as well as the participant's peak speeds for each body segment for each individual Evaluation swing (middle), on the display as shown in accordance with one or more of the foregoing embodiments.

FIGS. 51-55 illustrate an embodiment of an Evaluation Report 2730 for a baseball activity (swing) that is generated by the CPU in accordance with the foregoing embodiments upon the completion of a swing. As discussed above, the Evaluation Report 2730 may be stored locally and/or in the cloud, and presented on a display of the observer device 1901 and/or participant device 1903. The Evaluation Report 2730 may be generated automatically by the CPU, or generated upon user command. As described in more detail below, the processed information is reported in a unique, synchronized, multi-format presentation of the motion data.

Figure 51:
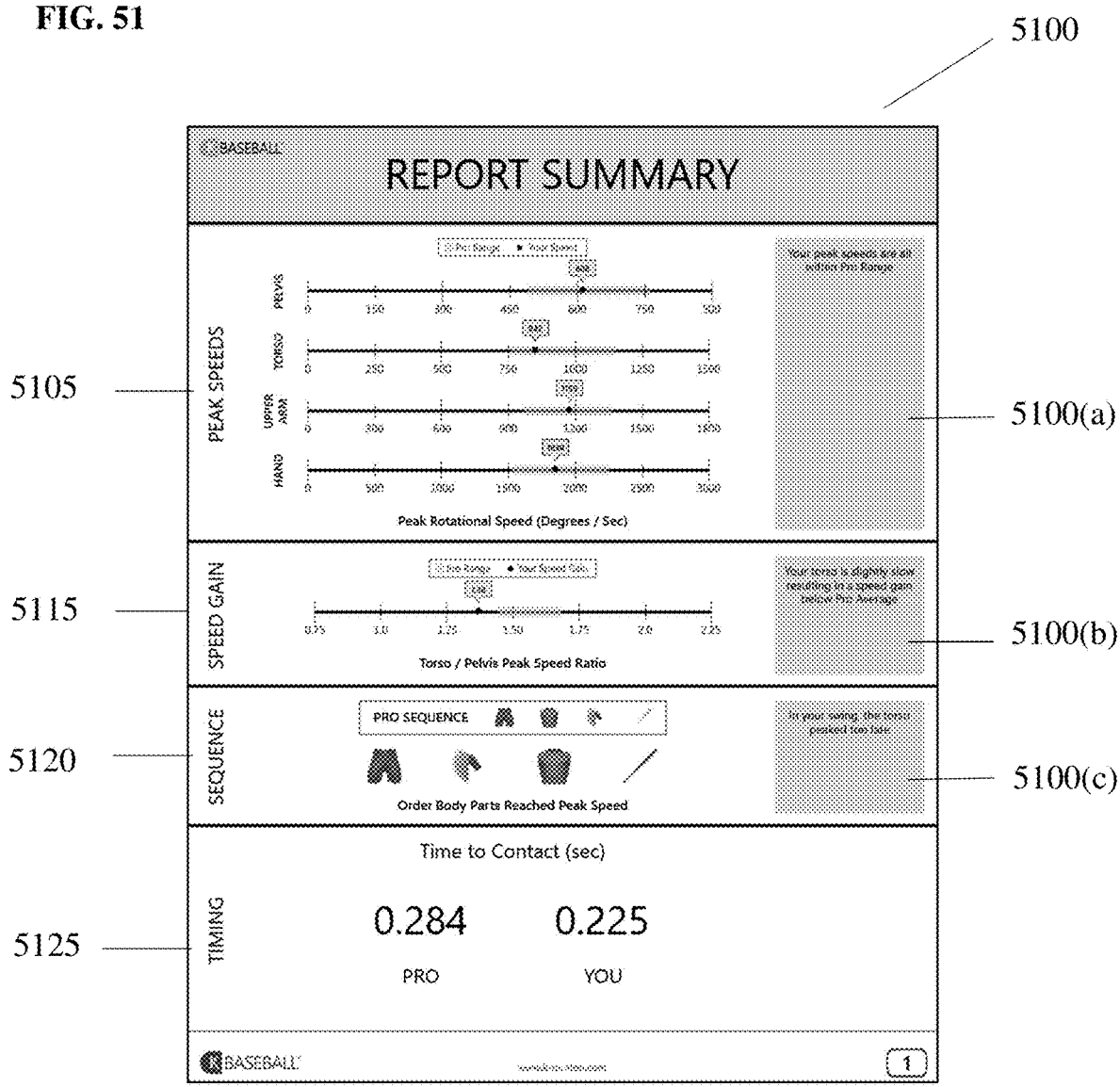
FIG. 51 is a screenshot of an Evaluation Report generated by the CPU for a baseball activity according to an embodiment of the invention.

FIG. 51 is an embodiment of an Report Summary 5100 that may be generated by the CPU as part of the Evaluation Report 2730. As shown, the Report Summary 5100 may include presentations of various motion data analyzed by the CPU in accordance with one or more of the foregoing embodiments, including as shown "Peak Speeds," "Speed Gain," "Sequence," and "Timing" (not limited thereto).

For example, the CPU may compute average Peak Speeds 5105 (degrees/second) for various body segments of interest (e.g., pelvis, torso, upper arm, hand, etc.) across all Evaluation swings (shown as a black dot) and a corresponding range for professional baseball players (shown in green) from related data stored in a database of professional baseball player data and present them on the display as shown in accordance with one or more of the foregoing embodiments. In other words, the CPU compares the participant's body segment speed against that of an average body segment speed for professional baseball players and presents the comparison on the display. The CPU may be configured to generate and present an automatically generated comment 5110 based on a determined relationship between the participant's speed segments versus that of the professional baseball players. Here, because all of the participant's measured peak speeds are within the range of the professional baseball players, the CPU is programmed to present an auto-generated comment 5110(*a*) that reads "Your peak speeds are all within Pro Range" (not limited thereto). However, in the event that all of the participant's measured average peak speeds falls below the range of professional baseball players, the CPU is programmed to present an auto-generated comment that reads, "Your peak speeds are below Pro Range". If one or more, but not all, of the participant's measured average peak speeds fall within the range of the professional baseball players, the CPU is programmed to present an auto-generated comment that reads, "Your peak speeds are partially within Pro Range."

An exemplary algorithm for generating an auto-generated comment 5110 is described below:

```
If PeakSpeedPelvis >= ProRangePeakSpeedPelvisMin Then
  NumSegmentsInProRange += 1
  If PeakSpeedTorso >= ProRangePeakSpeedTorsoMin Then
    NumSegmentsInProRange += 1
  If NumSegmentsUsed = 4 Then
    If PeakSpeedUpperArm >= ProRangePeakSpeedUpperArmMin Then
  NumSegmentsInProRange += 1
  End If
  If PeakSpeedHand >= ProRangePeakSpeedHandMin Then
    NumSegmentsInProRange += 1
  If NumSegmentsInProRange = NumSegmentsUsed Then
    Return "Your peak speeds are all within Pro Range"
  ElseIf NumSegmentsInProRange >= 1 Then
    Return "Your peak speeds are partially within Pro Range"
  Else
    Return "Your peak speeds are below Pro Range"
  End If
End Function
```

For example, the CPU may compute Speed Gain 5115 across all Evaluation swings (shown as a black dot) and a corresponding range for professional baseball players (shown in green) from related data stored in the database of professional baseball player data and present the comparison on the display as shown in accordance with one or more of the foregoing embodiments. Speed gain is the ratio between the peak speeds of adjacent segments, such as the torso/pelvis peak speed ratio. As discussed above, the CPU may generate and present an automatically generated comment 5110 based on a determined relationship between the participant's speed gain versus that of the professional baseball players. Here, because the participant's speed gain (1.38) falls below that of the range of the professional baseball players, the CPU is programmed to present an auto-generated comment 5110(*b*) that reads "Your torso is slightly low resulting in a speed gain below Pro Average" (not limited thereto).

For example, the CPU may compute Sequence 5120 across all Evaluation swings. Sequence is the order in which the participant's body parts reached peak speed. Here, the respective body parts are displayed as different color drawings representative of each body part (not limited thereto) for each recognition by the user. In this example, the order in which the participant's body parts reached peak speed was pelvis then upper arm then torso then hand. The professional baseball player sequence is displayed in the order pelvis then torso then upper arm then hand, which the CPU determines from related data stored in the database of professional baseball player data. Thus, the CPU compared the participant's sequence with that of the average professional baseball player and determined that the participant's order was not consistent with that of the professional baseball player because the participant's torso speed peaked too late. Here, because the participant's torso speed peaked too late as compared with the average professional baseball player, the CPU is programmed to present an auto-generated comment 5110(*c*) that reads "In your swing, the torso peaked too late" (not limited thereto).

For example, the CPU may compute Timing 5125 across all Evaluation swings. Timing is the calculated time between when the heel contacts the ground and the bat contacts the ball. The CPU automatically calculates this time for each swing based on the captured motion sensor data from at least the hand sensor and the pelvis and torso sensors. Timing is typically measured in seconds. Here, the participant's measured time to contact is 0.225 seconds, which is much faster than that of the average professional baseball player which measures 0.284 seconds. Although not shown, like above, the CPU may be programmed to automatically generate and present a comment related to timing.

It is understood that the CPU may generate the Report Summary 5100 without comparison to a professional baseball players or as compared to a different category of players, such as a peer group.

Figure 52:
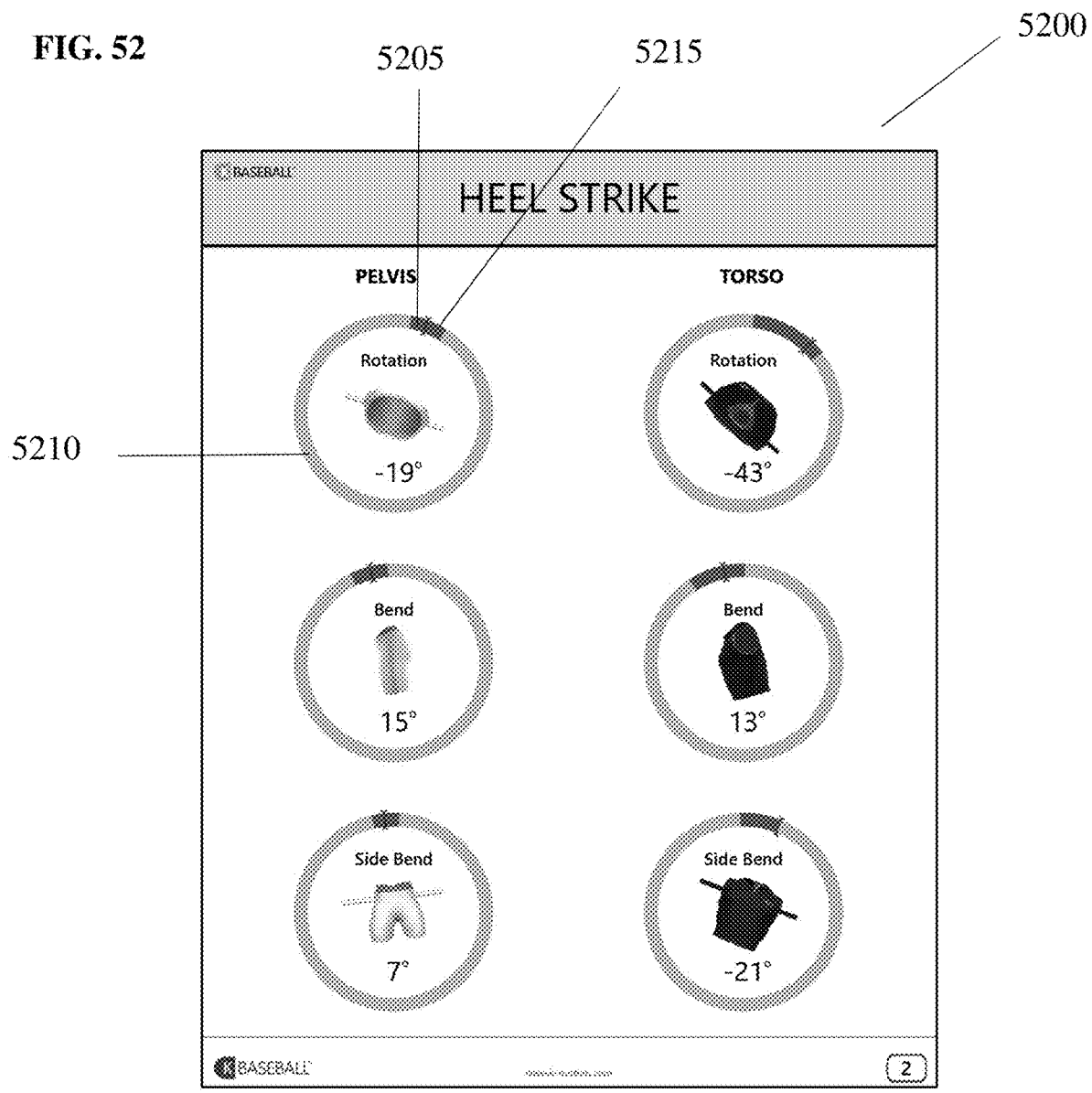
FIG. 52 is another screenshot of an Evaluation Report generated by the CPU for a baseball activity according to an embodiment of the invention.

FIG. 52 is an embodiment of a Heel Strike 5200 report that may be generated by the CPU as part of the Evaluation Report 2730. Heel strike is a key marker in a baseball swing. As shown, the Heel Strike 5200 report may include presentations of various motion data computed by the CPU in accordance with body angles for the heel strike position in a baseball swing. For example, the tic mark 5205 on the circle 5210 for each body metric (rotation, bend, side bend) of each body segment (pelvis, torso) represents the angle of the body metric. The green area 5215 on each circle represents the range for professional players.

Figure 53:
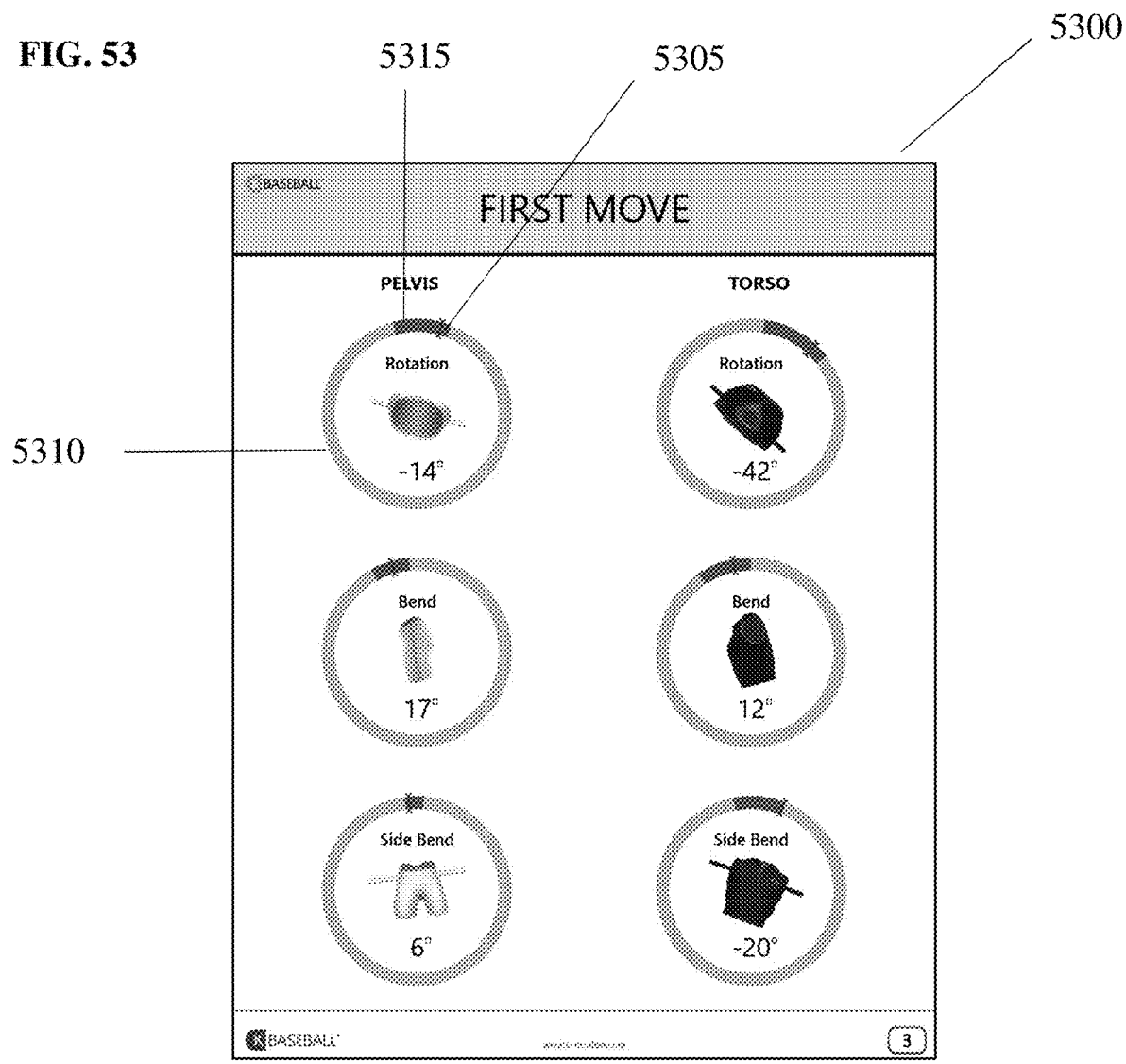
FIG. 53 is another screenshot of an Evaluation Report generated by the CPU for a baseball activity according to an embodiment of the invention.

FIG. 53 is an embodiment of a First Move 5300 report that may be generated by the CPU as part of the Evaluation Report 2730. As shown, the First Move 5300 report shows body angles computed by the CPU for the First Move position in a baseball swing. First Move represents when the batter's hand first starts moving towards the pitcher. As discussed above, the tic mark 5305 on the circle 5310 for each body metric (rotation, bend, side bend) of each body segment (pelvis, torso) represents the angle of the body metric, and the green area 5315 on each circle represents the range for professional players.

Figure 54:
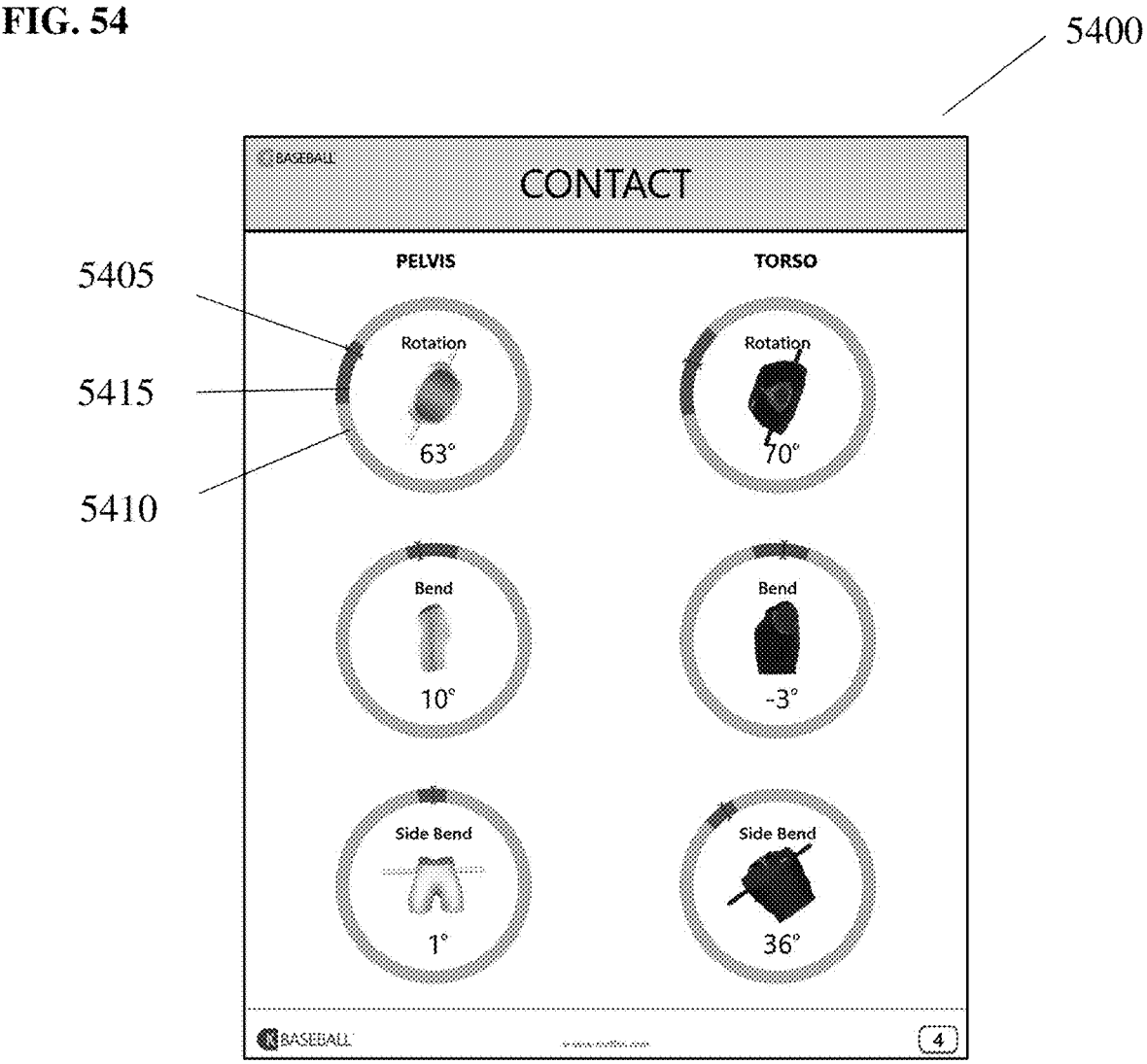
FIG. 54 is another screenshot of an Evaluation Report generated by the CPU for a baseball activity according to an embodiment of the invention.

FIG. 54 is an embodiment of a Contact 5400 report that may be generated by the CPU as part of the Evaluation Report 2730. Contact is the point in time during a swing when the bat strikes the ball. As shown, the Contact 5400 report shows various body angles computed by the CPU for the Contact position in a baseball swing. As discussed above, the tic mark 5405 on the circle 5410 for each body metric (rotation, bend, side bend) of each body segment (pelvis, torso) represents the angle of the body metric, and the green area 5415 on each circle represents the range for professional players.

Figure 55:
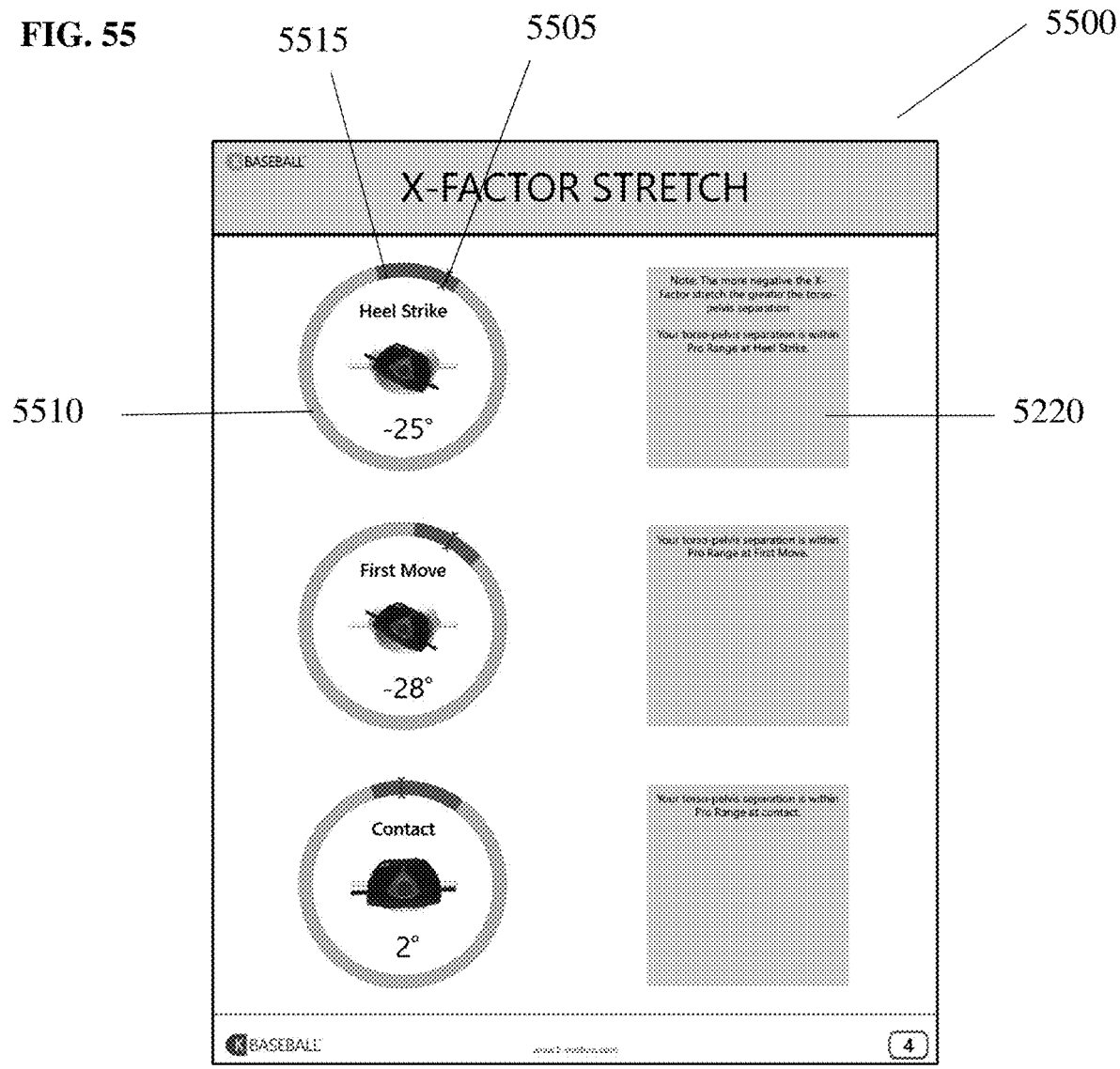
FIG. 55 is another screenshot of an Evaluation Report generated by the CPU for a baseball activity according to an embodiment of the invention.

FIG. 55 is an embodiment of an X-Factor Stretch 5500 report that may be generated by the CPU as part of the Evaluation Report 2730. The X-Factor is the relationship between the torso and pelvis, which is calculated by the CPU based on captured motion sensor data at the key swing points Heel Strike, First Move, and Contact (not limited thereto). As discussed above, the tic mark 5505 on the circle 5510 for each key swing point represents the angle of the body metric (here, torso-pelvis), and the green area 5515 on each circle represents the range for professional players. As discussed above, the CPU may generate and present automatically generated comments 5110 based on a determined relationship between the participant's X-Factor measured at each of the key swing points versus that of the professional baseball players, such as shown in FIG. 55.

Figure 56:
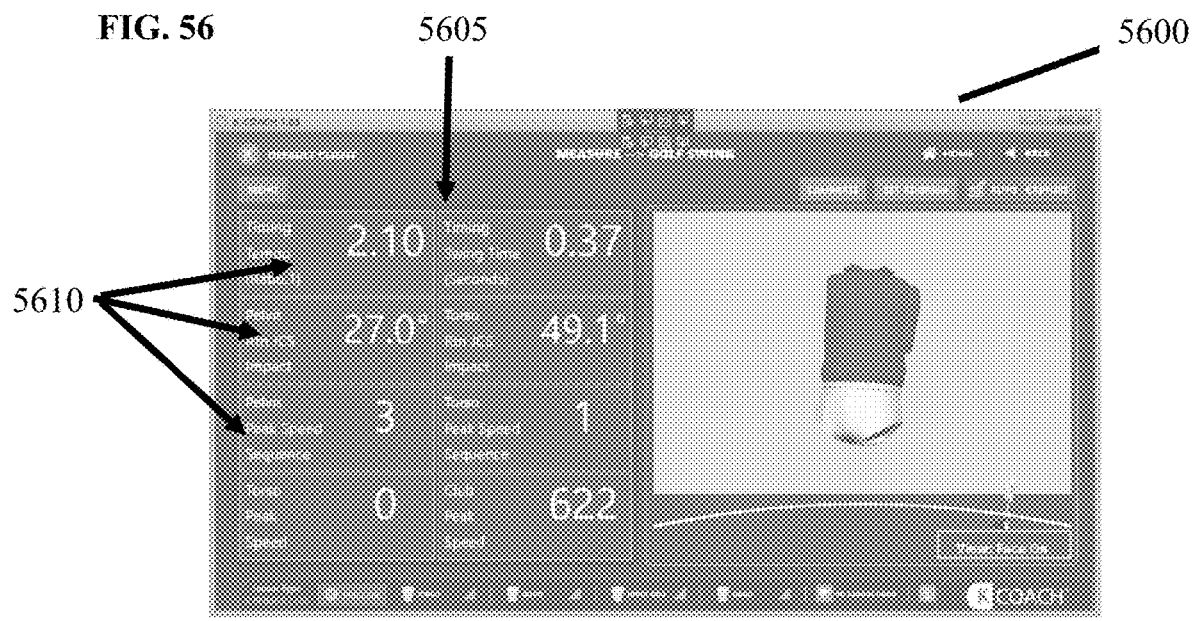
FIG. 56 is a screenshot of a graphical user interface generated by the CPU having a Tile Display according to an embodiment of the invention.
Figure 57:
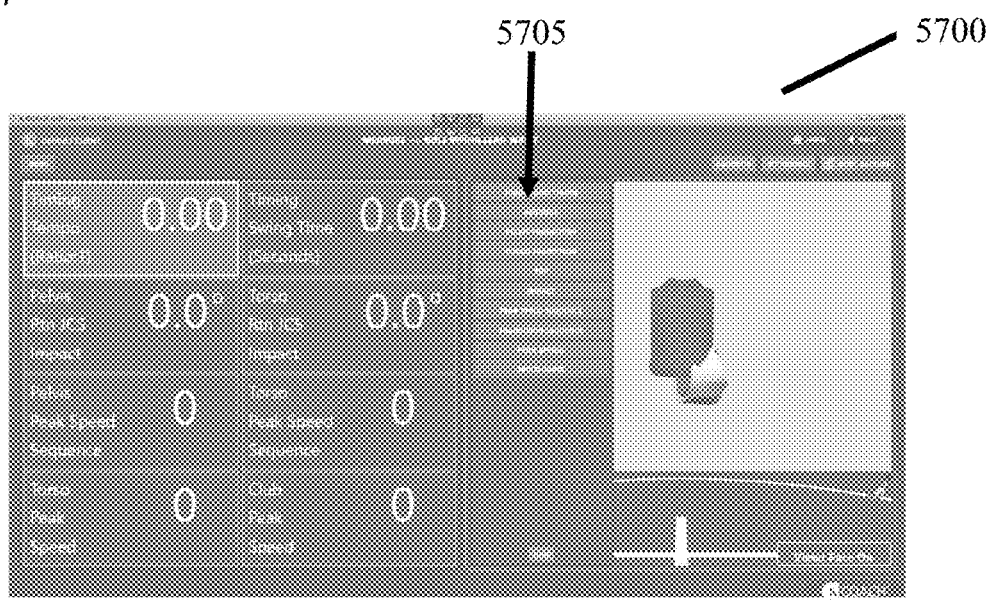
FIG. 57 is another screenshot of a graphical user interface generated by the CPU having a Tile Display according to an embodiment of the invention.

According to an embodiment of the invention, as illustrated in exemplary FIGS. 56 and 57, the CPU may be configured to generate a graphical user interface having a Tile Display 5605, which is a customizable graphical user interface having an area divided into tiles 5610 (a plurality of sub-areas) and content sources applied to each tile 5610 by the CPU. The tiles 5610 may be arranged horizontally and vertically within the Tile Display 5605. For example, the CPU may assign various 3D data to one or more tile 5610, such as related to swing timing, swing sequencing, body segment orientations and wrist angles at key swing points, peak rotational velocities, etc.) immediately following each movement—e.g., golf or baseball swing.

For example, in Auto Capture mode (discussed above), a user may simply take a swing and the motion is detected, automatically recorded, and processed by the CPU, and then each of the tiles in the Tile Display 5605 is updated with the appropriate movement data by the CPU. To facilitate faster training feedback loops, the Tiles Display 5605 is displayed next to the 3D avatar in the AutoCapture screen, such as shown in FIG. 56. The Tiles 5610 are also configurable so that users (coaches or players) can focus on specific metrics that they are interested in improving. Clicking or pressing on a Tile 5610 (Torso Tempo in this example), shown in FIG. 57 causes a pop out menu 5705 to appear, which allows the user to assign a different metric to the selected Tile 5610. This way, the user can configure the Tiles 5610 to show exactly which metrics they are interested in seeing. Clicking on a particular item in this menu expands that option to reveal individual metrics as shown in the image below.

According to the foregoing, the invention in one aspect provides a method and system for analyzing and improving the performance of an athletic motion (e.g., golf swing, baseball swing, yoga, dance, etc.) or body movement (lifting, walking, etc.) to monitor a user's accountability, which involves: 1) capturing motion sensor data for a user (e.g. through body worn sensors (e.g., inertial or movement sensors) and optionally with video cameras, time of flight cameras, or radar-based systems capable of capturing 2D or 3D scene information at regular time intervals); 2) transmitting the captured motion sensor data (all or select portions of the data) to the cloud for processing by a CPU or server that provide services for monitoring (continually or at predetermined time periods of interest), storing, processing, and communicating sensor data and instructions between devices of the system, such as participant devices and/or observer devices; 3) generating by the CPU one or more user interfaces with dashboards that present snapshots, progress reports, comparisons to development path, etc. to be displayed on the participant devices and/or observer devices; 4) automatically creating by the CPU an exercise program with biofeedback (or only video/animation) for the user based on machine learning techniques that measure, analyze, and process the motion data; 5) transmitting the training program to the user via a network; 6) monitoring by the CPU the user's compliance with the training program against a baseline threshold competency; and 7) alerting the user and/or a coach/observer in real time if the user's compliance falls below the baseline threshold competency by sending a message to a web portal, via text message, e-mail message, etc., which may order the user to stop and/or guide the user through a protocol to remind them of the correct movement pattern via instructions (graphical, video, and/or textual) displayed on any display or recipient device configured to convey feedback to the user.

The foregoing method descriptions and the process flow diagrams are provided merely as illustrative examples and are not intended to require or imply that the steps of the various embodiments must be performed in the order presented. The steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A method for processing and training a dynamic body motion, comprising:

receiving, by a central processing unit (CPU), sensor data for a dynamic body motion for an exercise from one or more sensors worn by a user that are configured to communicate the sensor data;

analyzing, by the CPU, the received sensor data to form motion data related to one or more components of the dynamic body motion;

comparing, by the CPU, the motion data with stored motion parameters for a motion template T stored in a motion database;

computing, by the CPU, a similarity score between the motion data and the stored motion parameters for the motion template T;

generating, by the CPU, in real time a first biofeedback signal when the similarity score is outside a predetermined acceptable range, and in real time a second biofeedback signal that is different than the first biofeedback signal when the similarity score is within the predetermined acceptable range; and automatically prescribing, by the CPU, an exercise regime stored in the motion database based upon the computed similarity score for use in a biofeedback training exercise, wherein the similarity score is computed by:

creating the motion template T having an M×N matrix, wherein each of the M rows represents a motion parameter time series of length N, creating a motion template S having an M×K matrix from the received sensor data consisting of K samples, where K≥N, such that each of the M rows represents the same motion parameters included in the motion template T, aligning the motion template S with the motion template T using cross-correlation and truncate non-overlapping columns as follows:

i. selecting a motion parameter row to use for alignment, ii. calculating a lag $\tau$ between $T_{i,*}$ and $$S_{i,*} \text{ as}: \tau = \underset{n}{\operatorname{argmax}}(T_{i,*} \star S_{i,*})[n], \text{ and}$$

iii. If 0≤τ≤K−N, then truncate the first τ columns and last (K−N−τ) columns of S to yield M×N matrix $$\hat{S} = \begin{bmatrix} s_{0,\tau} & \cdots & s_{0,\tau+N-1} \\ \vdots & \ddots & \vdots \\ s_{M,\tau} & \cdots & s_{M,\tau+N-1} \end{bmatrix},$$

and if τ<0 or τ>K−N, then stop and raise an error indicating that the received sensor data does not contain data matching the entire motion template T, and computing the similarity score as a weighted sum of normalized root mean square error (NRMSE) values between corresponding rows of Ŝ and T wherein each value $w_i$ is a scalar weight applied to the NRMSE for row i $$\text{Similarity Score} = \sum_{i=0}^{M} w_i * \frac{\|T_{i,*} - \hat{S}_{i,*}\|}{\|T_{i,*}\|}.$$

wherein $T_i$ is a time series of a single motion parameter from the motion template T for a row i of the M×N matrix, $S_i$ is a time series of a single motion parameter from the motion template S for a row i of the M×K matrix, and n refers to an index of each time series $T_i$ and $S_i$.

2. The method of claim 1, wherein the one or more sensors worn by the user comprise one or more inertial sensors.

3. The method of claim 1, wherein the exercise is a body motion related to a golf swing.

4. The method of claim 1, wherein the exercise is a body motion related to a baseball bat swing.

5. The method of claim 1, wherein the motion parameters comprise at least one of 3D orientation data, 3-axis sensor data obtained from the one or more body mounted sensors, heat sensor data, image sensor data, and biomechanical parameters.

6. The method of claim 5, wherein the biomechanical parameters comprise at least one of a shoulder flexion, hip flexion, hand flexion, upper arm flexion, shoulder tilt, hip tilt, hand tilt, upper arm tilt, shoulder alignment, hip alignment, hand alignment, upper arm alignment, shoulder rotation, hip rotation, hand rotation, upper arm rotation, pelvis rotation, torso rotation, shoulder lateral bend, hip lateral bend, hand lateral bend, upper arm lateral bend, shoulder pitch, hip pitch, hand pitch, upper arm pitch, shoulder angle, hip angle, hand angle, upper arm angle, shoulder direction, hip direction, hand direction, upper arm direction, torso rotational velocity, pelvis rotational velocity, hand rotational velocity, upper arm rotational velocity, spine angle, pelvis angle, wrist angle, spine direction, pelvis direction, wrist direction, upper body bend, upper body side bend, pelvis bend, pelvis side bend.

7. The method of claim 1, further comprising:
monitoring, by the CPU, in real time, user compliance with the prescribed exercise regime based on the similarity score computed for each dynamic body motion, wherein when the similarity score is determined to be outside the predetermined acceptable range, an alert is transmitted to an observer in real time so that the observer can revise or change the exercise regime.

8. A computer method for automatically developing and prescribing a user-specific training regime based on player comparison, comprising:
receiving, by a central processing unit (CPU), sensor data for a user's dynamic body motion from one or more sensors that are configured to communicate the sensor data;

analyzing, by the CPU, the received sensor data to form motion data related to one or more components of the dynamic body motion;

comparing, by the CPU, the motion data with stored motion parameters for a plurality of motion templates stored in a motion database, each of the motion templates associated with a movement for a player;

generating, by the CPU, a similarity score between the motion data and each of the plurality of motion templates;

selecting one of the plurality of motion templates based at least in part on the generated similarity scores;

automatically prescribing, by the CPU, an exercise regime stored in the motion database based upon the selected motion template, whereby the prescribed exercise regime comprises one or more exercises for the user to perform so that the user's motion data will more closely approach a match to the stored motion parameters for the selected motion template of the player;

comparing, by the CPU, the user's motion data during performance of the prescribed exercise regime with the stored motion parameters for the selected motion template;

generating a match-based similarity score based on a comparison of the user's motion data during performance of the prescribed exercise regime and the selected motion template, whereby the match-based similarity score represents a degree of mismatch based on the comparison; and generating, by the CPU, a user interface displaying the comparison of the user's motion data with the stored motion parameters for the selected motion template and the match-based similarity score, wherein the similarity score is computed by:

creating a motion template T from the plurality of motion templates, the motion template T having an M×N matrix, wherein each of the M rows represents a motion parameter time series of length N, creating a motion template S having an M×K matrix from a captured motion consisting of K samples, where K≥N, such that each of the M rows represents the same motion parameters included in the motion template T, aligning the motion template S with the motion template T using cross-correlation and truncate non-overlapping columns as follows:
  i. selecting a motion parameter row to use for alignment,
  ii. calculating a lag τ between $T_{i,*}$ and $$S_{i,*} \text{ as}: \tau = \underset{n}{\text{argmax}}(T_{i,*} \star S_{i,*})[n], \text{ and}$$

iii. If 0≤τ≤K−N, then truncate the first τ columns and last (K−N−τ) columns of S to yield M×N matrix $$\hat{S} = \begin{bmatrix} s_{0,\tau} & \cdots & s_{0,\tau+N-1} \\ \vdots & \ddots & \vdots \\ s_{M,\tau} & \cdots & s_{M,\tau+N-1} \end{bmatrix},$$

and if r<0 or r >K−N, then stop and raise an error indicating that the received sensor data does not contain data matching the entire motion template T, and computing the similarity score as a weighted sum of normalized root mean square error (NRMSE) values between corresponding rows of $\hat{S}$ and T wherein each value $w_i$ is a scalar weight applied to the NRMSE for row i $$\text{Similarity Score} = \sum_{i=0}^{M} w_i * \frac{\|T_{i,*} - \hat{S}_{i,*}\|}{\|T_{i,*}\|}$$

wherein $T_i$ is a time series of a single motion parameter from the motion template T for a row i of the M×N matrix, $S_i$ is a time series of a single motion parameter from the motion template S for a row i of the M×K matrix, and n refers to an index of each time series $T_i$ and $S_i$.

9. The computer method of claim 8, wherein the step of selecting one of the plurality of motion templates is further based on physical characteristics of the user.

* * * * *